(12) United States Patent
Leanna et al.

(10) Patent No.: US 6,878,844 B2
(45) Date of Patent: Apr. 12, 2005

(54) SYNTHESIS OF ACYCLIC NUCLEOSIDE DERIVATIVES

(75) Inventors: M. Robert Leanna, Grayslake, IL (US); Michael Rasmussen, Kenosha, WI (US); Howard Morton, Gurnee, IL (US); Zhenping Tian, Grayslake, IL (US); Daniel Plata, Wadsworth, IL (US); Bradley D. Gates, Mount Prospect, IL (US); Bikshandarkoil A. Narayanan, Mundelein, IL (US)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 10/315,580

(22) Filed: Dec. 9, 2002

(65) Prior Publication Data

US 2004/0024214 A1 Feb. 5, 2004

Related U.S. Application Data

(60) Division of application No. 09/692,599, filed on Oct. 18, 2000, which is a division of application No. 09/130,214, filed on Aug. 6, 1998, now Pat. No. 6,184,376, which is a continuation-in-part of application No. 09/020,231, filed on Feb. 6, 1998, now abandoned.
(60) Provisional application No. 60/055,153, filed on Aug. 8, 1997, and provisional application No. 60/037,517, filed on Feb. 10, 1997.

(51) Int. Cl.[7] ............................................... C07C 69/00
(52) U.S. Cl. .................... 560/129; 560/179; 560/231
(58) Field of Search ................................. 560/129, 179, 560/231; 514/261

(56) References Cited

U.S. PATENT DOCUMENTS

| | | | |
|---|---|---|---|
| 5,216,141 A | 6/1993 | Benner | |
| 5,284,837 A | 2/1994 | Lindborg | |
| 5,565,461 A | 10/1996 | Lindborg | |
| 5,608,064 A | 3/1997 | Singh et al. | |
| 5,656,617 A | 8/1997 | Lindborg | |
| 5,869,493 A | * 2/1999 | Engelhardt et al. | ......... 514/261 |

FOREIGN PATENT DOCUMENTS

| | | |
|---|---|---|
| EP | 0343133 | 11/1989 |
| EP | 0694547 | 1/1996 |
| EP | 0728757 | 8/1996 |
| EP | 0827960 | 3/1998 |
| WO | WO8910923 | 11/1989 |
| WO | WO9408951 | 4/1994 |
| WO | WO9522330 | 8/1995 |
| WO | WO9730051 | 8/1997 |
| WO | WO 97/30051 | * 8/1997 ................. 560/129 |
| WO | WO9730052 | 8/1997 |
| WO | WO 97/30052 | * 8/1997 ................. 560/129 |
| WO | WO9834917 | 8/1998 |

OTHER PUBLICATIONS

J.F. Nave et al., Biorganic & Medicinal Chemistry Letters 6 179–184 (1996).
K. Oshawa et al., Chem. Pharm Bull. 41 1906–1909 (1993).
Chem. Pharm. Bull. 39(3) 823–25 (1991) Terao et al "Synthesis of chiral . . . ".
J. Am. Chem. Soc. 113(1991) 315–7 Halazy et al "9–(Difluorophosphonoalkyl) . . . ".
J. Med. Chem. 35(8) 1458–65 (1992) Vandendriessache et al "Synthesis and . . . ".
Tetrahedron 46(19) 6903–14 (1990) Geen et al "The effect of the C–6 . . . ".
Tetrahedron Asymmetry 6(4) 973–84 (1995) Perez–Perez et al "Stereocontrolled . ".
J. Chem. Soc., Chem. Comun. (1990) 955–6 Section 6 Ashwell et al.

* cited by examiner

*Primary Examiner*—Rita Deasi
*Assistant Examiner*—Hector M. Reyes
(74) *Attorney, Agent, or Firm*—Birch, Stewart, Kolasch & Birch, LLP

(57) ABSTRACT

Methods and novel intermediates for the preparation of acyclic nucleoside derivatives of the formula:

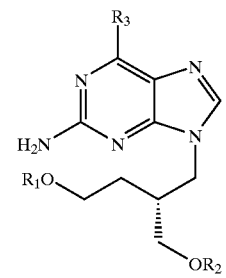

where one of $R_1$ and $R_2$ is an amino acid acyl group and the other of $R_1$ and $R_2$ is a $—C(O)C_3–C_{21}$ saturated or monounsaturated, optionally substituted alkyl and $R_3$ is OH or H; or a pharmaceutically acceptable salt thereof.

11 Claims, No Drawings

US 6,878,844 B2

SYNTHESIS OF ACYCLIC NUCLEOSIDE DERIVATIVES

This application is a divisional of application Ser. No. 09/692,599, filed on Oct. 18, 2000, which is a divisional of application Ser. No.09/130,214, filed in the United States on Aug. 6, 1998 now U.S. Pat. No. 6,184,376, which is a continuation-in-part of Ser. No. 09/020,231, filed in the United States on Feb. 6, 1998 now abandoned, the entire contents of which are hereby incorporated by reference and for which priority is claimed under 35 U.S.C. §120; and this application claims priority of provisional Application No. 60/055,153, filed in the United States on Aug. 8, 1997 and also claims priority of provisional Application No. 60/037,517, filed in the United States on Feb. 10, 1997 under 35 U.S.C. §119, the entire contents of which are hereby incorporated by reference.

TECHNICAL FIELD

This invention relates to the field of antivirals and in particular to derivatives of acyclic nucleosides useful against herpes and retroviral infections and methods for their manufacture and novel intermediates.

BACKGROUND OF THE INVENTION

The practical utility of many acyclic nucleosides is limited by their relatively modest pharmacokinetics. A number of prodrug approaches have been explored in an effort to improve the bioavailability of acyclic nucleosides in general. One of these approaches involves the preparation of ester derivatives, particularly aliphatic esters, of one or more of the hydroxy groups on the acyclic side chain.

European patent EP 165 289 describes the promising antiherpes agent 9-[4-hydroxy-(2-hydroxymethyl)butyl] guanine, otherwise known as H2G. European patent EP 186 640 discloses 6-deoxy H2G. European patent EP 343 133 discloses that these compounds, particularly the R-(-) enantiomer, are additionally active against retroviral infections such as HIV. Various derivatives of H2G, such as phosphonates, aliphatic esters (for example, the diacetate and the dipropionate) and ethers of the hydroxy groups on the acyclic side chain are disclosed in EP 343 133. This patent also discloses methods for the preparation of these derivatives comprising the condensation of the acyclic side chain to the N-9 position of a typically 6-halogenated purine moiety or, alternatively, the imidazole ring closure of a pyrimidine or furazano-[3,4-d]-pyrimidine moeity or the pyrimidine ring closure of an imidazole moiety, where the acyclic side chain is already present in the precursor pyrimidine or imidazole moiety, respectively. In the broadest description of each of these methods the acyclic side chain is pre-derivatised but individual examples also show a one-step diacylation of H2G with acetic or proprionic anhydride and DMF.

Harnden, et al., J. Med. Chem. 32, 1738 (1989) investigated a number of short chain aliphatic esters of the acyclic nucleoside 9-[4-hydroxy-(3-hydroxymethyl)butyl]guanine, otherwise known as penciclovir, and its 6-deoxy analog. Famciclovir, a marketed antiviral agent, is the diacetyl derivative of 6-deoxy penciclovir.

Benjamin, et al., Pharm. Res. 4 No. 2, 120 (1987) discloses short chain aliphatic esters of 9-[(1,3-dihydroxy-2-propoxy)-methyl]guanine, otherwise known as ganciclovir. The dipropionate ester is disclosed to be the preferred ester.

Lake-Bakaar, et al., discloses in Antimicrob. Agents Chemother. 33 No. 1, 110–112 (1989) diacetate and dipropionate derivatives of H2G and monoacetate and diacetate derivatives of 6-deoxy H2G. The diacetate and dipropionate derivatives of H2G are reported to result in only modest improvements in bioavailability relative to H2G.

International patent application WO94/24134, published Oct. 27, 1994, discloses aliphatic ester prodrugs of the 6-deoxy N-7 analog of ganciclovir, including the di-pivaloyl, di-valeroyl, mono-valeroyl, mono-oleoyl and mono-stearoyl esters.

International patent application WO93/07163, published Apr. 15, 1993 and International patent application WO94/22887, published Oct. 13, 1994, both disclose mono-ester derivatives of nucleoside analogs derived from mono-unsaturated C18 or C20 fatty acids. U.S. Pat. No. 5,216,142, issued Jun. 1, 1993, also discloses long chain fatty acid mono-ester derivatives of nucleoside analogs.

A second approach to providing prodrugs of acyclic nucleosides involves the preparation of amino acid esters of one or more of the hydroxy groups on the acyclic side chain. European patent EP 99 493 discloses generally amino acid esters of acyclovir and European patent application EP 308 065, published Mar. 22, 1989, discloses the valine and isoleucine esters of acyclovir.

European patent application EP 375 329, published Jun. 27, 1990, discloses amino acid ester derivatives of ganciclovir, including the di-valine, di-isoleucine, di-glycine and di-alanine ester derivatives. International patent application WO95/09855, published Apr. 13, 1995, discloses amino acid ester derivatives of penciclovir, including the mono-valine and di-valine ester derivatives.

DE 19526163, published Feb. 1, 1996 and U.S. Pat. No. 5,543,414 issued Aug. 6, 1996, disclose achiral amino acid esters of ganciclovir.

European patent application EP 694 547, published Jan. 31, 1996, discloses the mono-L-valine ester of ganciclovir and its preparation from di-valyl-ganciclovir.

European patent application EP 654 473, published May 24, 1995, discloses various bis amino acid ester derivatives of 9-[(1',2'-bishydroxymethyl)-cyclopropan-1'yl] methylguanine.

International patent application WO95/22330, published Aug. 24, 1995, discloses aliphatic esters, amino acid esters and mixed acetate/valinate esters of the acyclic nucleoside 9-[3,3-dihydroxymethyl-4-hydroxy-but-1-yl]guanine. This reference discloses that bioavailability is reduced when one of the valine esters of the trivaline ester derivative is replaced with an acetate ester.

BRIEF DESCRIPTION OF THE INVENTION

We have found that diester derivatives of H2G bearing specific combinations of an amino acid ester and a fatty acid ester are able to provide significantly improved oral bioavailability relative to the parent compound (H2G). In accordance with a first aspect of the invention there is thus provided novel compounds of the formula I

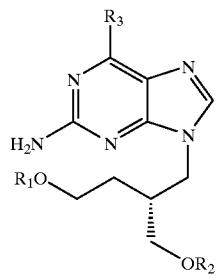

wherein
a) $R_1$ is —C(O)CH(CH(CH$_3$)$_2$)NH$_2$ or —C(O)CH(CH(CH$_3$)CH$_2$CH$_3$)NH$_2$ and $R_2$ is —C(O)C$_3$–C$_{21}$ saturated or monounsaturated, optionally substituted alkyl; or
b) $R_1$ is —C(O)C$_3$–C$_{21}$ saturated or monounsaturated, optionally substituted alkyl and $R_2$ is —C(O)CH(CH(CH$_3$)$_2$)NH$_2$ or —C(O)CH(CH(CH$_3$)CH$_2$CH$_3$)NH$_2$; and $R_3$ is OH or H;
or a pharmaceutically acceptable salt thereof.

The advantageous effect on oral bioavailability of the mixed fatty acid and amino acid esters of the invention is particularly unexpected in comparison to the oral bioavailability of the corresponding fatty acid esters. Based on the results using a urinary recovery assay (Table 1A) or a plasma drug assay (Table 1B) of H2G from rats, neither the mono or di-fatty acid esters of H2G provide any improvement in oral bioavailability relative to the parent compound H2G. Indeed the di-stearate derivative provided significantly lower bioavailability than the parent, indicating that a stearate ester may be detrimental for improving oral bioavailability of H2G. Converting one or both of the hydroxyls in certain other acyclic nucleoside analogues to the corresponding valine or di-valine ester has been reported to improve bioavailability. Conversion of H2G to the corresponding mono- or di-valyl ester derivatives produced similar improvement in bioavailability relative to the parent compound. Given that fatty acid derivatives of H2G are shown to be detrimental for improving bioavailability, it was unexpected that a mixed amino acid/fatty acid diester derivative of H2G would provide improved or comparable oral bioavailability to that of the valine diester derivative of H2G, based on urine recovery and plasma drug assays, respectively.

TABLE 1A

| $R_1$ group | $R_2$ group | Bioavailability* |
|---|---|---|
| hydrogen | hydrogen | 8% |
| hydrogen | stearoyl | 12% |
| stearoyl | stearoyl | 1% |
| valyl | hydrogen | 29% |
| valyl | valyl | 36% |
| valyl | stearoyl | 56% |

*see Biological Example 1 below for details

TABLE 1B

| $R_1$ group | $R_2$ group | Bioavailability# |
|---|---|---|
| hydrogen | hydrogen | 3.8% |
| hydrogen | stearoyl | 1.9% |
| stearoyl | stearoyl | 0% |
| valyl | hydrogen | 31.3% |

TABLE 1B-continued

| $R_1$ group | $R_2$ group | Bioavailability# |
|---|---|---|
| valyl | valyl | 35.0% |
| valyl | stearoyl | 29% | see Biological Example 2 below for details

The invention also provides pharmaceutical compositions comprising the compounds of Formula I and their pharmaceutically acceptable salts in conjunction with a pharmaceutically acceptable carrier or diluent. Further aspects of the invention include the compounds of Formula I and their pharmaceutically acceptable salts for use in therapy and the use of these compounds and salts in the preparation of a medicament for the treatment or prophylaxis of viral infection in humans or animals.

The compounds of the invention are potent antivirals, especially against herpes infections, such as those caused by Varicella zoster virus, Herpes simplex virus types 1 & 2, Epstein-Barr virus, Herpes type 6 (HHV-6) and type 8 (HHV-8). The compounds are particularly useful against Varicella zoster virus infections such as shingles in the elderly including post herpetic neuralgia or chicken pox in the young where the duration and severity of the disease can be reduced by several days. Epstein Barr virus infections amenable to treatment with the compounds include infectious mononucleosis/glandular fever which has previously not been treatable but which can cause many months of scholastic incapacity amongst adolescents.

The compounds of the invention are also active against certain retroviral infections, notably SIV, HIV-1 and HIV-2, and against infections where a transactivating virus is indicated.

Accordingly a further aspect of the invention provides a method for the prophylaxis or treatment of a viral infection in humans or animals comprising the administration of an effective amount of a compound of Formula I or its pharmaceutically acceptable salt to the human or animal.

Advantageously group $R_3$ is hydroxy or its tautomer =O so that the base portion of the compounds of the invention is the naturally occuring guanine, for instance in the event that the side chain is cleaved in vivo. Alternatively, $R_3$ may be hydrogen thus defining the generally more soluble 6-deoxy derivative which can be oxidised in vivo (e.g. by xanthine oxidase) to the guanine form.

The compound of formula I may be present in racemic form, that is a mixture of the 2R and 2S isomers. Preferably, however, the compound of formula I has at least 70%, preferably at least 90% R form, for example greater than 95%. Most preferably the compound of formula I is enantiomerically pure R form.

Preferably the amino acid of group $R_1/R_2$ is derived from an L-amino acid.

Preferably the fatty acid of group $R_1/R_2$ has in total an even number of carbon atoms, in particular, decanoyl ($C_{10}$), lauryl ($C_{12}$), myristoyl ($C_{14}$), palmitoyl ($C_{16}$), stearoyl ($C_{18}$) or eicosanoyl ($C_{20}$). Other useful $R_1/R_2$ groups include butyryl, hexanoyl, octanoyl or behenoyl ($C_{22}$). Further useful $R_1/R_2$ groups include those derived from myristoleic, myristelaidic, palmitoleic, palmitelaidic, n6-octadecenoic, oleic, elaidic, gandoic, erucic or brassidic acids. Monounsaturated fatty acid esters typically have the double bond in the trans configuration, preferably in the ω-6, ω-9 or ω-11 position, dependent upon their length. Preferably the $R_1/R_2$ group is derived from a fatty acid which comprises a $C_9$ to $C_{17}$ saturated, or n:9 monounsaturated, alkyl.

The saturated or unsaturated fatty acid or $R_1/R_2$ may optionally be substituted with up to five similar or different substituents independently selected from the group consisting of such as hydroxy, $C_1-C_6$ alkyl, $C_1-C_6$ alkoxy, $C_1-C_6$ alkoxy $C_1-C_6$ alkyl, $C_1-C_6$ alkanoyl, amino, halo, cyano, azido, oxo, mercapto and nitro, and the like.

Most preferred compounds of the formula I are those where $R_1$ is —C(O)CH(CH(CH$_3$)$_2$)NH$_2$ or —C(O)CH(CH(CH$_3$)CH$_2$CH$_3$)NH$_2$ and $R_2$ is —C(O)C$_9$–C$_{17}$ saturated alkyl.

The term "lower alkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkanoyl" as used herein refers to $R_{20}$C(O)— wherein $R_{20}$ is a loweralkyl group.

The term "alkoxy" as used herein refers to $R_{21}$O— wherein $R_{21}$ is a loweralkyl group.

The term "alkoxyalkyl" as used herein refers to an alkoxy group appended to a loweralkyl radical.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxy-carbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyl-oxycarbonyl, 4-methoxybenzyloxycarbonyl, 2-nitro-4,5-dimethoxybenzyloxy-carbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

The term "O-protecting group" or "hydroxy-protecting group" or "—OH protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "activated ester derivative" as used herein refers to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenyl derived esters, sulfonic acid derived anhydrides (for example, p-toluenesulonic acid derived anhydrides and the like) and the like.

Preferred compounds of formula I include:
(R)-9-[2-(butyryloxymethyl)-4-(L-isoleucyloxy)butyl]guanine,
(R)-9-[2-(4-acetylbutyryloxymethyl)-4-(L-isoleucyloxy)butyl]guanine,
(R)-9-[2-(hexanoyloxymethyl)-4-(L-isoleucyloxy)butyl]guanine,
(R)-9-[4-(L-isoleucyloxy)-2-(octanoyloxymethyl)butyl]guanine,
(R)-9-[4-(L-isoleucyloxy)-2-(decanoyloxymethyl)butyl]guanine,
(R)-9-[4-(L-isoleucyloxy)-2-(dodecanoyloxymethyl)butyl]guanine,
(R)-9-[4-(L-isoleucyloxy)-2-(tetradecanoyloxymethyl)butyl]guanine,
(R)-9-[4-(L-isoleucyloxy)-2-(hexadecanoyloxymethyl)butyl]guanine,
(R)-9-[4-(L-isoleucyloxy)-2-(octadecanoyloxymethyl)butyl]guanine,
(R)-9-[2-(eicosanoyloxymethyl)-4-(L-isoleucyloxy)butyl]guanine,
(R)-9-[2-(docosanoyloxymethyl)-4-(L-isoleucyloxy)butyl]guanine,
(R)-9-[4-(L-isoleucyloxy)-2-((9-tetradecenoyl)oxymethyl)butyl]guanine,
(R)-9-[2-((9-hexadecenoyl)oxymethyl)-4-(L-isoleucyloxy)butyl]guanine,
(R)-9-[4-(L-isoleucyloxy)-2-((6-octadecenoyl)oxymethyl)butyl]guanine,
(R)-9-[4-(L-isoleucyloxy)-2-((9-octadecenoyl)oxymethyl)-butyl]guanine,
(R)-9-[2-((11-eicosanoyl)-oxymethyl)-4-(L-isoleucyloxy)butyl]guanine,
(R)-9-[2-((13-docosenoyl)-oxymethyl)-4-(L-isoleucyloxy)butyl]guanine,
(R)-2-amino-9-[2-(butyryloxymethyl)-4-(L-isoleucyloxy)butyl]purine,
R)-2-amino-9-[2-(4-acetylbutyryloxymethyl)-4-(L-isoleucyloxy)butyl]purine,
(R)-2-amino-9-[2-(hexanoyloxymethyl)-4-(L-isoleucyloxy)butyl]purine,
(R)-2-amino-9-[4-(L-isoleucyloxy)-2-(octanoyloxymethyl)butyl]purine,
(R)-2-amino-9-[4-(L-isoleucyloxy)-2-(decanoyloxymethyl)butyl]purine,
(R)-2-amino-9-[4-(L-isoleucyloxy)-2-(dodecanoyloxymethyl)butyl]purine,
(R)-2-amino-9-[4-(L-isoleucyloxy)-2-(tetradecanoyloxymethyl)butyl]purine, (R)-2-amino-9-[4-(L-isoleucyloxy)-2-(hexadecanoyloxymethyl)butyl]purine,
(R)-2-amino-9-[4-(L-isoleucyloxy)-2-(octadecanoyloxymethyl)butyl]purine,
(R)-2-amino-9-[4-(L-isoleucyloxy)-2-(eicosanoyloxymethyl)butyl]purine,
(R)-2-amino-9-[2-(eicosanoyloxymethyl)-4-(L-isoleucyloxy)butyl]purine,
(R)-2-amino-9-[2-(docosanoyloxymethyl)-4-(L-isoleucyloxy)butyl]purine,
(R)-2-amino-9-[4-(L-isoleucyloxy)-2-((9-tetradecenoyl)oxymethyl)butyl]purine,
(R)-2-amino-9-[2-((9-hexadecenoyl)oxymethyl)-4-(L-isoleucyloxy)butyl]purine,
(R)-2-amino-9-[4-(L-isoleucyloxy)-2-((6-octadecenoyl)oxymethyl)butyl]purine,
(R)-2-amino-9-[4-(L-isoleucyloxy)-2-((9-octadecenoyl)oxymethyl)butyl]purine,
(R)-2-amino-9-[2-((11-eicosanoyl)oxymethyl)-4-(L-isoleucyloxy)butyl]purine, or
(R)-2-amino-9-[2-((13-docosenoyl)oxymethyl)-4-(L-isoleucyloxy)butyl]purine,
or a pharmaceutically accepable salt thereof.

Further preferred compounds include:
(R)-9-[2-(butyryloxymethyl)-4-(L-valyloxy)butyl]guanine,
(R)-9-[2-(4-acetylbutyryloxymethyl)-4-(L-valyloxy)butyl]guanine,
(R)-9-[2-(hexanoyloxymethyl)-4-(L-valyloxy)butyl]guanine,
(R)-9-[2-(octanoyloxymethyl)-4-(L-valyloxy)butyl]guanine,
(R)-9-[2-(decanoyloxymethyl)-4-(L-valyloxy)butyl]guanine,
(R)-9-[2-(dodecanoyloxymethyl)-4-(L-valyloxy)butyl]guanine,
(R)-9-[2-(tetradecanoyloxymethyl-4-(L-valyloxy)butyl]guanine,
(R)-9-[2-hexadecanoyloxymethyl)-4-(L-valyloxy)butyl]guanine,
(R)-9-[2-(octadecanoyloxymethyl)-4-(L-valyloxy)butyl]guanine,
(R)-9-[2-(eicosanoyloxymethyl)-4-(L-valyloxy)butyl]guanine,
(R)-9-[2-(eicosanoyloxymethyl)-4-(L-valyloxy)butyl]guanine,
(R)-9-[2-(docosanoyloxymethyl)-4-(L-valyloxy)butyl]guanine,
(R)-9-[2-((9-tetradecenoyl)oxymethyl)-4-(L-valyloxy)butyl]guanine,
(R)-9-[2-((9-hexadecenoyl)oxymethyl)-4-(L-valyloxy)butyl]guanine,
(R)-9-[2-((6-octadecenoyl)oxymethyl)-4-(L-valyloxy)butyl]guanine,
(R)-9-[2-((9-octadecenoyl)oxymethyl)-4-(L-valyloxy)-butyl]guanine,
(R)-9-[2-((11-eicosanoyl)oxymethyl)-4-(L-valyloxy)butyl]guanine,
(R)-9-[2-((13-docosenoyl)oxymethyl)-4-(L-valyloxy)butyl]guanine,
(R)-2-amino-9-[2-(butyryloxymethyl)-4-(L-valyloxy)butyl]purine,
(R)-2-amino-9-[2-(4-acetylbutyryloxymethyl)-4-(L-valyloxy)butyl]purine,
(R)-2-amino-9-[2-(hexanoyloxymethyl)-4-(L-valyloxy)butyl]purine,
(R)-2-amino-9-[2-(octanoyloxymethyl)-4-(L-valyloxy)butyl]purine,
(R)-2-amino-9-[2-(decanoyloxymethyl)-4-(L-valyloxy)butyl]purine,
(R)-2-amino-9-[2-(dodecanoyloxymethyl)-4-(L-valyloxy)butyl]purine,
(R)-2-amino-9-[2-(tetradecanoyloxymethyl)-4-(L-valyloxy)butyl]purine,
(R)-2-amino-9-[2-(hexadecanoyloxymethyl)-4-(L-valyloxy)butyl]purine,
(R)-2-amino-9-[2-(octadecanoyloxymethyl)-4-(L-valyloxy)-butyl]purine,
(R)-2-amino-9-[2-(eicosanoyloxymethyl)-4-(L-valyloxy)butyl]purine,
(R)-2-amino-9-[2-(docosanoyloxymethyl)-4-(L-valyloxy)butyl]purine,
(R)-2-amino-9-[2-((9-tetradecenoyl)oxymethyl)-4-(L-valyloxy)butyl]purine,
(R)-2-amino-9-[2-((9-hexadecenoyl)oxymethyl)-4-(L-valyloxy)butyl]purine,
(R)-2-amino-9-[2-((6-octadecenoyl)oxymethyl)-4-(L-valyloxy)butyl]purine,
(R)-2-amino-9-[2-((9-octadecenoyl)oxymethyl)-4-(L-valyloxy)-butyl]purine,
(R)-2-amino-9-[2-((11-eicosenoyl)-oxymethyl)-4-(L-valyloxy)butyl]purine, or
(R)-2-amino-9-[2-((13-docosenoyl)-oxymethyl)-4-(L-valyloxy)butyl]purine;
or a pharmaceutically acceptable salt thereof.

Other preferred compounds of formula I include:
(R)-9-[4-(butyryloxy)-2-(L-valyloxymethyl)butyl]guanine,
(R)-9-[4-(4-acetylbutyryloxy)-2-(L-valyloxymethyl)butyl]guanine,
(R)-9-[4-(hexanoyloxy)-2-(L-valyloxymethyl)butyl]guanine,
(R)-9-[4-(octanoyloxy)-2-(L-valyloxymethyl)butyl]guanine,
(R)-9-[4-(decanoyloxy)-2-(L-valyloxymethyl)butyl]guanine,
(R)-9-[4-(dodecanoyloxy)-2-(L-valyloxymethyl)butyl]guanine,
(R)-9-[4-(tetradecanoyloxy)-2-(L-valyloxymethyl)butyl]guanine,
(R)-9-[4-hexadecanoyloxy)-2-(L-valyloxymethyl)butyl]guanine,
(R)-9-[4-(octadecanoyloxy)-2-(L-valyloxymethyl)butyl]guanine,
(R)-9-[4-(eicosanoyloxy)-2-(L-valyloxymethyl)butyl]guanine,
(R)-9-[4-(docosanoyloxy)-2-(L-valyloxymethyl)butyl]guanine,
(R)-9-[4-((9-tetradecenoyl)oxy)-2-(L-valyloxymethyl)butyl]guanine,
(R)-9-[4-((9-hexadecenoyl)oxy)-2-(L-valyloxymethyl)butyl]guanine,
(R)-9-[4-((6-octadecenoyl)oxy)-2-(L-valyloxymethyl)butyl]guanine,
(R)-9-[4-((9-octadecenoyl)oxy)-2-(L-valyloxymethyl)-butyl]guanine,
(R)-9-[4-((11-eicosenoyl)oxy)-2-(L-valyloxymethyl)butyl]guanine,
(R)-9-[4-((13-docosenoyl)-oxy)-2-(L-valyloxymethyl)butyl]guanine,
(R)-2-amino-9-[4-(butyryloxy)-2-(L-valyloxymethyl)butyl]purine,
(R)-2-amino-9-[4-(4-acetylbutyryloxy)-2-(L-valyloxymethyl)butyl]purine,
(R)-2-amino-9-[4-(hexanoyloxy)-2-(L-valyloxymethyl)butyl]purine, (R)-2-amino-9-[4-(octanoyloxy)-2-(L-valyloxymethyl)butyl]purine,
(R)-2-amino-9-[4-(decanoyloxy)-2-(L-valyloxymethyl)butyl]purine,
(R)-2-amino-9-[4-(dodecanoyloxy)-2-(L-valyloxymethyl)butyl]purine,
(R)-2-amino-9-[4-(tetradecanoyloxy)-2-(L-valyloxymethyl)butyl]purine,
(R)-2-amino-9-[4-(hexadecanoyloxy)-2-(L-valyloxymethyl)butyl]purine,
(R)-2-amino-9-[4-(octadecanoyloxy)-2-(L-valyloxymethyl)-butyl]purine,
(R)-2-amino-9-[4-(eicosanoyloxy)-2-(L-valyloxymethyl)butyl]purine,
(R)-2-amino-9-[4-(docosanoyloxy)-2-(L-valyloxymethyl)butyl]purine,
(R)-2-amino-9-[4-((9-tetradecenoyl)oxy)-2-(L-valyloxymethyl)butyl]purine,
(R)-2-amino-9-[4-((9-hexadecenoyl)oxy)-2-(L-valyloxymethyl)butyl]purine,
(R)-2-amino-9-[4-((6-octadecenoyl)oxy)-2-(L-valyloxymethyl)butyl]purine,
(R)-2-amino-9-[4-((9-octadecenoyl)oxy)-2-(L-valyloxymethyl)butyl]purine,
(R)-2-amino-9-[4-((11-eicosenoyl)oxy)-2-(L-valyloxymethyl)butyl]purine, or
(R)-2-amino-9-[4-((13-docosenoyl)oxy)-2-(L-valyloxymethyl)butyl]purine,
or a pharmaceutically acceptable salt thereof.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Hydrochloric acid salts are convenient.

The compounds of Formula I may be isolated as the hydrate. The compounds of the invention may be isolated in crystal form, preferably homogenous crystals, and thus an additional aspect of the invention provides the compounds of Formula I in substantially pure crystalline form, comprising >70%, preferably >90% homogeneous crystalline material, for example >95% homogeneous crystalline material.

The compounds of the invention are particularly suited to oral administration, but may also be administered rectally, vaginally, nasally, topically, transdermally or parenterally, for instance intramuscularly, intravenously or epidurally. The compounds may be administered alone, for instance in a capsule, but will generally be administered in conjunction with a pharmaceutically acceptable carrier or diluent. The invention extends to methods for preparing a pharmaceutical composition comprising bringing a compound of Formula I or its pharmaceutically acceptable salt in conjunction or association with a pharmaceutically acceptable carrier or vehicle.

Oral formulations are conveniently prepared in unit dosage form, such as capsules or tablets, employing conventional carriers or binders such as magnesium stearate, chalk, starch, lactose, wax, gum or gelatin. Liposomes or synthetic or natural polymers such as HPMC or PVP may be used to afford a sustained release formulation. Alternatively the formulation may be presented as a nasal or eye drop, syrup, gel or cream comprising a solution, suspension, emulsion, oil-in-water or water-in-oil preparation in conventional vehicles such as water, saline, ethanol, vegetable oil or glycerine, optionally with flavourant and/or preservative and/or emulsifier.

The compounds of the invention may be administered at a daily dose generally in the range 0.1 to 200 mg/kg/day, advantageously, 0.5 to 100 mg/kg/day, more preferably 10 to 50 mg/kg/day, such as 10 to 25 mg/kg/day. A typical dosage rate for a normal adult will be around 50 to 500 mg, for example 300 mg, once or twice per day for herpes infections and 2 to 10 times this dosage for HIV infections.

As is prudent in antiviral therapy, the compounds of the invention can be administered in combination with other antiviral agents, such as acyclovir, valcyclovir, penciclovir, famciclovir, ganciclovir and its prod rugs, cidofovir, foscarnet and the like for herpes indications and AZT, ddl, ddC, d4T, 3TC, foscarnet, ritonavir, indinavir, saquinavir, delaviridine, Vertex VX 478, Agouron AG1343 and the like for retroviral indications.

The compounds of the invention can be prepared de novo or by esterification of the H2G parent compound which is prepared, for example, by the synthesis methodology disclosed in European Patent EP 343 133, which is incorporated herein by reference.

A typical reaction scheme for the preparation of H2G is depicted below:

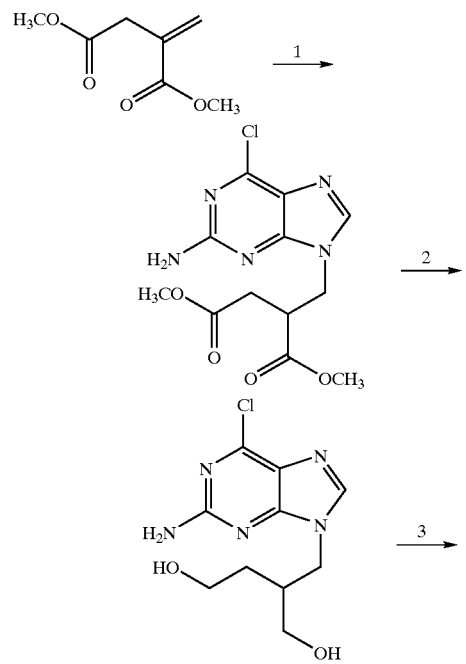

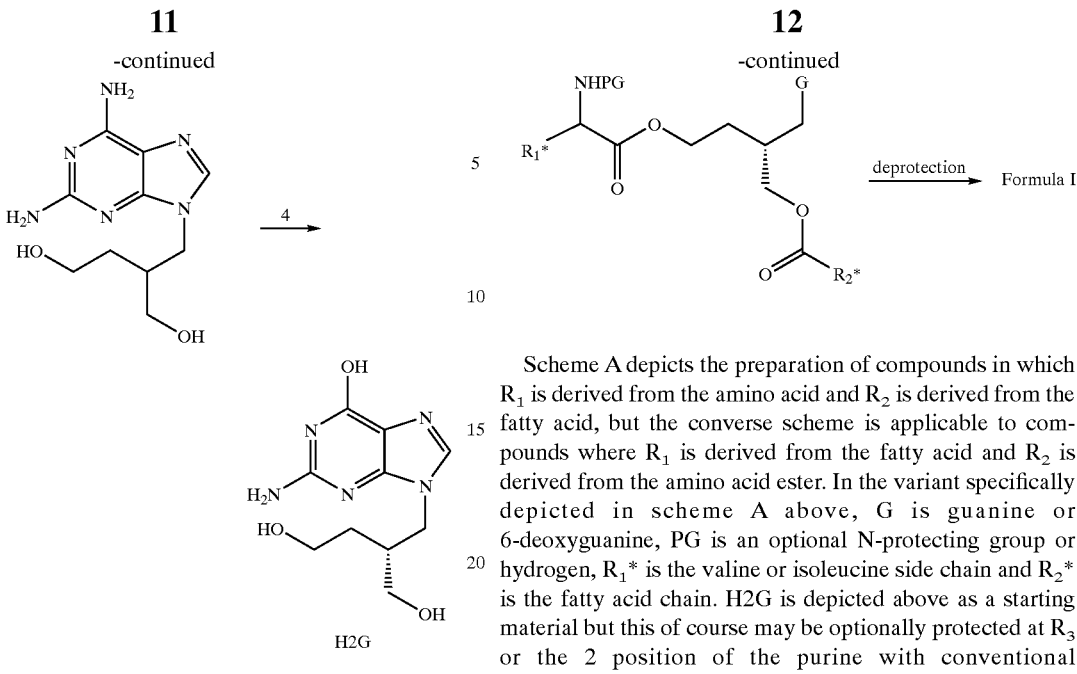

The condensation in step 1 is typically carried out with a base catalyst such as NaOH or $Na_2CO_3$ in a solvent such as DMF. Step 2 involves a reduction which can be performed with $LiBH_4$/tetrahydrofuran in a solvent such as t-BuOH. The substitution in step 3 of the chlorine with an amino group can be performed under pressure with ammonia. Step 4 employs adenosine deaminase which can be conveniently immobilized on a solid support. Cooling the reaction mixture allows unreacted isomeric precursor to remain in solution thereby enhancing purity.

Starting materials for compounds of the invention in which $R_3$ is hydrogen may be prepared as shown in European Patent EP 186 640, the contents of which are incorporated herein by reference. These starting materials may be acylated as described for H2G below, optionally after protecting the purine 2-amino group with a conventional N-protecting group as defined above, especially BOC (t-BuO—CO—), Z (BnO—CO—) or $Ph_3C$—.

The compounds of the invention may be prepared from H2G as described below in Schemes A and B.

A. Direct Acylation Method

Scheme A

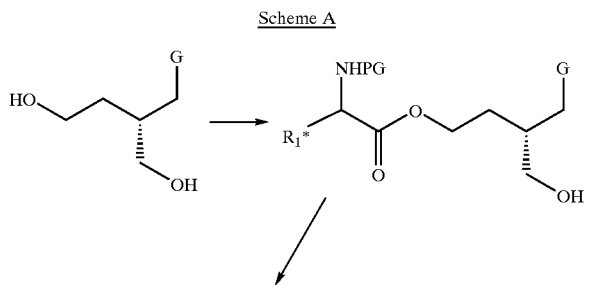

Scheme A depicts the preparation of compounds in which $R_1$ is derived from the amino acid and $R_2$ is derived from the fatty acid, but the converse scheme is applicable to compounds where $R_1$ is derived from the fatty acid and $R_2$ is derived from the amino acid ester. In the variant specifically depicted in scheme A above, G is guanine or 6-deoxyguanine, PG is an optional N-protecting group or hydrogen, $R_1^*$ is the valine or isoleucine side chain and $R_2^*$ is the fatty acid chain. H2G is depicted above as a starting material but this of course may be optionally protected at $R_3$ or the 2 position of the purine with conventional N-protecting groups (not shown). The H2G (derivative) reacts in the first step with an activated $R_1$ α-amino acid derivative, as further described below, in a solvent such as dimethylformamide or pyridine, to give a monoacylated product. The $R_1$ α-amino acid may be suitably N-protected with N-BOC or N-CBz or the like. Under controlled conditions, the first acylation can be made to predominantly take place at the side chain 4-hydroxy group on the side chain of H2G. These controlled conditions can be achieved, for example, by manipulating the reagent concentrations or rate of addition, especially of the acylating agent, by lowering the temperature or by the choice of solvent. The reaction can be followed by TLC to monitor the controlled conditions.

After purification, the $R_1$ monoacylated compounds are further acylated on the side chain 2—$CH_2OH$ group with the appropriate activated fatty acid derivative to give diacylated products using similar procedures as for the first esterification step. The diester products are subsequently subjected to a conventional deprotection treatment using for example trifluoroacetic acid, HCl(aq)/dioxane or hydrogenation in the presence of catalyst to give the desired compound of Formula I. The compound may be in salt form depending on the deprotection conditions.

The activated $R_1/R_2$ acid derivative used in the various acylations may comprise e.g. the acid halide, acid anhydride, activated acid ester or the acid in the presence of coupling reagent, for example dicyclohexylcarbodiimide, where "acid" in each case represents the corresponding $R_1/R_2$ amino acid or the $R_1/R_2$ fatty acid. Representative activated acid derivatives include the acid chloride, formic and acetic acid derived mixed anhydrides, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters, sulfonic acid derived anhydrides (for example, p-toluenesulonic acid derived anhydrides and the like) and the like.

B. Via Protection of the Side Chain 4-hydroxy Group

Scheme B

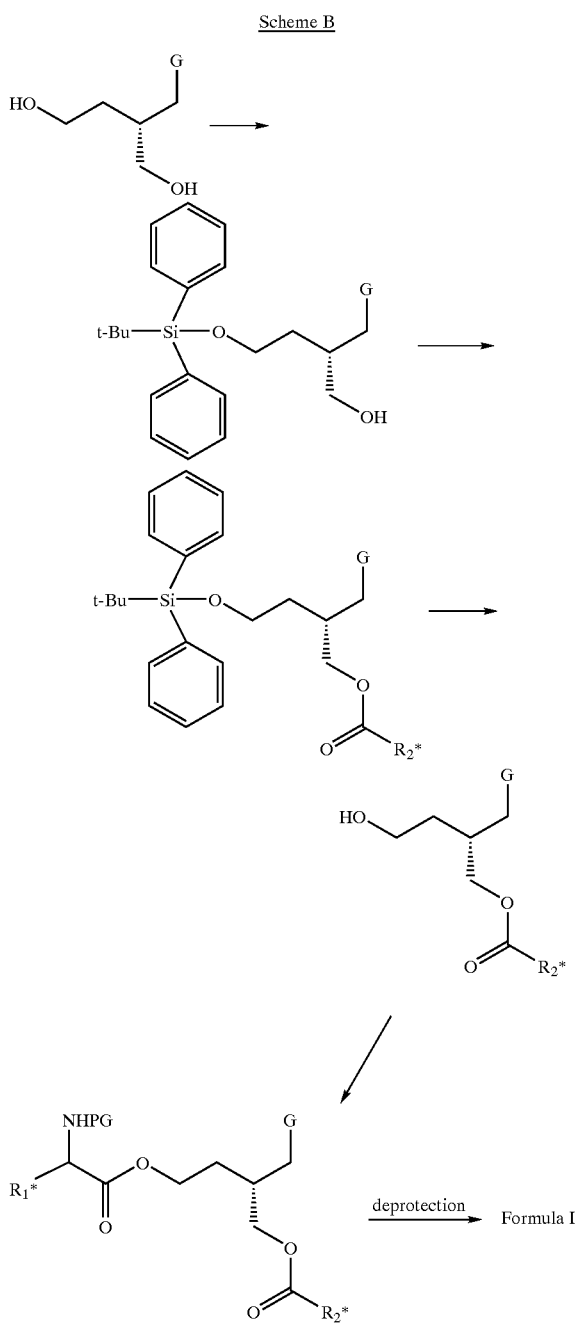

wherein G, PG, $R_1^*$ and $R_2^*$ are as described for scheme A.

Scheme B has been exemplified with reference to the preparation of a compound where $R_1$ is derived from an amino acid and $R_2$ is derived from the fatty acid ester, but a converse scheme will be applicable to compounds where $R_2$ is derived from the amino acid and $R_1$ is derived from the fatty acid. This scheme relies on regioselective protection of the H2G side chain 4-hydroxy group with a bulky protecting group. In scheme B above this is depicted as t-butyldiphenylsilyl, but other regioselective protecting groups such as trityl, 9-(9-phenyl)xanthenyl, 1,1-bis(4-methylphenyl)-1'-pyrenylmethyl may also be appropriate. The resulting product is acylated at the side chain 2-hydroxymethyl group using analogous reagents and procedures as described in scheme A above, but wherein the activated acid derivative is the $R_2$ fatty acid, for example, myristic, stearic, oleic, elaidic acid chloride and the like. The thus monoacylated compounds are subjected to appropriate deprotection treatment to remove the side chain 4-hydroxy protecting group which can be done in a highly selective manner with such reagents, depending on the regioselective protecting group, as HF/pyridine and the like and manipulation of the reaction conditions, viz reagent concentration, speed of addition, temperature and solvent etc, as elaborated above. The then free side chain 4-hydroxy group is acylated with the activated α-amino acid in a similar way as described in scheme A above.

Additional techniques for introducing the amino acid ester of $R_1/R_2$, for instance in schemes A, B, C, D or E herein include the 2-oxa-4-aza-cycloalkane-1,3-dione method described in International patent application No. WO 94/29311.

Additional techniques for introducing the fatty acid ester of $R_1/R_2$, for instance in schemes A, B, C, D or E herein include the enzymatic route described in Preparative Biotransformations 1.11.8 (Ed S M Roberts, J Wiley and Son, NY, 1995) with a lipase such as SP 435 immobilized Candida antarcticus (Novo Nordisk), porcine pancreatic lipase or Candida rugosa lipase. Enzymatic acylation is especially convenient where it is desired to avoid N-protection and deprotection steps on the other acyl group or the purine 2-amine.

An alternative route to compounds of Formula I in which $R_3$ is hydrogen is to 6-activate the correponding guanine compound of Formula I (wherein the amino acid ester moiety of $R_1/R_2$ is optionally protected with conventional N-protecting groups such as BOC) with an activating group such as halo. The thus activated 6-purine is subsequently reduced to purine, for instance with a palladium catalyst and deprotected to the desired 6-deoxy H2G di-ester.

A further aspect of the invention thus provides a method for the preparation of the compounds of formula I comprising a) optionally N-protecting the purine 2 and/or 6 positions of a compound of formula I wherein $R_1$ and $R_2$ are each hydrogen;

b) regioselectively acylating the compound of Formula I at the side chain 4-hydroxy group with either
  i) an optionally N-protected valine or isoleucine group,
  ii) an optionally substituted, saturated or monounsaturated $C_3$–$C_{21}$COOH derivative, or
  iii) a regioselective protecting group;

c) acylating at the side chain 2-hydroxymethyl group with
  i) an optionally N-protected valine or isoleucine derivative, or
  ii) an optionally substituted, saturated or monounsaturated $C_3$–$C_{21}$COOH derivative;

d) replacing the regioselective protecting group at $R_1$, if present, with
  i) an optionally N-protected valine or isoleucine derivative; or
  ii) an optionally substituted, saturated or monounsaturated $C_3$–$C_{21}$COOH derivative; and e) deprotecting the resulting compound as necessary.

Schemes A and B above employ selective acylation to stepwise add the amino acid and fatty acid esters. An alternative process for the preparation of the compounds of formula I starts with a diacylated H2G derivative, wherein both the acyl groups are the same, and employs selective removal of one of the acyl groups to obtain a monoacyl intermediate which is then acylated with the second, differing, acyl group in the same manner as Schemes A and B above.

Accordingly a further aspect of the invention provides a method for the preparation of a compound of the formula 1, as defined above, which method comprises A) the monodeacylation of a diacylated compound corresponding to formula I wherein $R_1$ and $R_2$ are both a valyl or isoleucyl ester (which is optionally N-protected) or wherein $R_1$ and $R_2$ are both —C(=O)$C_3$–$C_{21}$ saturated or monounsaturated, optionally substituted alkyl; and B) acylating the thus liberated side chain 4-hydroxy or side chain 2-hydroxymethyl group with the corresponding valyl, isoleucyl or —C(=O)$C_3$–$C_{21}$ saturated or monounsaturated, optionally substituted alkyl; and C) deprotecting as necessary.

This alternative process has the advantage that the preparation of the diacylated H2G derivative is facile and requires little or no purification steps. Selective removal of one only of the acyl groups of a diacylated H2G derivative can be achieved by manipulating the reaction conditions, in particular the temperature, rate of reactant addition and choice of base.

Compounds amenable to this alternative synthesis route are thus of the formula:

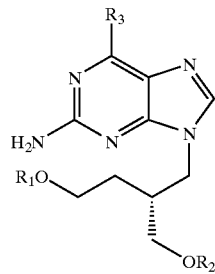

wherein $R_1$ and $R_2$ are valyl or isoleucyl (which are optionally N-protected) or a —C(=O)$C_3$–$C_{21}$ saturated or monounsaturated, optionally substituted alkyl; and $R_3$ is OH or H.

For ease of synthesis in this alternative route, it is preferred that $R_1$ and $R_2$ are both initially identical and are most preferably the same amino acid ester. Such a di-amino acid ester will generally be N-protected during its preparation and may be used directly in this condition in the selective deacylation step. Alternatively, such an N-protected di-aminoacylated H2G derivative may be deprotected and optionally reprotected, as described below. The unprotected di-aminoacyl H2G derivative thus comprises one of the following compounds:

(R)-9-[2-(L-isoleucyloxymethyl)-4-(L-isoleucyloxy)butyl] guanine,
(R)-9-[2-(L-valyloxymethyl)-4-(L-valyloxy)butyl]guanine,
(R)-2-amino-9-[4-(L-isoleucyloxy)-2-(L-isoleucyloxymethyl)butyl]purine, and
(R)-2-amino-9-[4-(L-valyloxy)-2-(L-valyloxymethyl)butyl]purine.

These unprotected H2G diacylated derivatives can be directly subject to selective deacylation of one of the acyl groups (typically the side chain 4-position acyl) followed by enzymatic acylation of the liberated 4-hydroxy as described above. Alternatively, the unprotected H2G diacylated derivative can be re-protected and then subjected to the selective deacylation, followed in turn by conventional acylation with the fatty acid ester, as described in Schemes A and B. Conveniently, such a reprotection step is done with a different N-protecting group, having properties appropriate to the subsequent acylation. For example, it is convenient to employ a lipophilic N-protecting group, such as Fmoc when preparing a di-amino acid H2G derivative, as the lipophilic nature of the protecting group assists with separation of the acylated products. On the other hand, the lipophilic nature of Fmoc is of less utility when conducting an acylation with a fatty acid, and thus it is convenient to reprotect a diacylated H2G with an alternative N-protecting group such as BOC.

It will also be apparent that the preparation of the compounds of formula I can commence with the novel monoacylated intermediates of step b i), ii) or iii) in the above defined first method aspect of the invention. These compounds are thus of the formula:

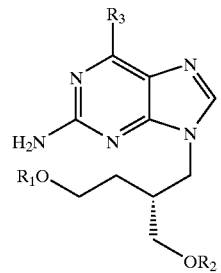

wherein one of $R_1$ and $R_2$ is
i) —C(O)CH(CH($CH_3$)$_2$)$NH_2$ or —C(O)CH(CH($CH_3$)$CH_2CH_3$)$NH_2$,
ii) a —C(=O)$C_3$–$C_{21}$ saturated or monounsaturated, optionally substituted alkyl, or
iii) a regioselective protecting group;
the other of $R_1$ and $R_2$ is hydrogen; and
$R_3$ is OH or H.

Useful compounds thus include:
(R)-9-[2-hydroxymethyl-4-(t-butyldiphenylsilyl)butyl] guanine,
(R)-9-[2-hydroxymethyl-4-(trityloxy)butyl]guanine,
(R)-9-[2-hydroxymethyl-4-(9-(9-phenyl)xanthenyloxy) butyl]guanine,
(R)-9-[2-hydroxymethyl-4-(11-bis(4-methylphenyl)-1'-pyrenylmethyloxy)butyl]guanine,
(R)-9-[2-hydroxymethyl-4-(decanoyloxy)butyl]guanine,
(R)-9-[2-hydroxymethyl)-4-(dodecanoyloxy)butyl]guanine,
(R)-9-[2-hydroxymethyl-4-(tetradecanoyloxy)butyl] guanine,
(R)-9-[2-hydroxymethyl)-4-(hexadecanoyloxy)butyl] guanine,
(R)-9-[2-hydroxymethyl-4-(octadecanoyloxy)butyl] guanine,
(R)-9-[2-hydroxymethyl)-4-(eicosanoyloxy)butyl]guanine,
(R)-9-[2-hydroxymethyl-4-(docosanoyloxy)butyl]guanine,
(R)-9-[4-hydroxy-2-(decanoyloxymethyl)butyl]guanine,
(R)-9-[4-hydroxy-2-(dodecanoyloxymethyl)butyl]guanine,
(R)-9-[4-hydroxy-2-(tetradecanoyloxymethyl)butyl] guanine,
(R)-9-[4-hydroxy-2-(hexadecanoyloxymethyl)butyl] guanine,
(R)-9-[4-hydroxy-2-(octadecanoyloxymethyl)butyl] guanine,
(R)-9-[4-hydroxy-2-(eicosanoyloxymethyl)butyl]guanine,
(R)-9-[4-hydroxy-2-(docosanoyloxymethyl)butyl]guanine,
(R)-9-[2-hydroxymethyl-4-(L-valyloxy)butyl]guanine,
(R)-9-[2-hydroxymethyl)-4-(L-isoleucyloxy)butyl]guanine,
(R)-9-[4-hydroxy-2-(L-isoleucyloxymethyl)butyl]guanine,
(R)-9-[4-hydroxy-2-(L-valyloxymethyl) butyl]guanine.

(R)-2-amino-9-[2-hydroxymethyl-4-(L-valyloxy)butyl] purine, (R)-2-amino-9-[2-hydroxymethyl)-4-(L-isoleucyloxy) butyl]purine, (R)-2-amino-9-[4-hydroxy-2-(L-isoleucyloxymethyl)butyl] purine, and (R)-2-amino-9-[4-hydroxy-2-(L-valyloxymethyl)butyl] purine.

Regioselectively protected, sidechain 4-hydroxy intermediates from step c) of the above described first method aspect of the invention are also novel compounds. Useful compounds thus include:

(R)-9-[2-decanoyloxymethyl-4-(t-butyldiphenylsilyl)butyl] guanine, (R)-9-[2-dodecanoyloxymethyl-4-(t-butyldiphenylsilyl) butyl]guanine, (R)-9-[2-tetradecanoyloxymethyl-4-(t-butyldiphenylsilyl) butyl]guanine, (R)-9-[2-hexadecanoyloxymethyl-4-(t-butyldiphenylchlorosilane)butyl]guanine, (R)-9-[2-octadecanoyloxymethyl-4-(t-butyldiphenylsilyl) butyl]guanine, (R)-9-[2-eicosanoyloxymethyl-4-(t-butyldiphenylsilyl) butyl]guanine, and (R)-9-[2-docosanoyloxymethyl-4-(t-butyldiphenylsilyl) butyl]guanine.

An alternative process for the preparation of compounds of the invention of the formula I wherein $R_3$ is —OH is shown in Scheme C.

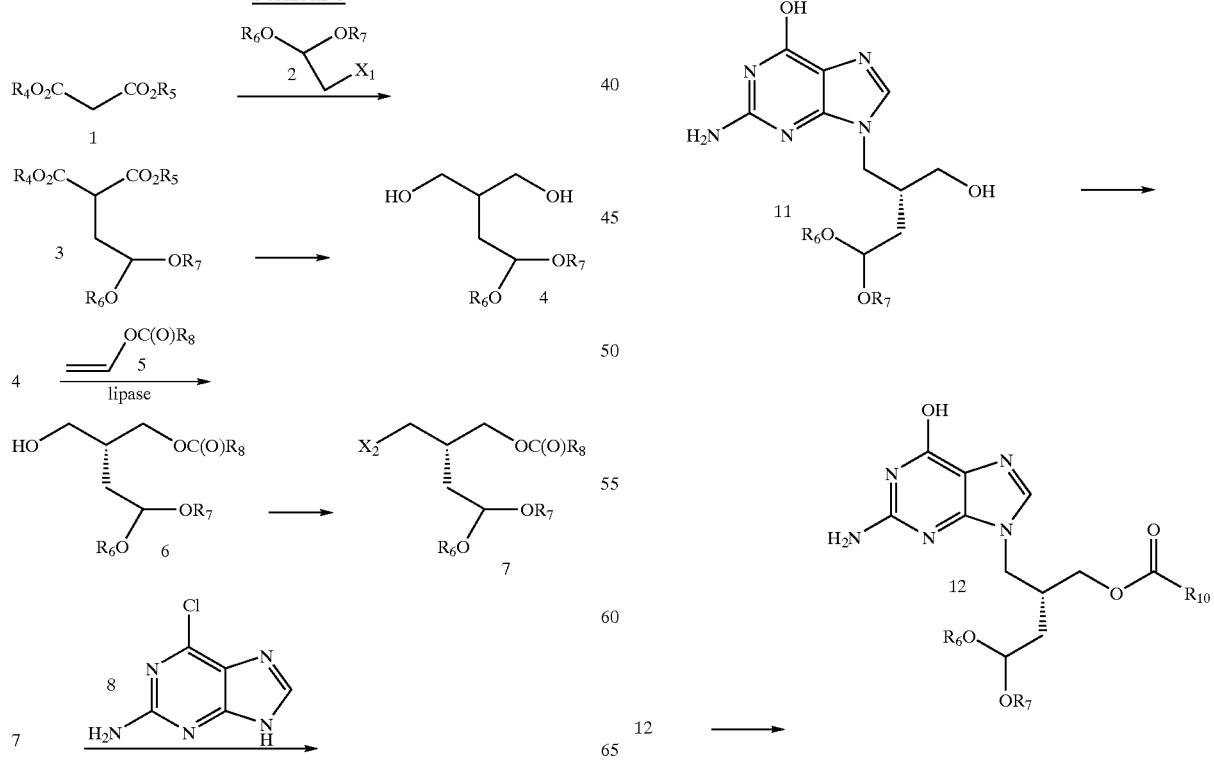

SCHEME C

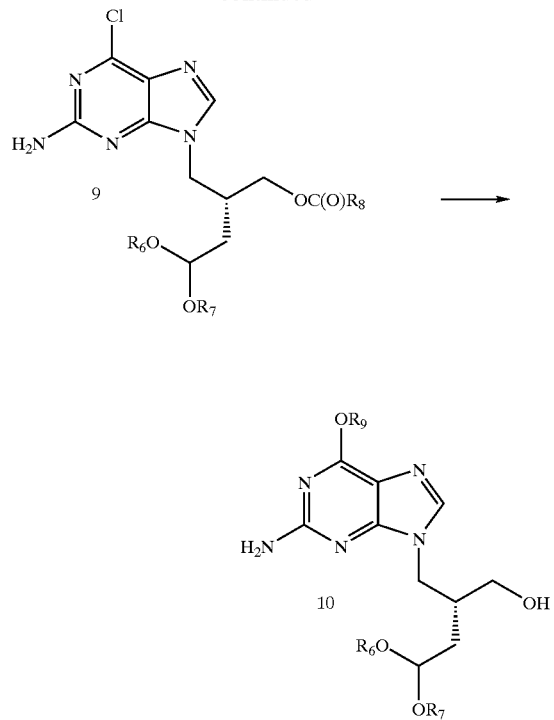

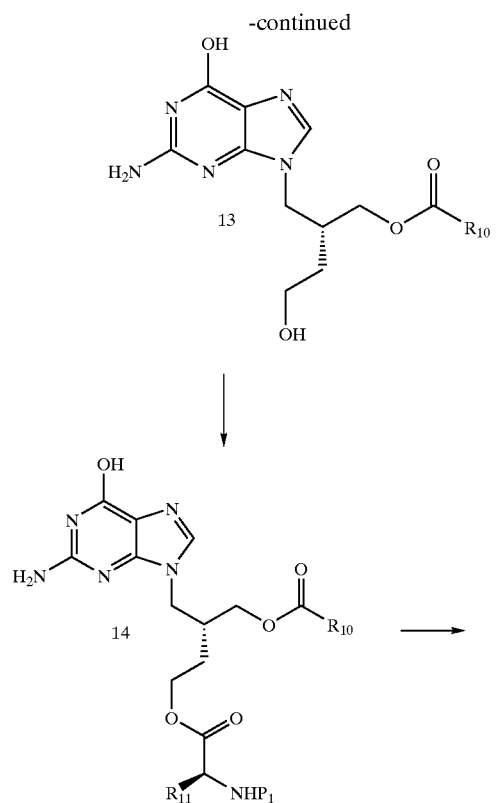

Referring to Scheme C, malonate 1 ($R_4$ and $R_5$ are lower alkyl or benzyl or the like) is alkylated by reaction with from about 0.5 to about 2.0 molar equivalents of acetal 2 ($R_6$ and $R_7$ are lower alkyl or benzyl and the like or $R_6$ and $R_7$ taken together are —CH$_2$CH$_2$— or —CH$_2$CH$_2$CH— or —CH$_2$CH$_2$CH$_2$CH$_2$— and $X_1$ is a leaving group (for example, Cl, Br or I, or a sulfonate such as methanesulfonate, triflate, p-toluenesulfonate, benzenesulfonate and the like)) in the presence of from about 0.5 to about 2.0 molar equivalents of a base (for example, potassium t-butoxide or sodium ethoxide or NaH or KH and the like) in an inert solvent (for example, DMF or THF or dioxane or dioxolane or N-methylpyrrolidone and the like) at a temperature of from about −40° C. to about 190° C. to provide alkylated malonate 3. Alkylated malonate 3 can be purified by distillation or by first treating the crude alkylated malonate with dilute aqueous base (for example, 7% aqueous KOH), followed by removal of volatile impurities by distillation.

Reduction of 3 with from about 0.5 to about 4.0 molar equivalents of an ester to alcohol reducing agent (for example, LiBH$_4$ or Ca(BH$_4$)$_2$ or NaBH$_4$ or LiAlH$_4$ and the like) in an inert solvent (for example, THF or methyl t-butyl ether or t-BuOH and the like) at a temperature of from about −20° C. to about 100° C. provides diol 4. Enzymatic esterification of 4 by reaction with from about 1.0 to about 20.0 molar equivalents of a vinyl ester 5 ($R_8$ is $C_{1-C21}$ saturated or monounsaturated, optionally substituted alkyl) in the presence of a lipase (for example, Lipase PS-30 or Lipase PPL or Lipase CCL and the like) or a phospholipase (for example phospholipase D and the like) provides the desired stereoisomer of ester 6. This reaction can be carried out in the absence of solvent or in the presence of an inert solvent (for example, methyl t-butyl ether or toluene or hexane and the like). The reaction is carried out at a temperature of from about −20° C. to about 80° C.

The alcohol substituent of 6 is converted to a leaving group (for example, a halogen or a sulfonate) by reaction with a halogenating agent (for example NBS/P(Ph)$_3$ or NCS/P(Ph)$_3$ or POCl$_3$ or NCS/P(Ph)$_3$/NaI in acetone and like) in an inert solvent (for example, methylene chloride or toluene or ethylacetate and the like) or by reaction with from about 0.8 molar equivalents to about 2.0 molar equivalents of a sulfonyl halide (for example, benzenesulfonylchloride, toluenesulfonylchloride or methane sulfonylchloride and the like) in the presence of from about 1.0 to about 4.0 molar equivalents of a base (for example, triethylamine or potassium carbonate or pyridine or dimethylaminopyridine or ethyldiisopropylamine and the like) in an inert solvent (for example methylene chloride or toluene or ethylacetate or pyridine or methyl t-butyl ether and the like) at a temperature of from about −25° C. to about 100° C. to provide ester 7 ($X_2$ is a halogen or sulfonate leaving group).

Reaction of 7 with from about 0.9 to about 2.0 molar equivalents of 2-amino-6-chloropurine 8 in the presence of from about 1.0 to about 6.0 molar equivalents of a base (for example, potassium carbonate or LiH or NaH or KH or NaOH or KOH or lithium diisopropylamide or LiN(Si(CH$_3$)$_3$)$_2$ and the like) in an inert solvent (for example, DMF or THF or acetonitrile or N-methylpyrrolidone or ethanol or DMSO and the like) at a temperature of from about −25° C. to about 140° C. provides substituted purine 9.

Alternatively, the base can be a sterically bulky amine base (for example, 1,8-diazabicyclo[5.4.0]undec-7-ene (DBU), 1,4-diazabicyclo[2.2.2]octane (Dabco), 1,5-diazabicyclo[4.3.0]non-5-ene (DBN), tetramethylguanidine, N,N-diisopropylethylamine and the like) or a sterically bulky phosphazine base (for example, tert-butylimino-tri (pyrrolidino)-phosphorane, tert-butylimino-tri (dimethylamino)phosphorane, tert-octylimino-tri (dimethylamino)phosphorane and the like) in an inert solvent (for example, THF or DMF or DMSO and the like).

Alternatively Mitsunobu coupling (for example P(Ph)$_3$/ diethyl azidocarboxylate) of alcohol 6 with 2-amino-6-chloropurine 8 provides 9.

Reaction of 9 with from about 2.0 to about 20 molar equivalents of an alcohol $R_9$OH ($R_9$ is an alcohol protecting group such as benzyl or diphenylmethyl and the like) in the presence of from about 1.0 to about 6.0 molar equivalents of a base (for example, potassium t-butoxide or potassium carbonate or NaH or KH or lithium diisopropylamide and the like) in an inert solvent (for example, THF or DMF and the like) at a temperature of from about −25° C. to about 150° C. provides alcohol 10.

Removal of the alcohol protecting group $R_9$ of 10 (for example, by catalytic hydrogenation in an inert solvent such as ethanol or benzyl alcohol or methanol or THF and the like in the presence of an hydrogenation catalyst such as Pd/C or Pd(OH)$_2$ and the like) provides substituted guanine 11.

Esterification of 11 by reaction with a) from about 0.8 to about 2.0 molar equivalents of $R_{10}$COOH and a coupling agent (for example DCC/DMAP) and the like in an inert solvent (for example THF or DMF and the like) or b) from about 0.8 to about 2.0 molar equivalents of an activated derivative of $R_{10}$COOH (for example, the acid chloride or N-hydroxysuccinimide ester or $R_{10}$C(O)OS(O)$_2$R$_{30}$ ($R_{30}$ is loweralkyl, phenyl or toluyl) or $R_{10}$C(O)OC(O)$R_{10}$ or $R_{10}$C (O)OC(O)$R_{10a}$ ($R_{10a}$ is loweralkyl and the like) in the presence of from about 0 to about 3.0 molar equivalents of a base (for example, pyridine or dimethylaminopyridine or triethylamine or ethyldiisopropylamine or N-methylmorpholine or DBU or potassium carbonate and the like) in an inert solvent (for example, methylene chloride or THF or pyridine or acetonitrile or DMF and the like) at a temperature of from about −25° C. to about 100° C. provides ester 12. $R_{10}$ is $C_3$–$C_{21}$ saturated or monounsaturated, optionally substituted alkyl.

The acetal substituent of 12 is deprotected and the resulting aldehyde is reduced by first reacting 12 with from about 0.1 to about 10.0 molar equivalents of an acid (for example, triflic acid or HCl or formic acid or acetic acid/formic acid or sulfuric acid and the like) in an inert solvent (for example, THF/$H_2O$ or methylene chloride/$H_2O$ or ethylacetate/$H_2O$ or ethanol/$H_2O$ or methanol/$H_2O$ or water and the like) at a temperature of from about −25° C. to about 100° C. To the crude reaction mixture is added from about 0.1 to about 10.0 molar equivalents of a base (for example, sodium bicarbonate or potassium carbonate or triethylamine or pyridine or KOH and the like), (optionally, additional inert solvent (for example, THF and or methylene chloride or ethylacetate or methyl t-butyl ether or isopropoanol and the like) is added) and from about 0.3 to about 5.0 molar equivalents of an aldehyde reducing agent (for example, sodium borohydride or RaNi/$H_2$ or borane t-butylamine complex and the like) at a temperature of from about −25° C. to about 100° C. to provide alcohol 13. The optical purity of compound 13 can be enhanced by reaction with optically active oraganic sulfonic acids such as (S)-(+)-camphorsulfonic acid and the like. A preferred sulfonic acid for this purpose is (S)-(+)-camphorsulfonic acid.

Alternatively, the acetal substituent of 12 can be hydrolyzed by reaction in an inert solvent with an acid resin (for example, Amberlyst 15 resin, Nafion NR50 resin, Dowex 50WX4-200R resin or Amerlite 120 resin and the like) to provide the corresponding aldehyde. The aldehyde can be isolated prior to reduction to the alcohol 13 as described above or the crude aldehyde can be reduced directly in situ.

Reaction of 13 with from about 0.8 to about 3.0 molar equivalents of N-protected amino acid $P_1NHCH(R_{11})COOH$ or an activated derivative thereof ($P_1$ is an N-protecting group (for example, benzyloxycarbonyl, t-butyloxycarbonyl, allyloxycarbonyl and the like) and $R_{11}$ is isopropyl or isobutyl) in an inert solvent (for example, THF or dioxane or dioxolane or DMF or methylene chloride and the like) at a temperature of from about 25° C. to about 100° C. provides alcohol 14.

N-deprotection of 14 provides the compound of the invention of formula I wherein $R_3$ is —OH. For example, when the protecting group can be removed by hydrogenation, such as when the protecting group is Cbz, hydrogenation in the presence of Pd/C in ethanol or Pd/BaCO$_3$ or Pd/BaSO$_4$ and the like in THF or isopropanol/THF and the like is preferred.

Alternatively, compound 13 can be reacted with the symmetrical anhydride derived from $P_1NHCH(R_{11})COOH$ (i.e., $P_1NHCH(R_{11})C(O)O—C(O)CH(R_{11})NHP_1$) to provide 14. The anhydride can be prepared in situ or can be separately prepared prior to reaction with 13.

Alternatively, 11 can be prepared by hydrolysis of the ester of 9 to an alcohol (for example, by reaction with a base such as $K_2CO_3$, $Li_2CO_3$, $Na_2CO_3$, KHCO$_3$, LiOH, NaOH or KOH and the like in an inert solvent such as methanol, ethanol, isopropanol, THF, water or mixtures thereof and the like, most prefereably with $K_2CO_3$ in MeOH/$H_2O$ and the like), followed by direct conversion of the chloro group to an —OH (for example, by reaction with an inorganic base such as KOH or NaOH and the like in $H_2O$ with heating and the like).

In another alternative method, 11 can be prepared directly by hydrolysis of the chloro-ester 9 (for example, by reaction with an inorganic base such as KOH or NaOH and the like in $H_2O$ with heating and the like).

In another alternative, the ester of 9 can be hydrolyzed by an esterase in water or an aqueous buffer, with or without the presence of an added organic solvent such as an alcohol (for example, ethanol or isopropanol and the like), THF, DMF or DMSO and the like.

In another alternative method, 11 can be prepared from 9 (or from the hydroxy compound resulting from the hydrolysis of the ester in 9) by reaction with an inorganic base (for example, NaOH, LiOH, KOH and the like, preferably, NaOH) and trimethylamine in an aqueous solvent.

In yet another alternative method, 11 can be prepared directly by hydrolysis of the chloro-ester 9 (for example, by reaction with 1–3 equivalents of a base such as sodium methoxide (and the like) in the presence of mercaptoethanol in a mixed solvent of water and methanol or dioxane (and the like) at a temperature of from about 20° C. to about relfux and the like).

In yet another alternative method, prior to conversion of 9 to 10 or 11, the ester of 9 can be hydrolyzed to the alcohol as described above. The alcohol can then be reesterified and purified (for example, from methyl t-butyl ether and the like). This process leads to an increase in the enantiomeric excess (i.e., purity) of the resulting ester 9. Preferably, the alcohol is reesterified to provide the acetate, which is purified from methyl t-butyl ether.

In yet another alternative method, 13 can be prepared by reaction of 9 (wherein $R_8$=$R_{10}$) with formic acid, optionally with heating, followed by reduction of the aldehyde to give 13.

In yet another alternative, 13 can be prepared from 11 without isolation of intermediates and with in situ generation of the esterification agent, thus increasing purity of the resulting product and allowing increased throughput in the process.

Another alternative process for the preparation of compounds of Formula I wherein $R_3$ is —OH is shown in Scheme D.

SCHEME D

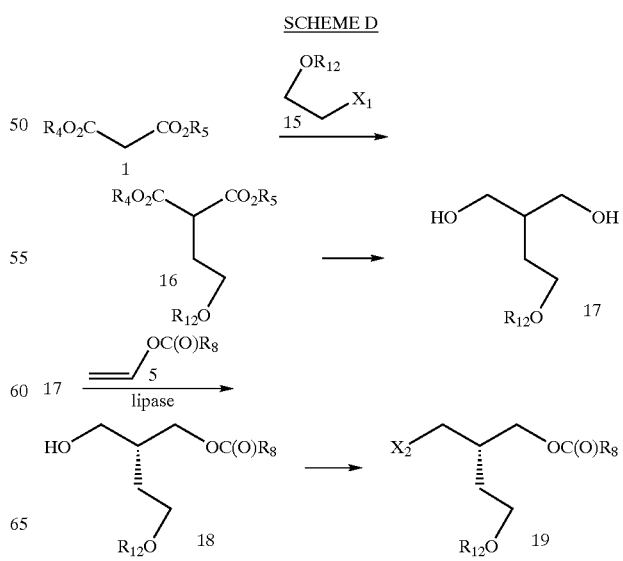

23

-continued

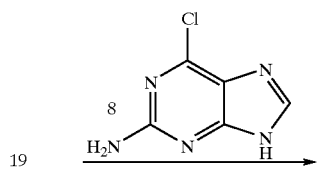

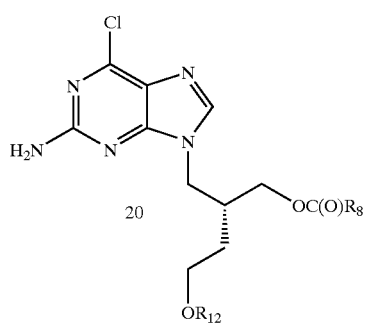

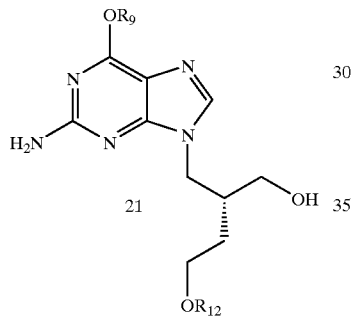

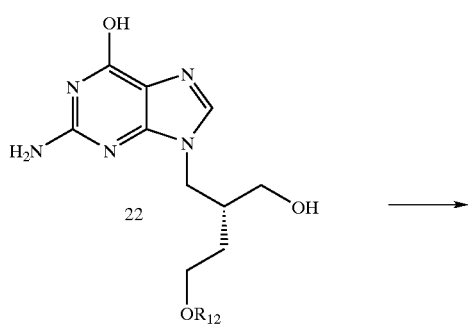

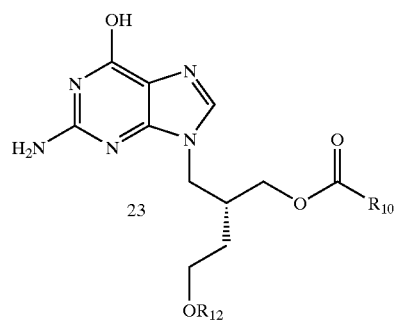

24

-continued

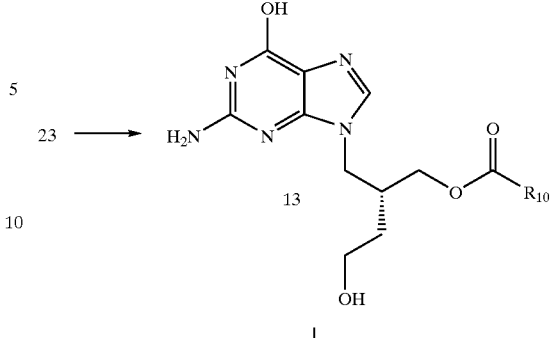

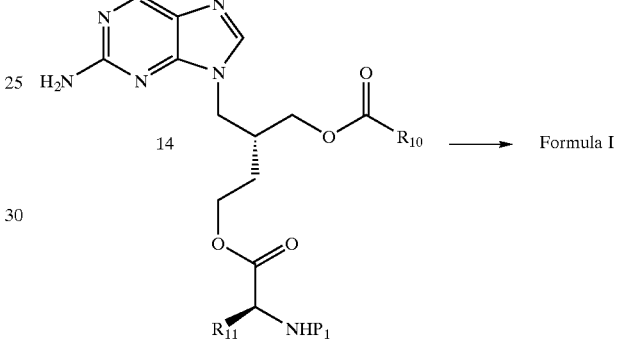

Malonate 1 ($R_4$ and $R_5$ are lower alkyl or benzyl and the like) is alkylated with from about 0.5 to about 2.0 molar equivalents of ether 15 wherein X, is a leaving group (for example Cl, Br or I, or a sulfonate such as methane sulfonate, triflate, p-toluenesulfonate, benzenesulfonate and the like) and $R_{12}$ is —CH(Ph)$_2$, —C(Ph)$_3$ or —Si(t-Bu)(Me)$_2$ and the like (Ph=phenyl) in the presence of from about 0.5 to about 2.0 molar equivalents of a base (for example potassium t-butoxide or sodium ethoxide or NaH or KH and the like) in an inert solvent (for example DMF or THF or dioxane or dioxolane or N-methyl pyrrolidinone and the like) at a temperature of from about −40° C. to about 190° C. to provide alkylated malonate 16.

Reduction of 16 with from about 0.5 to about 4.0 molar equivalents of an ester to alcohol reducing agent (for example LiBH$_4$ or Ca(BH$_4$)$_2$ or NaBH$_4$ or LiAlH$_4$ and the like) in an inert solvent (for example, THF or methyl t-butyl ether or ethanol or t-butanol and the like) at a temperature of from about −20° C. to about 100° C. provides diol 17. Enzymatic esterification of 17 by reaction with from about 1.0 to about 20.0 molar equivalents of a vinyl ester 5 ($R_8$ is $C_1$–$C_{21}$ saturated or monounsaturated, optionally substituted alkyl) in the presence of a lipase (for example, Lipase PS-30 or Lipase PPL or Lipase CCL and the like) or a phospholipase (for example phospholipase D and the like) provides the desired stereoisomer of ester 18. The reaction can be carried out in the absence of solvent or in the presence of an inert solvent (for example methyl t-butyl ether or toluene or hexane or the like). The reaction is carried out at a temperature of from about −20° C. to about 80° C.

The alcohol substituent of 18 is converted to a leaving group (for example a halogen or sulfonate) by reaction with a halogenating agent (for example $NBS/P(Ph)_3$ or $NCS/P(Ph)_3$ or $POCl_3$ or $NCS/P(Ph)_3/NaI$ in acetone and the like) in an inert solvent (for example methylene chloride or toluene or ethylacetate and the like) or by reaction with from about 0.8 molar equivalents to about 2.0 molar equivalents of a sulfonyl halide (for example benzenesulfonylchloride, toluenesulfonylchloride or methane sulfonylchloride and the like) in the presence of from about 1.0 to about 4.0 molar equivalents of a base (for example triethylamine or potassium carbonate or pyridine and the like) in an inert solvent (for example, methylene chloride or toluene or ethyl acetate or methyl t-butyl ether and the like) at a temperature of from about −25° C. to about 100° C. to provide ester 19 ($X_2$ is a halogen or sulfonate leaving group).

Reaction of 19 with from about 0.9 to about 2.0 molar equivalents of 2-amino-4-chloropurine 8 in the presence of from about 1.0 to about 6.0 molar equivalents of a base (for example potassium carbonate or LiH or NaH or KH or NaOH or KOH or lithium diisopropylamide or $LiN(Si(CH_3)_3)_2$ and the like) in an inert solvent (for example DMF or THF or acetonitrile or N-methylpyrrolidone or ethanol and the like) at a temperature of from about −25° C. to about 140° C. provides substituted purine 20.

Alternatively, Mitsunobu coupling (for example, $P(PH)_3$/diethyl azidocarboxylate) of alcohol 18 with 2-amino-4-chloropurine 8 provides 20.

Reaction of 20 with from about 2.0 to about 20.0 molar equivalents of an alcohol $R_9OH$ ($R_9$ is an alcohol protecting group such as benzyl or diphenylmethyl and the like) in the presence of from about 1.0 to about 6.0 molar equivalents of a base (for example, potassium t-butoxide or potassium carbonate or NaH or KH or lithium diisopropylamide and the like in an inert solvent (for example, THF or DMF and the like) at a temperature of from about −25° C. to about 150° C. provides alcohol 21.

Removal of the alcohol protecting group $R_9$ of 21 (for example by catalytic hydrogenation in an inert solvent such as ethanol or benzyl alcohol or methanol or THF and the like in the presence of an hydrogenation catalyst such as Pd/C or $Pd(OH)_2$ and the like) provides substituted guanine 22, which can be esterified as described in Scheme C (i.e., 11 to 12) to provide 23.

The ether substitutent of 23 is deprotected by reaction with a) a reducing agent (for example, $HCO_2H$ and Pd/C and the like) wherein $R_{12}$ is —$CH(Ph)_2$ or —$C(Ph)_3$, or b) a desilylating agent (for example $Bu_4NF$ and the like) wherein $R_{12}$ is —$Si(t-Bu)(Me)_2$ and the like to provide 13.

Alcohol 13 can be converted to I as outlined in Scheme C.

Alternatively, 22 can be prepared by hydrolysis of the ester of 20 to an alcohol (for example, by reaction with $K_2CO_3$ in $MeOH/H_2O$ and the like), followed by direct conversion of the chloro group to an —OH (for example, by reaction with KOH in $H_2O$ with heating and the like).

In another alternative method, 22 can be prepared directly by hydrolysis of the chloro-ester 20 (for example, by reaction with KOH in $H_2O$ with heating and the like).

In another alternative method, 22 can be prepared from 20 (or from the hydroxy compound resulting from the hydrolysis of the ester in 20) by reaction with an inorganic base (for example, NaOH, LiOH, KOH and the like, preferably, NaOH) and trimethylamine in an aqueous solvent.

In yet another alternative method, 22 can be prepared directly by hydrolysis of the chloro-ester 20 (for example, by reaction with 1–3 equivalents of a base such as sodium methoxide (and the like) in the presence of mercaptoethanol in a mixed solvent of water and methanol or dioxane (and the like) at a temperature of from about 20° C. to about relfux and the like).

In yet another alternative method, 23 can be prepared by reaction of 20 (wherein $R_8$=$R_{10}$) with formic acid, optionally with heating, followed by reduction of the aldehyde to give 23.

An additional alternative involves enzymatic esterification of alcohol 4 or 17 with the vinyl ester $CH_2$=CH—OC(O)$R_{10}$ (i.e., $R_8$=$R_{10}$ in Schemes C and D) to directly incorporate into 6 or 18 the desired carboxylic acid ester of the final product I. This allows the elimination of the ester hydrolysis and reesterification involved in going from 9 to 12 or from 20 to 23.

The processes of Schemes C and D are characterized by the fact that each of the hydroxyl groups of the acyclic side chain is differentiated by the use of different hydroxy protecting groups or precursor groups. This allows the selective acylation of each of the hydroxy groups with either an amino acid or a fatty acid group.

Schemes C and D have been illustrated and described with reference to embodiments of the invention wherein $R_1$ is derived from an amino acid and $R_2$ is derived from a fatty acid. However, it will be apparent that respective converse schemes will apply to compounds where $R_1$ is derived from a fatty acid and $R_2$ is derived from an amino acid.

SCHEME E

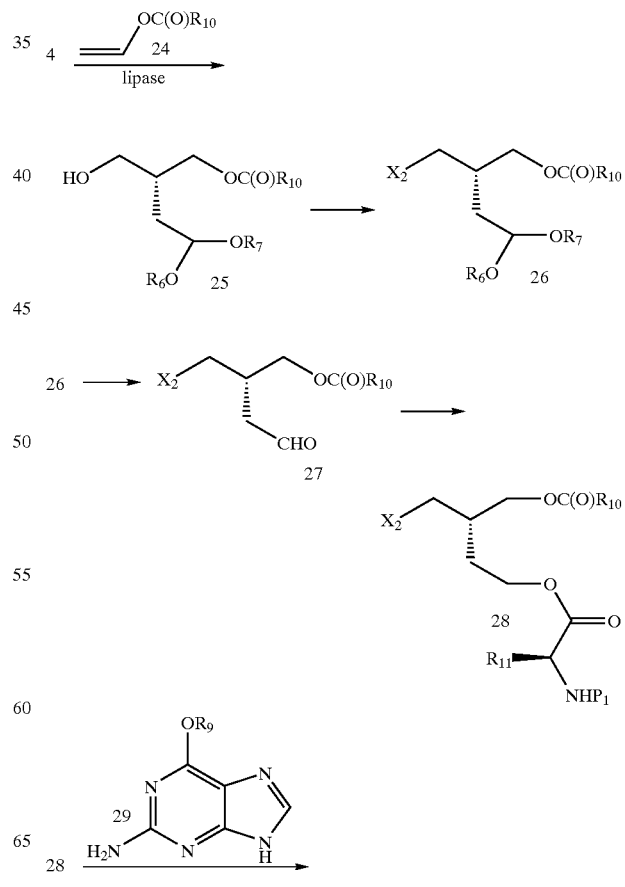

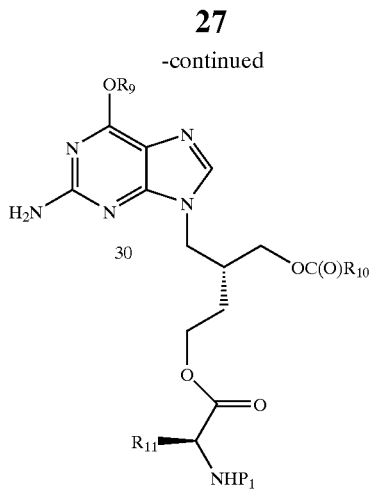

Yet another method for preparing compounds of Formula I is shown in Scheme E. Enzymatic esterification of 4 (see Scheme C) by reaction with from about 1.0 to about 20.0 molar equivalents of a vinyl ester 24 ($R_{10}$ is $C_3$–$C_{21}$ saturated or monounsaturated, optionally substituted alkyl) in the presence of a lipase (for example, Lipase PS-30 or Lipase PPL or Lipase CCL and the like) or a phospholipase (for example phospholipase D and the like) provides the desired stereoisomer of ester 25. This reaction can be carried out in the absence of solvent or in the presence of an inert solvent (for example, methyl t-butyl ether or toluene or hexane and the like). The reaction is carried out at a temperature of from about −20° C. to about 80° C.

The alcohol substituent of 25 is converted to a leaving group (for example, a halogen or a sulfonate) by reaction with a halogenating agent (for example NBS/P(Ph)$_3$ or NCS/P(Ph)$_3$ or POCl$_3$ or NCS/P(Ph)$_3$/NaI in acetone and like) in an inert solvent (for example, methylene chloride or toluene or ethylacetate and the like) or by reaction with from about 0.8 molar equivalents to about 2.0 molar equivalents of a sulfonyl halide (for example, benzenesulfonylchloride, toluenesulfonylchloride or methane sulfonylchloride and the like) in the presence of from about 1.0 to about 4.0 molar equivalents of a base (for example, triethylamine or potassium carbonate or pyridine or dimethylaminopyridine or ethyldiisopropylamine and the like) in an inert solvent (for example methylene chloride or toluene or ethylacetate or pyridine or methyl t-butyl ether and the like) at a temperature of from about −25° C. to about 100° C. to provide ester 26 ($X_2$ is a halogen or sulfonate leaving group).

The acetal substituent of 26 is hydrolyzed to the aldehyde 27 by reacting 26 with an acid (for example, trifluoroacetic acid, triflic acid or HCl or formic acid or acetic acid/formic acid or sulfuric acid and the like) in an inert solvent (for example, THF/H$_2$O or methylene chloride/H$_2$O or ethylacetate/H$_2$O or ethanol/H$_2$O or methanol/H$_2$O or water and the like) at a temperature of from about −25° C. to about 100° C.

To the aldehyde 27 in an inert solvent (for example, THF and or methylene chloride or ethylacetate or methyl t-butyl ether or isopropoanol and the like) is added an aldehyde to alcohol reducing agent (for example, sodium borohydride or RaNi/H$_2$ or borane t-butylamine complex and the like) at a temperature of from about −25° C. to about 100° C. to provide the corresponding alcohol.

Reaction of the resulting alcohol with from about 0.8 to about 3.0 molar equivalents of N-protected amino acid P$_1$NHCH(R$_{11}$)COOH or an activated derivative thereof (P$_1$ is an N-protecting group (for example, benzyloxycarbonyl, t-butyloxycarbonyl, allyloxycarbonyl, trichloroethylcarbonyl and the like) and R$_{11}$ is isopropyl or isobutyl) in an inert solvent (for example, THF or dioxane or dioxolane or DMF or methylene chloride and the like) at a temperature of from about 25° C. to about 100° C. provides diester 28.

Alternatively the alcohol can be reacted with the symmetrical anhydride derived from P$_1$NHCH(R$_{11}$)COOH (i.e., P$_1$NHCH(R$_{11}$)C(O)O—C(O)CH(R$_{11}$)NHP$_1$) to provide 28.

Conversion of 27 to 28 can be accomplished with or without isolation/purification of the intermediate alcohol. A preferred aldehyde to alcohol reducing agent is borane t-butylamine complex. A preferred esterification agent is the symmetrical anhydride.

Reaction of 28 with purine 29 in the presence of a base (for example potassium carbonate or LiH or NaH or KH or NaOH or KOH or lithium diisopropylamide or LiN(Si(CH$_3$)$_3$)$_2$ and the like) in an inert solvent (for example, DMF and the like) provides 30. Purine 29 is prepared from 6-chloro-2-amino purine by reaction with R$_9$OH in an inert solvent (for example, toluene or THF and the like) in the presence of a base (for example, NaH or KH or NaOH or KOH or potassium t-butoxide and the like). A preferred process for the the preparation of purine 29 involves reaction of 2-amino-6-chloropurine with neat R$_9$—OH in the presence of a base such as NaOH or KOH or potassium t-butoxide and the like. Substituted purine 30 is deprotected to provide the compound of Formula I.

Alternatively, in the reaction of 28 with 29, the base can be a sterically bulky amine base (for example, 1,8-diazabicyclo[5.4.0]-undec-7-ene (DBU), 1,4-diazabicyclo[2.2.2]octane (Dabco), 1,5-diazabicyclo[4.3.0]non-5-ene (DBN), tetramethylguanidine, N,N-diisopropylethylamine and the like) or a sterically bulky phosphazine base (for example, tert-butylimino-tri(pyrrolidino)-phosphorane, tert-butylimino-tri(dimethylamino)phosphorane, tert-octylimino-tri(dimethylamino)phosphorane and the like) in an inert solvent (for example, THF or DMF or DMSO and the like).

SCHEME F

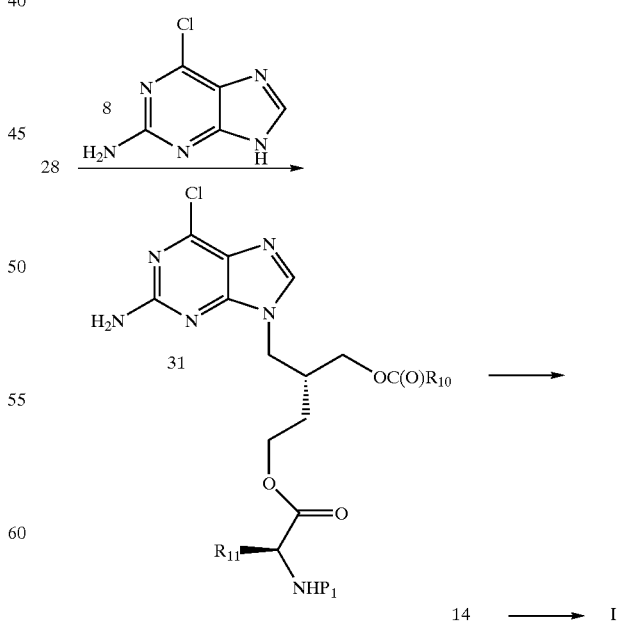

Yet another method for preparing compounds of Formula I is shown in Scheme F. Reaction of 28 with aminochloropurine 8 in the presence of a base (for example potassium carbonate or LiH or NaH or KH or NaOH or KOH or lithium diisopropylamide or LiN(Si(CH$_3$)$_3$)$_2$ and the like) in an inert solvent (for example, DMF THF and the like) provides 31. Hydrolysis of 31 to 14 can be accomplished under basic or acidic conditions (for example, with trimethlyamine or DABCO or KOH or LiOH or NaOH and the like in water/THF or methylene chloride and the like or with acetic acid and the like).

Alternatively, 8 can be be alkylated with 28 using a sterically bulky amine base (for example, 1,8-diazabicyclo [5.4.0]undec-7-ene (DBU), 1,4-diazabicyclo[2.2.2]octane (Dabco), 1,5-diazabicyclo[4.3.0]non-5-ene (DBN), tetramethylguanidine, N,N-diisopropylethylamine and the like) or a sterically bulky phosphazine base (for example, tert-butylimino-tri(pyrrolidino)-phosphorane, tert-butylimino-tri(dimethylamino)phosphorane, tert-octylimino-tri(dimethylamino)phosphorane and the like) in an inert solvent (for example, THF or DMF or DMSO and the like).

In each of Schemes C, D and F, the 2-amino-6-chloropurine (8) can be replaced with 2-amino-6-iodo-purine or 2-amino-6-bromopurine, which can be alkylated and then transformed to the substituted guanine in a manner analogous to that disclosed for alkylation and transformation of 8.

SCHEME G

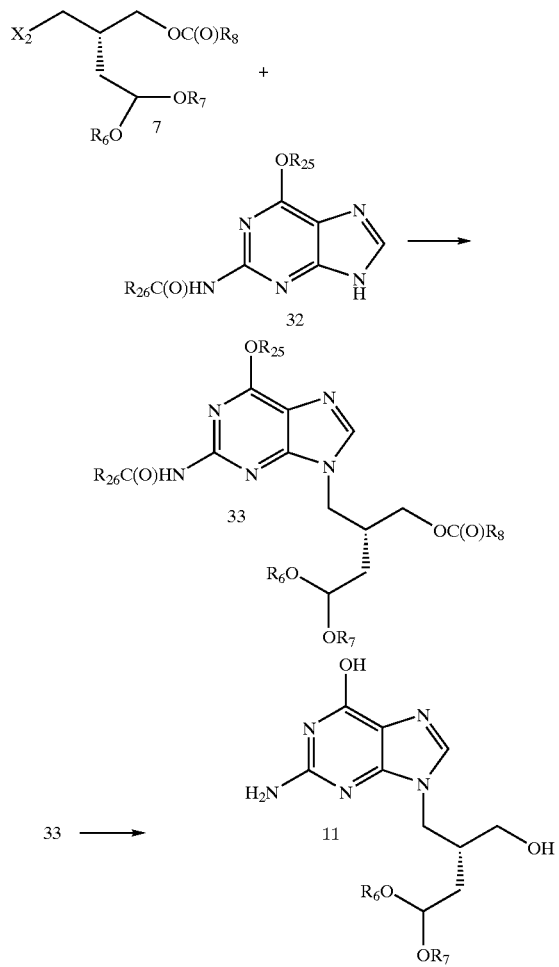

Yet another method for preparing the compounds of formula I is shown in Scheme G. Alkylation of 32 with 7 in the presence of a base (for example, potassium carbonate, LiH, NaH and the like) in an inert solvent (for example, DMF THF and the like) provides 33. $R_{25}$ is hydrogen or —C(O)NR$_{27}$R$_{28}$ wherein R$_{27}$ and R$_{28}$ are independently selected from loweralkyl, phenyl and benzyl or R$_{27}$ and R$_{28}$, taken together with the nitrogen to which they are attached, form a pyrrolidinyl group or a piperidinyl group. $R_{26}$ is loweralkyl, phenyl or benzyl.

Hydrolysis of 33 to 11 can be accomplished under basic conditions (for example, with KOH in water and the like).

Alternatively, 32 can be alkylated with 7 using a sterically bulky amine base (for example, 1,8-diazabicyclo[5.4.0] undec-7-ene (DBU), 1,4-diazabicyclo[2.2.2]octane (Dabco), 1,5-diazabicyclo[4.3.0]non-5-ene (DBN), tetramethylguanidine, N,N-diisopropylethylamine and the like) or a sterically bulky phosphazine base (for example, tert-butylimino-tri(pyrrolidino)-phosphorane, tert-butylimino-tri(dimethylamino)phosphorane, tert-octylimino-tri(dimethylamino)phosphorane and the like) in an inert solvent (for example, THF or DMF or DMSO and the like).

DETAILED DESCRIPTION OF THE INVENTION

The invention will now be illustrated by way of example only with reference to the following non-limiting Examples, and comparative examples.

EXAMPLE 1

(R)-9-[2-(Stearoyloxymethyl)-4-(L-valyloxy)butyl] guanine

This example illustrates the application of preparation scheme A.

a) (R)-9-[4-(N-tert-Butoxycarbonyl-L-valyloxy)-2-(hydroxymethyl)butyl]guanine.

H2G (5 g, 19.7 mmol) was dissolved in DMF (300 ml) under heating and was cooled to room temperature before addition of N-t-Boc-L-valine (5.58 g, 25.7 mmol), DMAP (0.314 g, 2.57 mmol) and DCC (6.52 g, 31.6 mmol). The mixture was stirred at room temperature for 24 h and was then filtered. The product was chromatographed on silica gel and eluted with CH$_2$Cl$_2$/MeOH to give 2.4 g of the desired intermediate product.

$^1$H-NMR (250 MHz, DMSO-d$_6$): δ 0.95 (d, 6H), 1.47 (s, 9H), 1.5–1.8 (m, 2H), 1.96–2.20 (m, 2H), 3.40 (m, 2H), 3.91 (t, 1H), 4.05 (m, 2H), 4.21 (t, 2H), 4.89 (t, 1H), 6.6 (br s, 2H), 7.27 (d, 1H), 7.75 (s, 1H), 10.7 (br s,1H).

b) (R)-9-[4-(N-tert-Butoxycarbonyl-L-valyloxy)-2-(stearoyloxymethyl)butyl]guanine.

The product from step a) (185 mg, 0.41 mmol) was dissolved in pyridine (5 ml), the solution was cooled in an ice bath and stearoyl chloride (179 μl, 0.531 mmol) was added. The solution was kept in the ice bath for 2 h, then at room temperature for 1 h. It was then evaporated and chromatographed on silica gel. It was eluted with dichloromethane/methanol to give 143 mg of the desired intermediate product.

c) (R)-9-[2-(Stearoyloxymethyl)-4-(L-valyloxy)butyl] guanine.

The product from step b) (138 mg, 0.192 mmol) was cooled in an ice bath and trifluoroacetic acid (5 ml) was added. The solution was kept in the ice bath for 45 minutes and was then evaporated to give an oil. Water (0.5 to 1 ml) was added and evaporated twice. The residue was once more dissolved in water (5 ml), filtered and freeze-dried to give 148 mg of the desired product as the bistrifluoracetate salt.

$^1$H NMR (250 MHz, DMSO-d$_6$): δ 0.97 (t, 3H), 1.05 (dd, 6H), 1.34 (br s, 28 H), 1.59 (m, 2H), 1.80 (m, 2H), 2.25 (m, 1H), 2.36 (t, 2H), 2.50 (m, 1H), 3.98–4.18 (m, 5H), 4.35 (t, 2H), 6.6 (br s, 2H), 8.0 (br s,1H), 8.4 (br s, 3H), 10.9 (br s, 1 H).

EXAMPLE 2

(R)-9-[2-(Myristoyloxymethyl)-4-(L-valyloxy)butyl]guanine

The titled compound was obtained as the bistrifluoracetate salt in a manner analogous to Example 1 using myristoyl chloride instead of stearoyl chloride in step b).
$^1$H NMR (250 MHz, DMSO-d$_6$): δ 0.97 (t, 3H), 1.05 (dd, 6H), 1.34 (br s, 20H), 1.57 (m, 2H), 1.78 (m, 2H), 2.24 (m, 1H), 2.35 (t, 2H), 2.51 (m, 1H), 3.97–4.20 (m, 5H), 4.36 (t, 2H), 6.8 (br s, 2H), 8.2 (br s, 1H), 8.5 (br s, 3H), 11.1 (br s,1H).

EXAMPLE 3

(R)-9-[2-(Oleoyloxymethyl)-4-(L-valyloxy)butyl]guanine

The titled compound was obtained as the bistrifluoroacetyl salt in a manner analogous to Example 1 using oleoyl chloride instead of stearoyl chloride in step b).
$^1$H NMR (250 MHz, DMSO-d$_6$): δ 0.96 (t, 3H), 1.05 (dd, 6H), 1.35 (br s, 20H), 1.59 (m, 2H), 1.76 (m, 2H), 2.09 (m, 4H), 2.24 (m, 1H), 2.35 (t, 2H), 2.50 (m, 1H), 3.97–4.17 (m, 5H), 4.35 (t, 2H), 5.43 (t, 2H), 6.7 (br s, 2H), 8.0 (br s, 1H), 8.5 (br s, 3H), 11.1 (brs, 1H).

EXAMPLE 4

(R)-9-[2-(Butyryloxymethyl)-4-(L-valyloxy)butyl]guanine a) (R)-9-[4-(N-tert-Butoxycarbonyl-L-valyloxy)-2-(butyryloxymethyl)butyl]guanine.

DCC (110 mg, 0.53 mmol) was dissolved in dichloromethane (10 ml) and butyric acid (82 mg, 0.93 mmol) was added. After 4 hours at room temperature the mixture was filtered and the filtrate was evaporated. The residue was dissolved in pyridine (5 ml) and (R)-9-[4-(N-tert-Butoxycarbonyl-L-valyloxy)-2-hydroxymethylbutyl]guanine (200 mg, 0.44 mmol) (Example 1, step a) was added. The mixture was stirred for 120 hours at room temperature. According to TLC the reaction was incomplete and more anhydride was made using the procedure above. This anhydride was added and the mixture was stirred for an additional 20 hours. The reaction mixture was evaporated and chromatographed first on silica gel and then on aluminium oxide, in both cases eluted with dichloromethane/methanol to give 79 mg of the intermediate product.

b) (R)-9-[2-(Butyryloxymethyl)-4-(L-valyloxy)butyl]guanine.

The intermediate product of step a was deprotected in a manner analogous to Example 1, step c to give 84 mg of the desired product as the bistrifluoracetate salt.
$^1$H NMR (250 MHz, D$_2$O): δ 0.88 (t, 3H), 1.06 (dd, 6H), 1.53 (m, 2H), 1.93 (q, 2H), 2.25 (t, 2H), 2.36 (m,1H), 2.60 (m,1H), 4.06 (d,1H), 4.14–4.30 (m, 2H), 4.43 (m, 4H), 8.99 (br s, 1H).

EXAMPLE 5

(R)-9-[2-(Decanoyloxymethyl)-4-(L-valyloxy)butyl]guanine

The titled compound was obtained as the bistrifluoroacetate salt in a manner analogous to Example 1 using decanoyl chloride instead of stearoyl chloride in step b.
$^1$H NMR (250 MHz, D$_2$O): (0.90 (m, 3H), 1.01 (d, 6H), 1.28 (br s, 12H), 1.5 (m, 2H), 1.8 (m, 2H), 2.3 (m, 3H), 2.5 (m, 1H), 4.0–4.4 (m, 7H), 8.1 (br s, 1H).

EXAMPLE 6

(R)-9-[2-Docosanoyloxymethyl-4-(L-valyloxy)butyl]guanine

The titled compound was obtained as the bistrifluoroacetate salt in a manner analogous to Example 1 but using in step b the DMAP/DCC conditions of Example 1, step a) in conjunction with docosanoic acid in place of the stearoyl chloride and a mixture of DMF and dichloromethane as solvent.
$^1$H NMR (250 MHz, DMSO-d$_6$): δ 0.97 (t, 3H), 1.05 (dd, 6H), 1.34 (br s, 36 H), 1.58 (m, 2H), 1.77 (m, 2H), 2.24 (m, 1H), 2.35 (t, 2H), 2.50 (m, 1H), 3.97–4.17 (m, 5H), 4.35 (t, 2H), 6.7 (br s, 2H), 8.1 (br s, 1H), 8.4 (br s, 3H), 11.0 (br s, 1H).

EXAMPLE 7

R-9-(4-(L-Isoleucyloxy)-2-(stearoyloxymethyl)butyl (guanine

This example illustrates the application of preparative scheme B.

a) (R)-9-[2-hydroxymethyl 4-(t-butyldiphenylsilyloxy)butyl]guanine.

H2G (2 g, 8 mmole) was coevaporated with dry DMF two times and was then suspended in dry DMF (120 ml) and pyridine (1 ml). To the suspension was added dropwise t-butyldiphenylchlorosilane (2.1 ml, 8.2 mmole) in dichloromethane (20 ml) at 0 (C over a period of 30 min. The reaction mixture became a clear solution at the completion of the dropwise addition. The reaction continued at 0° C. for two hours and was then kept at 4° C. overnight. Methanol (5 ml) was added to the reaction. After 20 min at room temperature, the reaction mixture was evaporated to a small volume, poured into aqueous sodium hydrogen carbonate solution and extracted with dichloromethane two times. The organic phase was dried over sodium sulphate and evaporated in vacuo. The product was isolated by silica gel column chromatography using a methanol/dichloromethane system with a stepwise increasing MeOH concentration . The product was eluted with 7% MeOH in CH$_2$Cl$_2$ to yield 1.89 g.

b) (R)-9-[2-(Stearoyloxymethyl)-4-(t-butyldiphenylsilyloxy)butyl]guanine.

(R)-9-[2-Hydroxymethyl 4-(t-butyldiphenylsilyloxy)butyl]guanine (2.31 g, 5 mmole) was coevaporated with dry pyridine twice and dissolved in pyridine (20 ml). To the solution was slowly added dropwise stearoyl chloride (1.86 ml, 5.5 mmole, technical grade) in dichloromethane (2 ml) at −5° C. The reaction was kept at the same temperature for 1 hr and then at 5° C. for 2 hr. The reaction was monitored by TLC. Additional stearoyl chloride (0.29 ml) at −5° C. was added due to incompletion of reaction. After 30 min at 5° C., methanol (3 ml) was added and the reaction mixture stirred for 20 min. It was then poured into aqueous sodium hydrogen carbonate solution, and extracted with dichloromethane. The organic phase was dried and the product purified by silica gel column chromatography with stepwise increasing MeOH, eluting with 3.5% MeOH in CH$_2$Cl$_2$. (Yield 2.7 g).

c) (R)-9-[(4-Hydroxy-2-(stearoyloxymethyl)butyl]guanine.

(R)-9-[2-(Stearoyloxymethyl)-4-(t-butyldiphenylsilyloxy)butyl]guanine (2.7 g, 3.56 mmole) was dissolved in dry THF (30 ml) and hydrogen fluoride-pyridine (1.5 ml) added to the solution. The reaction was kept at 4° C. overnight and monitored by TLC. The reaction reached about 80% conversion. Additional HF-pyridine was added (0.75 ml). After 4 hr, TLC showed that the starting material had disappeared. The reaction mixture was concentrated in vacuo without raising the temperature and more pyridine (5 ml) was added and evaporated again. The product was isolated by silica gel column chromatography. (Yield 1.26 g).

d) (R)-9-[4-(N-BOC-L-isoleucyloxy)-2-(stearoyloxymethyl)butyl]guanine.

(R)-9-(4-Hydroxy-2-(stearoyloxymethyl)butyl(guanine (135 mg, 0.26 mmole) and N-BOC-L-isoleucine (180 mg, 0.78 mmole) were coevaporated with dry DMF twice and dissolved in the same solvent (3.5 ml). To the solution was added 1,3-dicyclohexylcarbodiimide (160 mg, 0.78 mmole) and 4-dimethylaminopyridine (4.8 mg, 0.039 mmole). After reaction for 18 hours, the reaction mixture was filtered through Celite and worked up in a conventional manner. The product was isolated by silica gel column chromatography, eluting at 5% MeOH in $CH_2Cl_2$. (Yield 160 mg)

e) (R)-9-[4-(L-Isoleucyloxy)-2-(stearoyloxymethyl)-butyl]guanine.

(R)-9-[4-(N-BOC-L-isoleucyloxy)-2-(stearoyloxymethyl)butyl]guanine (150 mg, 0.205 mmole) from step d) was treated with trifluoroacetic acid (3 ml) at 0° C. for 20 min. The solution was evaporated in vacuo. The residue was coevaporated with toluene twice and kept under vacuum for several hours. The residue was dissolved in MeOH (2 ml) and evaporated to give the trifluoracetate salt as a glass-like product. (Yield 191 mg).

$^1$H NMR (DMSO-$d_6$+$D_2O$): δ 8.35 (s,1H, base), 4.21 (t, 2H, H-4), 4.10 (d, 2H) 3.96 (d, 2H), 3.90 (d, 1H, isoleucine), 2.48 (m, 1H, H-2), 2.15 (2H, stearoyl), 1.85 (m, 1H, isoleucine), 1.68 (m, 2H), 1.48 (m, 4H), 1.68 (m, 28H), 0.81 (m, 9H).

EXAMPLE 8

(R)-9-[2-(Decanoyloxymethyl)-4-(L-isoleucyloxy)butyl]guanine

The title compound was obtained as the bistrifluoroacetate salt in a manner analogous to Example 7 using decanoyl chloride instead of stearoyl chloride in step b).

$^1$H NMR (DMSO-$d_6$): δ 11.1 (s, 1H, NH), 8.35 (s, br, 3H), 8.28 (s, 1H, base), 6.75 (s, 2H, NH2 ), 4.23 (t, 2H), 4.07 (d, 2H), 4.05 (m, 3H), 2.4 (m, 1H), 2.21 (t, 2H), 1.83 (m, 1H), 1.66 (m, 2H), 1.45 (m, 2H), 1.39 (m, 2H), 1.22 (s, 12H ), 0.84 (m, 9H).

EXAMPLE 9

(R)-9-[4-(L-Isoleucyloxy)-2-(myristoyloxymethyl)butyl]guanine

The title compound was obtained as the bistrifluoroacetyl salt in a manner analogous to Example 1 using N-BOC-L-isoleucine instead of N-BOC-valine in step a) and myristoyl chloride instead of stearoyl chloride in step b).

$^1$H-NMR (DMSO-$d_6$): δ 10.99 (s, 1H), 8.34 (br s, 3H) 8.15 (s, 1H ), 6.67 (br s, 2H), 4.23 (t, 2H), 4.05 (d, 2H), 3.97 (m, 3H), 2.48 (m, 1H), 2.20 (t, 2H), 1.85 (m, 1H), 1.65 (m, 2H), 1.41 (m, 4H), 1.23 (s, 20H), 0.85 (m, 9H).

EXAMPLE 10

(R)-9-[2-(4-Acetylbutyryloxymethyl-4-(L-valyloxy)butyl]guanine

The titled compound was obtained as the bistrifluoroacetate salt in a manner analogous to Example 1 but using in step b) the DCC/DMAP conditions of Example 1, step a) in conjunction with 4-acetylbutyric acid instead of stearoyl chloride.

$^1$H-NMR (250 MHz, DMSO-$d_6$): δ 1.05 (dd, 6H), 1.77 (m, 4H), 2.19 (s, 3H), 2.24 (m, 1H), 2.36 (t, 2H), 2.44–2.60 (m, 3H), 3.95–4.20 (m, 5H), 4.36 (m, 2H), 6.8 (br s, 2H), 8.3 (br s, 1H), 8.5 (br s, 3H), 11.1 (br s, 1H).

EXAMPLE 11

(R)-9-[2-Dodecanoyloxymethyl-4-(L-valyloxy)butyl]guanine

The titled compound was obtained as the bistriflouroacetate salt in a manner analogous to Example 1 using dodecanoyl chloride instead of stearoyl chloride in step b).

EXAMPLE 12

(R)-9-[2-Palmitoyloxymethyl-4-(L-valyloxy)butyl]guanine

The titled compound was obtained as the bistriflouroacetate salt in a manner analogous to Example 1 using palmitoyl chloride instead of stearoyl chloride in step b).

$^1$H-NMR (250 MHz, DMSO-$d_6$): δ 0.97 (t, 3H), 1.05 (m, 6H), 1.35 (br s, 24H), 1.58 (m, 2H), 1.78 (m, 2H), 2.25 (m, 1H), 2.35 (t, 2H), 2.51 (m, 1H), 3.97–4.18 (m, 5H), 4.35 (t, 2H), 6.7 (br s, 2H), 8.1 (br s, 1H), 8.5 (br s, 3H), 11.0 (br s, 1H).

EXAMPLE 13

(R)-2-Amino-9-(2-stearoyloxymethyl-4-(L-valyloxy)butyl)purine

This example shows the deoxygenation of group $R_1$.

a) (R)-2-Amino-9-(2-stearoyloxymethyl-4-(N-tert-butoxycarbonyl-L-valyloxy)butyl)-6-chloropurine:

To a solution of (R)-9-(2-stearoyloxymethyl-4-(N-tert-butoxycarbonyl-L-valyloxy)butyl)guanine from step b of Example 1 (646 mg, 0.9 mmole) in acetonitrile were added tetramethylammonium chloride (427 mg, 2.7 mmole), N,N-diethylaniline (0.716 ml, 4.5 mmole) and phosphorous oxychloride (0.417 ml, 4.5 mmole). The reaction was kept under reflux and the progression monitored by TLC. After 3 hours the reaction mixture was evaporated in vacuo and the residue was dissolved in dichloromethane, then poured into cold sodium hydrogen carbonate aqueous solution. The organic phase was evaporated and purified by silica gel column chromatography. Yield: 251 mg.

$^1$H-NMR (CDCl$_3$): δ 7.76 (1H, H-8), 5.43 (br,2H, NH2), 4.45–4.00 (m, 7H), 2.53 (m, 1H), 2.28 (t 2H), 2.12 (m, 1H), 1.75 (m, 2H), 1.59 (m, 2H), 1.43 (9H), 1.25 (m, 28H), 0.96 (d, 3H), 0.87 (m, 6H).

b) (R)-2-Amino-9-(2-stearoyloxmethyl-4-(N-tert-butoxycarbonyl-L-valyloxy)butyl)purine To the solution of (R)-2-amino-9-(2-stearoyloxymethyl-4-(N-tert-butoxycarbonyl-L-valyloxy)butyl)-6-chloropurine (240 mg, 0.33 mmole) in methanol/ethyl acetate (6 ml, 3:1 v/v) were added ammonium formate (105 mg, 1.65 mmole) and 10% palladium on carbon (15 mg). The reaction was kept under reflux for 1 hour and recharged with ammonium formate (70 mg). After one hour more the TLC showed completion of the reaction and the mixture was filtered through Celite and washed extensively with ethanol. The filtrate was evaporated and purified by silica gel column. Yield: 193 mg.

$^1$H-NMR (CDCl$_3$): δ 8.69 (s,1H, H-6), 7.74 (s, 1H, H-8), 5.18 (br, s, 2H, NH2), 4.45–4.01 (m, 7H), 2.55 (m, 1H), 2.28 (t, 2H), 2.10 (m, 1H), 1.75 (m, 2H), 1.60 (m, 2H), 1.43 (s, 9H), 1.25 (s, 28H), 0.96 (d, 3H), 0.87 (m, 6H).

c) (R)-2-Amino-9-(2-stearoyloxymethyl-4-(L-valyloxy) butyl)purine:

(R)-2-Amino-9-(2-Stearoyloxymethyl-4-(N-tert-butoxycarbonyl-L-valyloxy)butyl)purine (180 mg, 0.26 mmole) was treated with trifluoroacetic acid (5 ml) at 0° C. for 40 min. It was then evaporated in vacuo and coevaporated successively with toluene and methanol. The residue was freeze-dried overnight to give 195 mg of the desired product.

¹H-NMR (DMSO-d₆): δ 8.78 (s, 1H, H-6), 8.32 (br, 3H), 8.29 (s, 1H, H-8), 4.27 (t, 2H), 4.13 (d, 2H), 3.98 (t, 2H, 2H), 3.89 (m, 1H), 2.47 (m,1H), 2.18 (m, 3H), 1.43 (m, 2H), 1.23 (28H), 0.93 (m, 6H), 0.85 (t, 3H).

EXAMPLE 14

Alternative preparation of (R)-9-[4-Hydroxy-2-(stearoyloxymethyl )butyl]guanine a) Preparation of ethyl 4,4-diethoxy-2-ethoxycarbonyl-butyrate

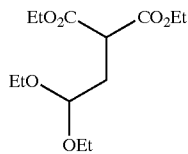

Potassium tert-butoxide (141.8 g, 1.11 equiv.) was dissolved in dry DMF (1 L). Diethyl malonate (266 mL, 1.54 equiv.) was added over 5 minutes. Bromoacetaldehyde diethylacetal (172 mL, 1.14 mole) was added over 5 minutes. The mixture was heated to 120° C. (internal temperature), and stirred at 120° C. for 5 hours. The mixture was allowed to cool to room temperature, poured into water (5 L), and extracted with methyl tert-butyl ether (MTBE, 3×600 mL). The organic solution was dried over MgSO₄, filtered, concentrated, and distilled (0.5 mm, 95–140° C.) to yield the desired diester (244 g, 78%) as a colorless oil.

¹H NMR (CDCl₃) δ 1.19 (t, 6H), 1.28 (t, 6H), 2.22 (dd, 2H), 3.49 (m, 2H), 3.51 (t, 1H), 3.65 (m, 2H) 4.20 (qd, 4H), 4.54 (t, 1H).

b) Preparation of 4,4-diethoxy-2-(hydroxymethyl)-butanol

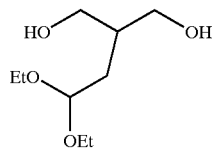

LiBH₄ (purchased solution, 2M in THF, 22.5 mL) and the product of Example 14 step a) (5 g in 15 mL of THF, 18.1 mmol) were combined and warmed to 60° C. and stirred at 60° C. for 4 hours. The reaction mixture was allowed to cool to room temperature and the reaction vessel was placed in a cool water bath. Then triethanolamine (5.97 mL, 1 equiv.) was added at such a rate that the temperature of the reaction mixture was maintained between 20–25° C. Brine (17.5 mL) was added at a rate such that gas evolution was controlled and the mixture was stirred for 45 minutes at room temperature. The layers were separated, the organic layer was washed with brine (2×15 mL). The combined brine washes were extracted with MTBE (methyl tert-butyl ether, 3×20 mL). The combined organic extracts were evaporated and the residue was dissolved in MTBE (50 mL) and washed with brine (25 mL). The brine layer was back-extracted with MTBE (3×25 mL). The combined organic extracts were dried over Na₂SO₄, filtered, and concentrated to yield the desired diol (3.36 g, 15.5 mmol, 97%) as a colorless oil.

¹H NMR (CDCl₃) δ 1.22 (t, 6H), 1.73 (dd, 2H), 1.92 (m, 1H), 2.67 (bs, 2H), 3.52 (m, 2H), 3.69 (m, 2H), 3.72 (m, 4H), 4.62 (t, 1H).

c) Preparation of (2R)-2-acetoxymethyl-4,4-diethoxy-butanol

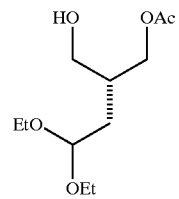

Into a 10 ml 1 neck round bottom flask was charged the product of Example 14 step b) (3.84 g, 20 mmol), followed by addition of vinyl acetate (2.6 g, 30 mmol) and finally Lipase PS 30 (69 mg, purchased from Amano, Lombard, Ill.). The mixture was allowed to stir at ambient temperature for 16 hours. Progress of the reaction was closely monitored by TLC (2/1 hexane-EtOAc; stained with Ce₂(SO₄)₃ and charred on hot plate; r.f. of diol is 0.1, monoacetate is 0.3, bis acetate is 0.75). The reaction mixture was diluted with CH₂Cl₂ and filtered through a 5 micron filter. The filter was washed with additional CH₂Cl₂. The filtrate was then concentrated in vacuo to afford the desired product.

d) Preparation of (2S)-2-acetoxymethyl-4,4-diethoxybutyl toluenesulfonate

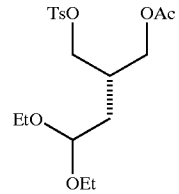

Into a 100 mL 1-neck round bottom flask, equipped with a magnetic stir bar and septum under N₂ was charged the crude product of Example 14 step c) (4.62 g, 19 mmol), dry CH₂Cl₂ (20 mL) and Et₃N (5.62 mL, 40 mmol). To this solution was added tosyl chloride (4.76 g, 25 mmol). The resulting mixture was stirred at ambient temperature for 4 hours. Charged H₂O (0.27 g, 15 mmol) and stirred vigorously for 4 hours. The reaction mixture was diluted with 80 mL EtOAc and 50 mL H₂O and the aqueous layer was separated. To the organic layer was added 75 ml of a 5% aq. solution of KH₂PO₄. After mixing and separation of the layers, the aqueous layer was removed. The organic layer was washed with 50 mL of saturated NaHCO₃ solution, dried over Na₂SO₄, filtered and concentrated in vacuo to a constant weight of 7.40 g of the desired product.

¹H NMR (CDCl₃) δ 1.17 (t, 6H); 1.62 (m, 2H); 1.94 (s, 3H); 2.19 (m, 1H); 2.45 (s, 3H); 3.42 (m, 2H); 3.6 (m, 2H); 4.03 (m, 4H); 4.51 (t, 1H); 7.36 (d, 2H); 7.79 (d, 2H).

e) Preparation of

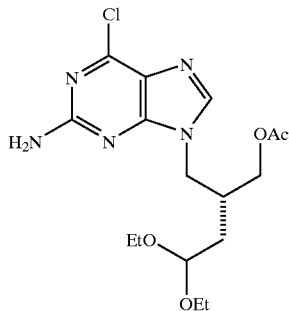

Into a 50 mL 1 neck round bottom flask was charged the product of Example 14 step d) (3.88 g, 10 mmol), anhydrous DMF (20 mL), 2-amino-4-chloro-purine (2.125 g, 12.5 mmol) and $K_2CO_3$ (4.83 g). The resulting suspension was stirred at 40° C. under a $N_2$ blanket for 20 hours. The mixture was concentrated to remove most of the DMF on a rotary evaporator. The residue was diluted with EtOAc (50 mL) and $H_2O$ (50 mL). The reaction mixture was transferred to a separatory funnel, shaken and the aqueous layer was separated. The aqueous layer was extracted with EtOAc (25 mL). The organic layers were combined and washed with 5% $KH_2PO_4$ (75 mL). The organic layer was separated and washed with $H_2O$ (75 mL), brine (75 mL), dried over $Na_2SO_4$, filtered and concentrated in vacuo to afford 3.95 g of crude product. The crude product was slurried with 40 mL of methyl-t-butyl ether. This mixture was stirred overnight at 4° C. and the mixture was filtered. The filtrate was concentrated to afford 3.35 g of the product as an oil (containing 2.6 g of the desired product based upon HPLC analysis).

300 MHz $^1$H NMR (CDCl$_3$) δ 1.19 (m, 6H); 1.69 (2H); 1.79 (s, 1H); 2.03 (s, 3H); 2.52 (m, 1H); 3.48 (m, 2H); 3.62 (m, 2H); 4.04 (m, 2H); 4.16 (m, 2H); 4.61 (t, 1H); 5.12 (bs, 2H); 7.81 (s,1H).

f) Preparation of

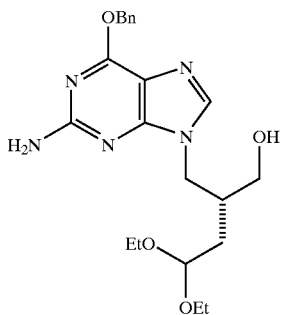

(Bn = benzyl)

Into a 500 mL 1 neck round bottom flask was charged benzyl alcohol (136 mL), cooled to 0° C., followed by portionwise addition of KO-t-Bu (36 g, 321 mmol). The temperature was allowed to warm to 40° C., and the mixture was stirred 20 minutes. To this mixture was added at 0° C. the crude product of Example 14 step e) (24.7 g, 64.2 mmol) dissolved in 25 mL anhydrous THF and benzyl alcohol (30 mL). The temperature was allowed to slowly warm to 8° C. over 2 hours. The reaction mixture was poured into 500 mL ice and was extracted with 500 mL MTBE. The organic layer was washed with 250 mL of brine, dried over $Na_2SO_4$, filtered and concentrated in vacuo to afford 193 g of a benzyl alcohol solution of the desired product. HPLC analysis indicated that the solution contained 25.96 g of the desired product.

300 MHz $^1$H NMR (CDCl$_3$) δ 1.22 (m,6H); 1.55 (2H); 2.18 (m, 1H); 3.15 (m, 1H); 3.40 (m, 1H); 3.51 (m, 2H); 3.70 (m, 2H); 4.25 (m, 2H); 4.63 (t,1H); 4.90 (bs, 2H); 5.25 (m, 1H); 5.58 (s, 2H); 7.35 (m, 3H); 7.51 (m, 2H); 7.72 (s, 1H). MS=(M+H)$^+$=416 (Cl).

g) Preparation of

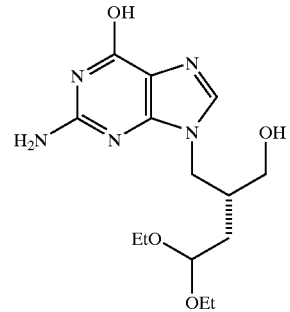

Into a 100 mL 1 neck round bottom flask was charged the crude product of Example 14 step f) (9.65 g of the benzyl alcohol solution, containing 1.30 g, 3.13 mmol of the product of Example 14, step f) dissolved in absolute EtOH (20 mL). To this was added 0.45 g of 10% Pd/C slurried in 5 mL absolute EtOH. The reaction flask was evacuated and charged with $H_2$ three times with a balloon of $H_2$. The reaction flask was pressurized with 1 atm. $H_2$ and the reaction mixture was stirred overnight. The reaction mixture was filtered through a pad of diatomaceous earth to remove Pd/C. The volatiles were removed in vacuo. The residue was mixed with 25 mL of isopropyl acetate and then concentrated in vacuo. The residue was diluted with EtOAc (10 mL), seeded with the desired product, heated to reflux and then CH$_3$CN (2 mL) and MTBE (35 ml) were added. The mixture was stirred for 30 minutes. The precipitate was filtered and dried to a constant weight of 600 mg of the desired product.

300 MHz $^1$H NMR (d$_6$-DMSO) δ 1.16 (m,6H); 1.45 (m, 1H); 1.61 (m, 1H); 2.16 (m, 1H); 3.45 (m, 2H); 3.40 (m, 1H); 3.62 (m, 2H); 4.02 (m,2 H); 4.53 (t, 1H); 4.85 (t, 1H); 6.55 (bs, 1H); 7.75 (s, 1H). MS=(M+H)$^+$=416 (Cl).

h) Preparation of

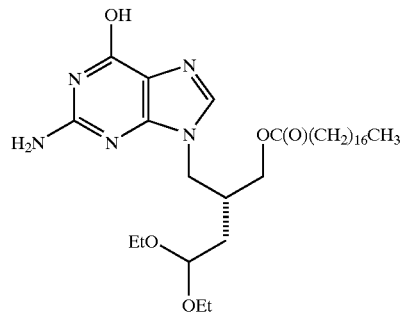

Into a 25 mL 1 neck round bottom flask was charged the product of Example 14 step g) (0.650 g, 2.0 mmol), pyridine (4 mL) and CH$_2$Cl$_2$ (2 mL), DMAP (10 mg). The mixture was cooled to -5° C. and stearoyl chloride (790 mg, 2.6 mmol) dissolved in CH$_2$Cl$_2$ (0.5 mL) was added over 5 minutes. The resulting mixture was stirred 16 hours at -5° C. Absolute EtOH (0.138 g, 3.0 mmol) was added and the mixture was stirred an additional 1 hour. The reaction mixture was concentrated in vacuo. Toluene (30 mL) was added to the residue and then the mixture was concentrated in vacuo. Again, toluene (30 mL) was added to the residue and then the mixture was concentrated in vacuo. To the residue was added 1% $KH_2PO_4$ (25 mL) and this mixture was extracted with $CH_2Cl_2$ (60 mL). The organic layer was separated and was dried over $Na_2SO_4$, filtered and concentrated in vacuo to a constant weight of 1.65 g. The crude product was chromatographed on 40 g of $SiO_2$, eluting with 95/5 $CH_2Cl_2$-EtOH, affording 367 mg of the desired product.

300 MHz $^1$H NMR (CDCl$_3$) δ 0.89 (t, 3H); 1.26 (m, 30 H); 1.65 (m,3 H); 2.32 (m, 1H); 3.45 (m, 1 H); 3.60 (m, 2H); 4.08 (m, 2H); 4.60 (m, 1 H); 6.0 (bs, 2H); 7.53 (s, 1 H).

i) Preparation of

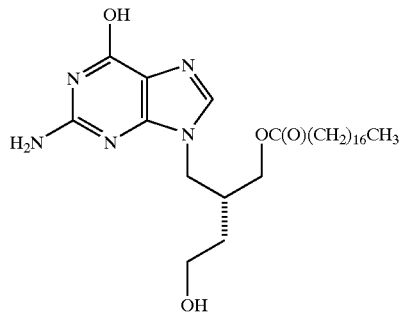

Into a 25 mL 1 neck round bottom flask was charged the product of Example 14, step h) (0.234 g, 0.394 mmol) dissolved in THF (1.7 mL). To this solution was added triflic acid (0.108 g) in $H_2O$ 180 mg. The mixture was stirred overnight at room temperature. To the reaction mixture was added saturated $NaHCO_3$ solution (10 mL), THF (5 mL), $CH_2Cl_2$ (2 mL) and $NaBH_4$ (0.10 g). This mixture was stirred for 30 minutes. To the reaction mixture was added a 5% solution of $KH_2PO_4$ (30 mL). This mixture was extracted with 2×15 ml of $CH_2Cl_2$. The organic layers were combined and dried over $Na_2SO_4$, filtered and concentrated in vacuo to a constant weight of 207 mg. This material was recrystallized from EtOAc (8 mL) and $CH_3CN$ (0.5 mL) affording 173 mg of the desired product.

300 MHz $^1$H NMR (d$_6$-DMSO) δ 0.82 (t, 3H); 1.19 (m, 30H); 1.41 (m, 4H); 2.19 (t, 2H); 2.32 (m, 1H); 3.40 (m, 2H); 3.9 (m, 4H); 4.49 (m,1H); 6.4 (bs, 2H); 7.61 (m, 1.5H); 9.55 (m, 0.5H).

EXAMPLE 15

Alternative Preparation of (R)-9-[4-(N-tert-butyloxycarbonyl-L-valyloxy)-2-(stearoyloxymethyl)butyl]guanine (R)-9-[2-(Stearoyloxymethyl)-4-(t-butyldiphenylsilyloxy)butyl]guanine (45 g) and THF (950 ml) were combined in a 2L flask. Then Boc-L-valine (3.22 g, 0.25 eq) was added, followed by tetrabutylammonium fluoride (1M in THF, 89.05 mL) over 10 minutes. The clear reaction mixture was stirred at room temperature for 2 hours and 50 minutes with monitoring of the reaction progress by TLC (90/10 $CH_2Cl_2$/MeOH).

To the reaction mixture was added Boc-L-valine (35.43 g, 2.75 eq), DCC (36.67 g, 2.75 eq) and dimethylaminopyridine (1.1 g, 0.15 eq) in THF (25 ml). The reaction mixture was stirred at room temperature for 24 hours. DCU was filtered off and washed with $CH_2Cl_2$. The filtrate was concentrated, and the residue was taken up in 2 liters of $CH_2Cl_2$ and washed with 2L of ½ saturated sodium bicarbonate and brine solutions. On drying and evaporation, approximately 100 g of crude product was obtained. The material was purified by silica chromatography (6000 ml of silica) using 3% MeOH/$CH_2Cl_2$ to 5% MeOH/$CH_2Cl_2$ to obtain 38.22 mg of the desired product.

EXAMPLE 16

Alternative preparation of (R)-9-[2-(stearoyloxymethyl)-4-(L-valyloxy)butyl]guanine a) (R)-9-[2-Hydroxymethyl)-4-(t-butyldiphenylsilyloxymethyl)butyl]guanine H2G (450.0 g, 1.78 mol) and N,N dimethylformamide (6.4 kg) were charged into a Bucchi evaporator and the mixture warmed to dissolve the solid. The solution was concentrated to dryness under vauum at no more than 90° C. The resulting powder was transferred to a 22 liter flask with stirrer, addition funnel and and temperature probe. N,N-dimethylformamide (1.7 kg) was added followed by pyridine (3.53 kg). The resulting suspension was cooled to −10° C. under nitrogen and stirred at −5°±5° C. as t-butylchlorodiphenylsilane (684 g, 2.49 mol) was added dropwise. The resulting mixture was stirred at −5°±5° C. until the reaction was complete (as monitored by TLC (10:1 methylene chloride/methanol) and HPLC (4.6×250 mm Zorbax RxC8 (5 micron); 60:40 acetonitrile-aq. NH$_4$OAC (0.05 M) at 1.5 ml/min; UV detection at 254 nm)). Water (16 kg) was added and the mixture was stirred for 30 minutes to precipitate the product, then the mixture was cooled to 0° C. for 30 minutes. The solid was isolated by filtration and the product cake was washed with cold water and sucked dry with air to provide the crude product as an off-white solid. The crude solid was taken up in pydridine (3 kg) and concentrated under vacuum at 60° C. to remove water. The dry solid residue was slurried with methanol (10 kg) at 60° C. for 1–2 hours and filtered while hot. The filtrate was concentrated under vacuum and the solid residue was refluxed with isopropyl acetate (7 kg) for 30 minutes. The mixture was cooled to 20° C. and filtered. The filter cake was dried under vacuum at 50° C. to provide the title compound as a white solid (555 g).

b) (R)-9-[2-(Stearoyloxymethyl )-4-(t-butyldiphenylsilyloxy)butyl]guanine

The product of Example 16, step a) (555 g, 1.113 mol) was charged to a 50 liter Buchi evaporator. Pyridine (2.7 kg) was added dropwise to dissolve the solid and the mixture was distilled to dryness under vacuum at 60° C. The residue was taken up in fresh pyridine (2.7 kg) and transferred to a 22 liter flask with stirrer, addition funnel and temperature probe. The solution was cooled to −5° C. under nitrogen. A solution of stearoyl chloride (440 g, 1.45 mol) in methylene chloride (1.5 kg) was added so as to maintain a temperature below 0° C. 4-(N,N-dimethylamino)pyridine (15 g, 0.12 mol) was added and the mixture was stirred at −5–0° C. for 2–4 hours until conversion was complete (as monitored by TLC (10:1 methylene chloride/methanol) and HPLC (4.6× 250 mm Zorbax RxC8 (5 micron); 60:40 acetonitrile-aq. NH$_4$OAc (0.05 M) at 1.5 ml/min; UV detection at 254 nm)). At the end of the reaction, acetonitrile (8.7 kg) was added and the mixture was stirred for not less than 15 minutes to precipitate the product. The slurry was cooled to 0° C. for 2 hours and the solid isolated by filtration and the filter cake washed with acetonitrile (2 kg). The desired product was obtained as a white solid (775 g).

c) (R)-9-[4-Hydroxy-2-(stearoyloxymethyl)butyl]guanine

A solution of the product of Example 16, step b) (765 g, 0.29 mol) in tetrahydrofuran (10 kg) was prepared in a reactor. A solution of tetra(n-butyl)ammonium fluoride in tetrahydrofuran (1.7 kg of 1 M solution, 1.7 mol) was added and the resulting clear solution was stirred at 20°±5° C. for 4 hours. Water (32 kg) was added and the resulting slurry was stirred for 1 hour and then cooled to 0° C. for 30 minutes. The precipitate was isolated by filtration and the filter cake was washed successively with water (10 kg) and acetonitrile (5 kg). After drying under vacuum at 25° C., 702 g of crude product was obtained. The crude product was dissolved in refluxing THF (4.2 kg) and water (160 g), then cooled to 40° C. and treated with methylene chloride (14.5 kg). The mixture was allowed to cool to 25°±5° C. for 1 hour, then it was cooled to 5°±5° C. for 1 hour to complete precipitation. The slightly off-white powder was isolated by filtration and dried under vacuum at 40° C. to yield the desired product (416 g).

d) (R)-9-[4-(N-Cbz-L-valyloxy)-2-(stearoyloxymethyl) butyl]guanine

A solution of N-Cbz-L-valine (169 g, 0.67 mol) in dry THF (750 ml) was prepared in a 2 liter flask with mechanical stirrer, thermometer and addition funnel. A solution of dicyclohexylcarbodiimide (69.3 g, 0.34 mol) in THF (250 ml) was added over 5 minutes and the resulting slurry was stirred at 20°±5° C. for 2 hours. The slurry was filtered and the filter cake was washed with THF (300 ml). The filtrate and wash were charged to a 3 liter flask with stirrer and thermometer. The product of Example 16, step c) (116 g, 0.22 mol) was added as a solid, with a rinse of THF (250 ml). 4-(N,N-dimethylamino)pyridine (2.73 g, 0.022 mol) was added and the white slurry stirred at 200°±5° C. Within 15 minutes, the solids were all dissolved and the reaction was complete within 1 hour (as determined by HPLC: 4.6×250 mm Zorbax RxC8 column; 85:15 acetonitrile-0.2% aq. $HClO_4$ at 1 ml/min.; UV detection at 254 nm; starting material elutes at 4.1 min. and product elutes at 5.9 min.). The reaction was quenched by addition of water (5 ml) and the solution was concentrated under vacuum to leave a light yellow semisolid. This was taken up in methanol (1.5 liters) and warmed to reflux for 30 minutes. The solution was cooled to 25° C. and the precipitate was removed by filtration. The filtrate was concentrated under vacuum to leave a viscous, pale yellow oil. Acetonitrile, (1 L) was added and the resulting white suspension was stirred at 20°±5° C. for 90 minutes. The crude solid product was isolated by filtration, washed with acetonitrile (2×100 ml) and air-dried overnight to provide the desired product as a waxy, sticky solid (122 g). This was further purified by crystallization from ethyl acetate (500 ml) and drying under vacuum at 30° C. to provide the desired product as a white, waxy solid (104 g).

e) (R)-9-[4-(L-valyloxy)-2-(stearoyloxymethyl)butyl] guanine

A solution of the product of Example 16, step d), (77 g) in warm (40° C.) ethanol (2.3 L) was charged to an hydrogenation reactor with 5% Pd-C (15.4 g). The mixture was agitated at 40° C. under 40 psi hydrogen for 4 hours, evacuated and hydrogenated for an additional 4–10 hours. The catalyst was removed by filtration and the filtrate was concentrated under vacuum to provide a white solid. This was stirred with ethanol (385 ml) at 25° C. for 1 hour, then cooled to 0° C. and filtered. The filter cake was dried with air, then under vacuum at 35° C. to yield the title compound as a white powder (46 g).

EXAMPLE 17

(R)-9-[2-(L-Valyloxymethyl)-4-(stearoyloxy)butyl]guanine a) (R)-9-[2-Hydroxymethyl-4-(stearoyloxy)butyl]guanine H2G (506 mg; 2.0 mmol) was dissolved in dry N,N-dimethylformamide (40 ml) with pyridine (400 mg; 5.06 mmol) and 4-dimethylaminopyridine (60 mg; 0.49 mmol). Stearoyl chloride (1500 mg; 4.95 mmol) was added and the mixture kept overnight at room temperature. Most of the solvent was evaporated in vacuo, the residue stirred with 70 ml ethyl acetate and 70 ml water, and the solid filtered off, washed with ethyl acetate and water and dried to yield 680 mg of crude product. Column chromatography on silica gel (chloroform:methanol 15:1) gave pure title compound as a white solid.

$^1$H NMR (DMSO-$d_6$) δ 0.86 (t, 3H); 1.25 (s, 28H); 1.51 (qui, 2H); 1.62 (m, 2H); 2.06 (m, 1H); 2.23 (t, 2H); 3.34 (d, 2H); 3.96 (ABX, 2H); 4.07 (dd, 2H); 6.30 (br s, 2H); 7.62 (s, 1H); 10.45 (s, 1H).

$^{13}$C NMR (DMSO-$d_6$) δ 13,8 (C18); 22.0 (C17); 24.4 (C3); 27.7 (C3'); 28.4–28.8 (C4–6, C15); 28.9 (C7–14); 31.2 (C16); 33.5 (C2); 38.0 (C2'); 44.0 (C1'); 60.6/61.8 (C4', C2''); 116.5 (guaC5); 137.7 (guaC7); 151.4 (guaC4); 153.5 (guaC2); 156.7 (guaC6); 172.7 (COO).

b) (R)-9-[2-(N-Boc-L-valyloxymethyl)-4-(stearoyloxy) butyl]guanine

A mixture of N-Boc-L-valine (528 mg; 2.1 mmol) and N,N'-dicyclohexyl carbodiimide (250 mg; 1.21 mmol) in dichloromethane (20 ml) was stirred over night at room temperature, dicyclohexylurea filtered off and extracted with a small volume of dichloromethane, and the filtrate evaporated in vacuo to a small volume. (R)-9-[2-Hydroxymethyl-4-(stearoyloxy)butyl]guanine (340 mg; 0.654 mmol), 4-dimethylaminopyridine (25 mg; 0.205 mmol), and dry N,N-dimethylformamide (15 ml) were added and the mixture was stirred for 4 h at 50° C. under $N_2$. The solvent was evaporated in vacuo to a small volume. Column chromatography on silica gel, then on aluminum oxide (ethyl acetate:methanol: water 15:2:1 as eluent) gave 185 mg (39%) pure title compound as a white solid.

$^1$H NMR (CHCl$_3$) δ 0.85–1.0 (m, 9H) 18-CH$_3$, CH(CH$_3$)$_2$; 1.25 (s, 28H) 4–17-CH$_2$; 1.44 (s, 9H) t-Bu; 1.60 (qui, 2H) 3-CH$_2$; 1.74 (qua, 2H) 3'-CH$_2$; 2.14 (m, 1H) 2'-CH; 2.29 (t, 2H) 2-CH$_2$; 2.41 (m,1H) CH(CH$_3$)$_2$; 4.1–4.3 (m, 6H) C1'-CH$_2$, C2''-CH$_2$, C4-CH$_2$; 5.4 (d, 1H) αCH; 6.6 (br s, 2H) guaNH$_2$; 7.73 (s, 1H) guaH8; 12.4 (br s).

$^{13}$C NMR (CHCl$_3$) δ 13,9 (C18); 17,5/18.9 (2 Val CH$_3$); 22.4 (C17); 24.7 (C3); 28.1 (C3'); 28.9–29.3 (C4–6, C15); 29.4 (C7–14); 30.7 (Val βC); 31.7 (C16); 34.0 (C2); 35.9 (C2'); 43.9 (C1'); 58.7 (Val αC); 61.4/63.6 (C4', C2''); 79.9 (CMe$_3$); 116.4 (guaC5); 137.9 (guaC7); 151.7 (guaC4); 153.7 (guaC2); 155.7 (CONH); 158.8 (guaC6); 172.1 (CHCOO); 173.5 (CH$_2$COO).

c) (R)-9-[2-(L-Valyloxymethyl)-4-(stearoyloxy)butyl] guanine

Chilled trifluoroacetic acid (2.0 g) was added to (R)-9-[2-(N-Boc-L-valyloxymethyl)-4-(stearoyloxy)butyl] guanine (180 mg; 0.25 mmol) and the solution kept at room temperature for 1 h, evaporated to a small volume, and lyophilized repeatedly with dioxane until a white amorphous powder was obtained. The yield of title compound, obtained as the trifluoroacetate salt, was quantitative.

$^1$H NMR (DMSO-$d_6$) δ 0.87 (t, 3H) 18-CH$_3$, 0.98 (dd, 6H) CH(CH$_3$)$_2$; 1.25 (s, 28H) 4–17-CH2; 1.50 (qui, 2H) 3-CH$_2$; 1.68 (qua, 2H) 3'-CH$_2$; 2.19 (m, 1H) 2'-CH; 2.26 (t, 2H) 2-CH$_2$; 2.40 (m,1H) CH(CH$_3$)$_2$; 3.9–4.25 (m, 7H) C1'-CH$_2$, C2''-CH$_2$, C4-CH$_2$, αCH; 6.5 (br s, 2H) guaNH$_2$; 7.79 (s, 1H) guaH8; 8.37 (br s, 3H) NH$_3$+; 10.73 (br s, 1H) guaNH.

$^{13}$C NMR (DMSO-$d_6$) δ 14.2 (C18); 17.9/18.3 (2 Val CH3); 22.3 (C17); 24.6 (C3); 27.7 (C3'); 28.7–29.1 (C4–6, C15); 29.2 (C7–14); 29.5 (Val βC); 31.5 (C16); 33.7 (C2); 35.0 (C2'); 44.1 (C1'); 57.6 (Val αC); 61.6/65.2 (C4', C2'');

116.1 (guaC5);116.3 (qua, J 290 Hz, CF3);137.9 (guaC7); 151.5 (guaC4); 154.0 (guaC2); 156.7 (guaC6);158.3 (qua, J 15 Hz, CF$_3$COO) 169.1 (CHCOO); 173.1 (CH$_2$COO).

EXAMPLE 18

Alternative Preparation of (R)-9-[2-hydroxymethyl-4-(stearoyloxy)butyl]guanine

H2G (7.60 g, 30 mmol) was heated to solution in dry DMF (200 ml). The solution was filtered to remove solid impurities, cooled to 20° C. (H2G cystallized) and stirred at that temperature during addition of pyridine (9.0 g, 114 mmol), 4-dimethylaminopyridine (0.46 g, 3.75 mmol) and then, slowly, stearoyl chloride (20.0 g, 66 mmol). Stirring was continued at room temperature overnight. Most of the solvent was then evaporated off in vacuo, the residue stirred with 200 ml ethyl acetate and 200 ml water and the solid filtered off, washed with ethyl acetate and water and dried to yield crude product. As an alternative to recrystallization, the crude product was briefly heated to almost boiling with 100 ml of ethyl acetate: methanol: water (15:2:1) and the suspension slowly cooled to 30° C. and filtered to leave most of the 2" isomer in solution (the 2" isomer would crystallize at lower temperature). The extraction procedure was repeated once more to yield, after drying in vacuo, 6.57 g (42%) of almost isomer free product.

EXAMPLE 19

Preparation of Crystalline (R)-9-[2-stearoyloxymethyl)-4-(L-valyloxy)butyl]guanine The product of Example 16, step c) (20.07 g, 32.5 mmol) was dissolved in absolute ethanol (400 ml) with heating, filtered, and further diluted with ethanol (117.5 ml). To this solution was added water (HPLC grade, 103.5 ml), and the mixture was allowed to cool to 35–40° C. After the mixture was cooled, water (HPLC grade, 931.5 ml) was added at a constant rate over 16 hours with efficient stirring. After all the water was added, stirring was continued for 4 hours at room temperature. The resulting precipitate was filtered through paper and dried under vacuum at room temperature to obtain the title compound as a white, free flowing crystalline powder (19.43 g, 97%), m pt 169–170° C.

EXAMPLE 20

9-R-(4-Hydroxy-2-(L-Valyloxymethyl)butyl)guanine a) To a solution of 9-R-(4-(tert-butyldiphenylsilyloxy)-2-(hydroxymethyl)butyl)guanine (695 mg, 1.5 mmole) in DMF (30 ml) were added N-Boc-L-Valine (488 mg, 2.25 mmole), 4-dimethylamino pyridine (30 mg, 0.25 mmole) and DCC (556 mg, 2.7 mmole). After 16 hr, the reaction was recharged with N-Boc-L-valine (244 mg) and DCC (278 mg), and was kept for an additional 5 hours. The reaction mixture was filtered through Celite and poured into sodium hydrogen carbonate aqueous solution, and then it was extracted with dichloromethane. The organic phase was evaporated and purified by silica gel column chromatography, giving 950 mg of the N-protected monoamino acyl intermediate.
b) The above intermediate (520 mg, 0.78 mmole) was dissolved in THF (15 ml). To the solution was added hydrogen fluoride in pyridine (70%/30%, 0.34 ml). After two days, the solution was evaporated and coevaporated with toluene. Purification by silica gel column chromatography gave 311 mg of the protected monoamino acyl compound.
$^1$H-NMR (DMSO-d$_6$): δ 10.41 (s, 1H), 7.59 (1H), 6.26 (br s, 2H), 4.32 (t, 1H), 3.95 (m, 5H), 3.46 (m, 2H), 2.41 (m, 1H), 2.06 (m, 1H), 1.45 (m, 2H), 1.39 (s, 9H), 0.90 (d, 6H).

c) The product of step b) (95 mg, 0.21 mmole) was treated with a mixture of trifluoroacetic acid (4 ml) and dichloromethane (6 ml) for 1 hr. The solution was evaporated and freeze-dried, to give 125 mg of the unprotected monoaminoacyl product.
$^1$H-NMR (D$_2$O): δ 8.88 (s, 1H), 4.32 (m, 4H), 3.96 (d, 1H), 3.68 (m, 2H), 2.63 (m, 1H), 2.22 (m, 1H), 1,73 (m, 2H), 1.00 (m, 6H).

EXAMPLE 21

(R)-9-(2-Hydroxymethyl-4-(L-isoleucyloxy)butyl) guanine a) To a solution of (R)-9-(2-hydroxymethyl-4-hydroxybutyl) guanine (2.53 g, 10 mmole) in DMF (250 ml) were added N-Boc-L-isoleucine(2.77 g, 12 mmole), 4-dimethylaminopyridine (61 mg, 0.6 mmole) and DCC (3.7 g, 18 mmole). After reaction for 16 hr at 0°(C, N-Boc-L-isoleucine (1.3 g) and DCC (1.8 g) were recharged, and the reaction was kept overnight at room temperature. The reaction mixture was filtered through Celite and the filtrate was evaporated and purified by silica gel column chromatography, giving 1.25 g of the N-protected monoamino acyl intermediate.
$^1$H-NMR (DMSO-d$_6$): δ 10.56 (s, 1H), 7.62 (s, 1H), 6.43 (s, 2H), 4.75 (t, 1H), 4.15–3.80 (m, 5 H), 3.25 (m, 2H) 2.05 (m, 1H), 1.80–1–05 (m, 14H), 0.88 (m, 6H).
b) The intermediate from step a) (100 mg, 0.21 mmole) was treated with trifluoroacetic acid (3 m) and for 30 min at 0° C. The solution was evaporated and freeaze-dried, to give the titled unprotected mono-aminoacyl product in quantitative yield.
$^1$H-NMR (DMSO-d$_6$+D$_2$O): δ 8.72 (s, 1H), 4.15 (m, 4H), 3.90 (d, 1H), 3.42 (m, 2H), 2.09 (m, 1H), 1.83 (m, 1H), 1.61 (m, 2H), 1.15 (m, H), 0.77 (d, 3H), 0.71 (t, 3H).

EXAMPLE 22

(R)-9-[2-Hydroxymethyl-4-(L-valyloxy)butyl] guanine

The product of Example 1, step a) was deprotected with trifluoroaacetic acid in the same manner as Example 1, step c)
$^1$H-NMR (250 MHz, DMSO-d$_6$): δ 1.04 (dd, 6H), 1.55–1.88 (m, 2H), 2.21 (m, 2H), 3.48 (m, 2H), 4.00 (m, 1H), 4.13 (m, 2H), 4.34 (t, 2H), 6.9 (br s, 2H), 8.21 (s, 1H), 8.5 (br s, 3H), 11.1 (br s, 1H).

EXAMPLE 23

(R)-9-[2-(L-Valyloxymethyl )-4-(valyloxy)butyl] guanine a) (R)-9-[4-(N-Boc-L-valyloxy)-2-(N-Boc-L-valyloxymethyl)butyl]guanine Application of the technique described in Example 1, step a), but using 2.7 eqs, 0.28 eqs, and 3.2 eqs of N-Boc-L-valine, DMAP, and DCC, respectively, resulted in the title compound.
$^1$H NMR (250 MHz, CDCl$_3$) δ 0.95 (m, 12H), 1.42 (br s, 18H), 1.8 (m, 2H), 2.14 (m, 2H), 2.47 (m, 1H), 4.0–4.4 (m, 8H), 6.5 (br s, 2H), 7.67 (s, 1H).
b) (R)-9-[4-(L-Valyloxy)-2-(L-valyloxymethyl)butyl] guanine The titled compound was obtained as the tris-trifluoroacetate salt from the intermediate of Example 23 step a) by deprotection in a manner analogous to Example 1 step c).

¹H NMR (250 MHz, D₂O) δ 1.0 (m, 12H), 1.89 (m, 2H), 2.29 (m, 2H), 2.62 (m, 1H), 4.02 (dd, 2H), 4.38 (m, 6H), 4.89 (br s, ca. 10H), 8.98 (s, 1H).

EXAMPLE 24

(R)-9-[4-hydroxy-2-(stearoyloxymethyl)butyl] guanine

The titled compound is prepared according to steps a) to c) of Example 7.
¹H NMR (250 MHz, DMSO-d₆): δ 10.52 (s, 1H), 7.62 (s, 1H), 6.39 (s, 2H), 4.50 (t, 1H), 3.93 (m, 4H), 3.42 (m, 2H), 2.45 (m, 1H), 2.23 (t, 2H), 1.48 (m, 4H), 1.22 (s, 28H), 0.89 (t, 3H)

EXAMPLE 25

(R)-9-[2-Hydroxymethyl-4-(stearoyloxy)butyl] guanine

The titled compound is prepared by the procedure of Example 17, step a).
¹H NMR (DMSO-d₆) δ 0.86 (t, 3H); 1.25 (s, 28H); 1.51 (qui, 2H); 1.62 (m, 2H; 2.06 (m, 1H); 2.23 (t, 2H); 3.34 (d, 2H); 3.96 (ABX, 2H); 4.07 (dd, 2H); 6.30 (br s, 2H); 7.62 (s, 1H); 10.45 (s, 1H).

EXAMPLE 26

Alternative Preparation of (R)-9-[2-stearoyloxymethyl)-4-(L-valyloxy)butyl]guanine
a) (R)-9-[4-N-benzyloxycarbonyl-L-valyloxy)-2-(hydroxymethyl)-butyl]guanine Dry H2G (252 mg, 1mmol), 4-dimethylaminopyridine (122 mg, 1 mmol) and N-Cbz-L-valine p-nitrophenyl ester (408 mg, 1.1 mmol) were dissolved in dry dimethyl formamide (16 ml). After stirring at 23° C. for 30 hours, the organic solvent was removed and the residue carefully chromatographed (silica, 2%-7% methanol/methylene chloride) to afford the desired product as a white solid (151 mg, 31%).
b) (R)-9-[(4-N-benzyloxycarbonyl-L-valyloxy)-2-(stearoyloxymethyl)-butyl]guanine A solution of stearoyl chloride (394 mg, 1.3 mmol) in dry methylene chloride (2 ml) was added slowly dropwise under nitrogen to a solution of the product of step a) (243 mg, 1 mmol) and 4-dimethylaminopyridine (20 mg) in dry pyridine (5 ml) at −5° C. The reaction mixture was stirred at that temperature for 12 hours. Methanol (5 ml) was added and the reaction stirred for 1 hour. After removal of the solvent, the residue was triturated with acetonitrile and chromatographed (silica, 0–5% methanol/methylene chloride) to afford the desired product (542 mg, 72%).
c) (R)-9-[2-stearoyloxymethyl)-4-(L-valyloxy)butyl] guanine The product of step b) (490 mg, 1 mmol) was dissolved in methanol (30 ml) and 5% Pd/C (100 mg) added. A balloon filled with hydrogen was placed on top of the reaction vessel. After 6 hours at 23° C., TLC showed the absence of starting material. The reaction mixture was filtered through a 0.45 micron nylon membrane to remove the catalyst and the solvent was removed to afford the desired product as a white solid (350 mg, 99%) which was identical (spectral and analytical data) to Example 16.

EXAMPLE 27

Alternative Preparation of (R)-9-(4-hydroxy-2-(L-valyloxymethyl)butyl)guanine (R)-9-(4-(L-valyloxy)-2-(L-valyloxymethyl)butyl) guanine from Example 23 step b) (100 mg, 0,126 mmole) was dissolved in 0.1 N NaOH aqueous solution (6.3 ml, 0.63 mmole) at room temperature. At intervals, an aliquot was taken and neutralized with 0.5 N trifluoroacetic acid. The aliquots were evaporated and analyzed by HPLC to monitor the progress of the reaction. After 4 hours, 0.5 N trifluoroacetic acid solution (1.26 ml, 0.63 mmole) was added to the solution and the reaction mixture was evaporated. The desired product was purified by HPLC, (YMC, 50×4.6 mm, gradient 0.1% TFA+0–50% 0.1% TFA in acetonitrile, in 20 minutes, UV detection at 254 nm. Yield: 13.6%
¹H-NMR (D₂O): δ 8.81 (s, 1H), 4.36 (m, 4H), 4.01 (d, 1H), 3.74 (m, 2H), 2.64 (m, 1H), 2.25 (m, 1H), 1.73 (m, 2H), 1.03 (dd, 6H).

EXAMPLE 28

Alternative Preparation of (R)-9-(2-hydroxymethyl-4-(L-valyloxy)butyl)guanine

HPLC separation of the reaction solution from Example 27 gave the titled compound in 29.2% yield.
¹H-NMR (DMSO-d₆): δ 8.38 (s, 3H), 8.26 (s, 1H), 6.83 (br s, 2H), 4.23 (m, 2H), 4.06 (m, 2H), 3.91 (m, 1H), 3.40 (m, 2H), 2.19 (m, 2H), 1.8–1.40 (m, 2H), 0.95 (dd, 6H).

EXAMPLE 29

(R)-9-[(2-stearoyloxymethyl)-4-(L-valyloxy)butyl] guanine monohydrochloride

The product of Example 16, step d) (360 mg, 0.479 mmol) was dissolved in a mixture of methanol (10 ml) and ethyl acetate (10 ml). To the solution was added 10% Pd/C (100 mg) and 1N HCl (520 microlitres). The reaction mixture was stirred at room temperature for 2 hours under 1 atm. H₂. The reaction mixture was filtered and the solvent evaporated from the filtrate to provide the desired product as a crystalline solid (300 mg).

EXAMPLE 30

Alternative Preparation of (R)-9-[(2-stearoyloxymethyl)-4-(L-valyloxy)butyl]guanine
a) Preparation of (R)-2-Amino-6-chloro-9-[4,4-diethoxy-2-(hydroxymethyl)butyl]purine The product of Example 14, step e) (200 g) was dissolved in methanol (670 mL) and 20% aqueous K₂CO₃ (43 g K₂CO₃ in 166 mL H₂O) was added. The mixture was stirred at 25±5° C. for 30 minutes. The reaction mixture was then cooled to 0–5° C. for about 20 minutes, when a precipitate formed. Water (500 mL) was added and the slurry was mixed at 5±5° C. for 15 minutes. The resulting solid was isolated by filtration and the filter cake was washed with water (100 mL) and dried under vacuum at 20° C. to provide the desired product as a pale yellow powder (81 g). m.p. 156–158° C.
300 MHz ¹H NMR (DMSO-d₆) δ 1.04 (m, 6H); 1.36 (m, 1H); 1.55 (m, 1H); 2.10 (m, 1H); 3.40 (m, 6H); 4.06 (m, 2H); 4.48 (t, 1H); 4.78 (t, 1H); 6.93, (br s, 2H); 8.10 (s, 1H).
b) Preparation of (R)-9-[4,4-diethoxy-2-(hydroxymethyl) butyl]guanine To the product of Example 30, step a) (22.5 kg, 65.4 moles) was added an aqueous solution of KOH (prepared by dissolving 12.9 kg of KOH in 225 kg of water). This mixture was refluxed for 16 hours. The reaction was cooled to about room temperature and filtered into a larger reactor equipped with a pH electrode standardized to pH 7–10. The filtered solution was cooled to 5° C. and the product precipitated by slow addition of dilute acetic acid solution (prepared by mixing glacial acetic acid (12.6 kg, 210 moles) with 75 kg of water and cooling the mixture to 5° C.) until the pH is between 7.5 and 9.0 (target 8.5). The resulting slurry was immediately filtered and the filter cake was recharged back to the reactor. The reactor was charged with 225 kg of distilled water. The mixture was heated to not more than 50° C. for 30 minutes, then cooled to 15±10° C. and stirred for 30 minutes. The resulting precipitate was filtered by vacuum filtration, rinsed with 50 kg of distilled water and dried in a vacuum oven at not more than 45° C. for not less than 8 hours to provide the desired product as a tan solid.

c) Preparation of Stearoyl-Pivaloyl Mixed Anhydride

To 22.4 kg of stearic acid (78.7 moles) in 156.4 kg of toluene was added 8.2 kg of triethylamine (81.0 moles). The internal temperature of the resulting slurry was lowered to −5° C., then 9.52 kg of pivaloyl chloride (79.0 moles) was slowly added maintaining an internal temperature of not more than 5° C. The slurry was stirred for 2 hours at 5° C., then warmed to 20° C. and stirred for 4 hours. The triethylammonium hydrochloride precipitate was filtered and washed with 36.6 kg, 35.5 kg and 37.9 kg of toluene. The filtrate was concentrated at not more than 60° C. internal temperature and 61.1 kg of heptane was added, followed by cooling the slurry to −15 to −10° C. After 4 hours of stirring, the resulting solid was collected by vacuum filtration, blown dry for 1 hour with nitrogen and dried in a vacuum oven at room temperature for 1.5 hours to provide the desired product as white crystals (18.9 kg). A further 2.7 kg of the desired product was obtained by concentrating the mother liquors under vacuum and adding 41.1 kg of heptane. The resulting slurry was cooled to −15 to −10° C. for 4 hours, filtered, blown dry with nitrogen for 1 hour and the product dried in a vacuum oven at room temperature.

d) Preparation of (R)-9-[4,4-diethoxy-2-(stearoyloxymethyl)butyl]guanine

The product of Example 30, step b) (3.9 kg, 11.9 moles), the product of Example 30, step c) (5.2 kg, 13.6 moles) and 300 g of 4-dimethylaminopyridine (2.4 moles) were combined in 103.3 kg of THF at room temperature. After mixing for 16 hours, water (3 kg) was added. After mixing for 45 minutes, the solution was distilled at not more than 45° C. internal temperature. Ethyl acetate (62.9 kg) was charged and the solution was redistilled at not more than 45°0 C. internal temperature. Acetone (56 kg) was then added and the slurry heated to reflux (56° C.) for 15 minutes. The resulting clear solution was cooled to room temperature (not more than 15° C./hour). After 4 hours at room temperature, the resulting precipitate was filtered and rinsed with acetone (17 kg).

The mother liquors were concentrated under vacuum at not more than 45° C. Ethyl acetate (260 kg) and water (72.1 kg) were charged. The biphasic mixture was stirred and then allowed to settle. The organic phase was separated and was distilled. Ethyl acetate (200 kg) was added and the solution was redistilled. Acetone (101 kg) was charged, the solution heated to reflux (56° C.) for 15 minutes and then the solution was cooled to room temperature (not more than 15° C./hour) and the precipitate was filtered. The product was washed with acetone (19 kg, 15 kg and 15 kg), blown dry with nitrogen for 1 hour and then dried under vacuum at not more than 40° C. for approximately 6 hours to yield the desired product (3.1 kg).

e) Preparation of (R)-9-[4-hydroxy-2-(stearoyloxymethyl)butyl]guanine

The product of Example 30, step d) (3.0 kg) was slurried in THF (46 L) at 20° C. A solution of trifluoromethanesulfonic acid (2.25 kg) in 2.25 kg of water (prepared by slowly adding the acid to cold water) was added and the reaction mixture was stirred at 22° C. for 2 hours. The reaction mixture was cooled to 15° C. and quenched with a solution of NaHCO$_3$ (1.5 kg) in water (5.3 kg). Borane t-butylamine complex (powder, 340 g) was added in four portions and then the reaction temperature was increased to 35° C. and stirred for 12 hours. The reaction mixture was added to a solution of 320 g of concentrated HCl (37% aq.) in 115 kg of tap water at 5° C. This mixture was stirred for 30 minutes and the resulting precipitate was filtered and washed with acetonitrile (15 kg). The solids were reprecipitated once or twice from acetone (35 kg). A final precipitation was accomplished by dissolving the product in THF (24 kg) at 65° C., adding water (1.3 kg), cooling to 30° C. and then adding methylene chloride (105 kg). The resulting slurry was cooled to 10° C. and the precipitate was filtered to provide the desired product.

f) Preparation of (R)-9-[4-(N-benzyloxycarbonyl-L-valyloxy)-2-(stearoyloxymethyl)butyl]guanine A solution of dicyclohexylcarbodiimide (1500 g, 7.27 moles) in THF (7 L) was added to a reactor containing a mixture of N-carbobenzyloxy-L-valine (3630 g, 14.5 moles) in THF (20 L). The resulting mixture was stirred at 20±5° C. for 1–2 hours. The product of Example 30, step e) (2500 g, 4.81 moles) and 4-dimethylaminopyridine (59 g, 0.48 moles) were charged to a second reactor. To this second reactor was filtered the THF mixture from the first reactor, followed with a rinse of THF (15 L). The resulting mixture was stirred at 20±5° C. for 1–3 hours. Water (600 mL) was added and the solution was concentrated under vacuum at not more than 45° C. The residual oil was taken up in ethyl acetate (14 L) and filtered. The filtrate was washed successively with 10% aqueous sodium bicarbonate (2×14 L) and 10% brine (14 L). The organic phase was concentrated under vacuum and the residue was dissolved in methanol (10 kg) at 50–60° C. The warm solution was added gradually to a mixture of acetonitrile (30 kg) and water (13 kg) at ambient temperature. The mixture was stirred 1 hour at 15° C., then filtered to isolate the crude product, which was dried at 40° C. under vacuum to provide the desired product as a white solid (3.9 kg).

g) Preparation of (R)-9-[(2-stearoyloxymethyl)-4-(L-valyloxy)butyl]guanine

A hydrogenation reactor was charged with 10% Pd-C (400 g) and the product of Example 30, step f) (2.4 kg). Absolute ethanol (52 L) was added and the mixture was warmed to 40° C. and hydrogenated at 30–40 psi for 3–5 hours. On completion of the reaction, the catalyst was removed by filtration through diatomaceous earth and the filter cake was rinsed well with ethanol (30 L). The combined filtrates were concentrated under vacuum at not more than 60° C. to leave a white solid residue. This was dissolved in isopropanol (15 L) and isopropyl acetate (60 L) at reflux and then allowed to cool to room temperature over 4 hours. After cooling for 3 hours at 15±10° C., the precipitate was isolated by filtration, washed with isopropyl acetate (6 L) and dried under vacuum at 40° C. to provide the desired product as a white powder (864 g).

EXAMPLE 31

Alternative Preparation of (R)-9-[(2-stearoyloxymethyl)-4-(L-valyloxy)butyl]guanine a) Preparation of (2R)-4,4-Diethoxy-2-stearoyloxymethyl-butanol.

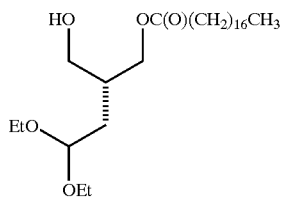

Vinyl stearate (17.76 g. 0.057 moles) was charged to a 100 mL round bottom flask with a magnetic stir bar. The flask was immersed with stirring in a 35° C. oil bath. The product of Example 14, step b) (10.0 g, 0.052 moles) and Lipase Amano PS-30 (0.20 g) were added and stirred for four hours at 35° C. The reaction was diluted with hexane (260 mL) and MTBE (115 mL) and filtered through celite. The filtrate was washed twice with water (100 mL), dried with $Na_2SO_4$, and concentrated to provide the desired product (26.21 g) as a clear oil that forms a wet solid on standing at room temperature.

b) Preparation of (2S)-4,4-Diethoxy-2-stearoyloxymethyl-butyl toluenesulfonate

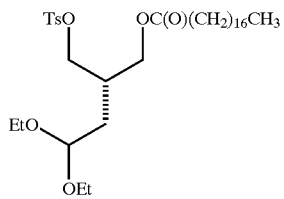

The product of Example 31, step a) (26.21 g, 0.057 mol) was dissolved in methylene chloride (75 mL) and charged into a 250 mL 3 necked flask equipped with a magnetic stir bar, condenser, $N_2$ inlet, and temperature probe. Triethylamine (14.4 g) was added followed by p-toluenesulfonyl chloride (16.3 g). The flask was purged with $N_2$ and heated to reflux (46° C.). The reaction was stirred at reflux 6 hours. The reaction was cooled to room temperature. Water (10 mL) was added and the reaction was stirred vigorously for 16 hours. The reaction mixture was poured into a 1 L separatory funnel containing ethyl acetate (350 mL) and water (350 mL). The organic layer was separated and washed with 7% (w/w) aq. sodium bicarbonate (100 mL). The organic layer was then washed with 23% (w/w) aq. sodium chloride (100 mL). The organic layer was dried with $Na_2SO_4$ and filtered. The solution was concentrated to give the desired product (29.4 g) as an oil that formed a wet solid when cooled to room temperature.

c) Preparation of (3S)-3-stearoyloxymethyl-4-toluenesulfonyloxy-butyraldehyde

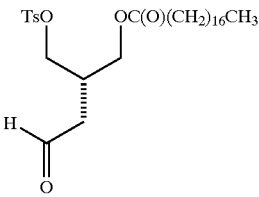

The product of Example 31, step b) (29.38 g, assayed at 23.12 g, 0.037 moles) was dissolved in THF (90 mL) and charged into a 250 mL round bottomed flask equipped with a magnetic stir bar and a temperature probe. Charged water (38 mL) and cooled to 10° C. Trifluoroacetic acid (55 mL) was poured in and the mixture was stirred for 25 minutes. The reaction mixture was poured into a 2 L separatory funnel containing 20% (w/w) $K_2CO_3$ solution (690 g), ice (600 g), and ethyl acetate (500 mL). The upper organic layer was separated. The aqueous layer was extracted a second time with ethyl acetate (500 mL). The combined organic extracts were washed with 23% (w/w) NaCl solution. The organic layer was separated, dried with $Na_2SO_4$ and filtered. The solution was concentrated to 21.5 g of an oil, dissolved in heptane (150 mL), and stirred slowly (crystals formed after 10 minutes). The slurry was stirred 15 hrs. at ambient temperature, filtered and washed with ambient heptane (20 mL). The desired product was obtained as white crystals which were dried to a constant weight of 12.3 g .

d) Preparation of (2S)-4-N-Carbonylbenzyloxy-L-valinyloxy-2-stearoyloxymethyl-butyl toluenesulfonate

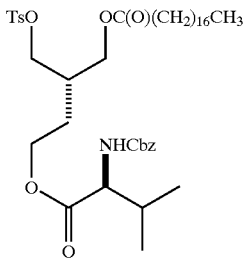

The product of Example 31, step c) (11.91 g, 0.022 mol) was charged to a 250 mL shaker bottle. THF (120 mL) and RaNi (17.8 g) were added. The reaction was pressurized to 4 atm. with $H_2$. The reaction was shaken for 1.5 hours. The reaction was filtered and washed with 20 mL THF. The filtrate is diluted with 100 mL of $CH_2Cl_2$, dried with $Na_2SO_4$, filtered, and washed with 25 ml $CH_2Cl_2$. The filtrate was charged to a 500 mL 3 necked flask equipped with a magnetic stir bar and $N_2$ inlet. N-Cbz-L-valine (13.88 g, 0.055 moles), 1,3-dicyclohexylcarbodiimide (11.37 g, 0.055 moles), and 4-dimethylaminopyridine (0.40 g, 0.003 moles) were added and the reaction was stirred for 1 hr. The reaction mixture became heterogeneous after several minutes. The reaction was filtered and washed with $CH_2Cl_2$ (50 mL). The filtrate was diluted with ethyl acetate (600 mL) and washed twice with 7% (w/w) $NaHCO_3$ solution (100 mL). The organic layer was then washed twice with 5% (w/w) $KH_2PO_4$ solution (100 mL). The organic layer was washed with 7% (w/w) $NaHCO_3$ solution (100 mL), then dried with $MgSO_4$ and filtered. The solution was concentrated to 19.46 g of oily solids. The solid was dissolved in 30 mL of 8:2 hexanes:ethyl acetate and chromatographed in two parts.

Each half was chromatographed on a Flash 40M silica gel cartridge (90 g of 32–63 μm, 60 Å silica 4.0 cm×15.0 cm) and eluted with 8:2 hexanes:ethyl acetate at 25 ml/min. 25 ml fractions were collected. Fractions were analyzed by TLC. Fractions 10–22 contained pure product in the first run and fractions 9–26 contained pure product in the second run. The fractions were combined and concentrated to provide the desired product as a clear viscous oil (12.58 g).

e) Preparation of 6-Benzyloxy-2-amino-purine

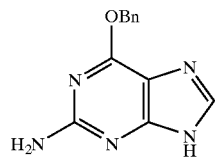

60% Sodium hydride in mineral oil (2.36 g, 0.059 moles) was charged to a 500 mL 3-neck flask equipped with magnetic stirring, temperature probe, condenser, and $N_2$ inlet. Toluene (250 mL) was added. Benzyl alcohol (50 mL) was added dropwise over 30 minutes. After addition of benzyl alcohol, the reaction was stirred 10 minutes. Then 6-chloro-2-aminopurine (5.00 g, 0.029 moles) was added and the reaction mixture was heated to reflux (115° C.) for 4.5 hours. The reaction mixture was filtered hot through a coarse glass fritted funnel and 11.65 g of wet off-white solids were obtained. The wet solids were triturated with $CH_2Cl_2$ (100 mL) and water (100 mL). After 10 minutes of stirring the solids had dissolved. The aqueous layer was separated and the pH was lowered to 9 over 3 minutes with 6 M HCl. A white solid precipitate formed. The slurry was filtered, washed with water (50 mL), and dried (in vacuo at 50° C.) to a constant weight to provide the desired product as off-white crystals (5.15 g).

f) Preparation of (R)-9-[(2-stearoyloxymethyl)-4-(N-benzyloxycarbonyl-L-valyloxy)butyl]guanine

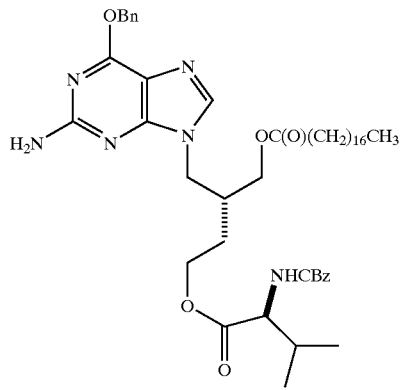

The product of Example 31, step e) (2.40 g, 0.0099 moles) was charged to a 100 mL round bottom flask equipped with magnetic stirring and a $N_2$ inlet. DMF (6 mL) and potassium carbonate (6.27 g) were added. The mixture was stirred at room temperature for 30 minutes. The product of Example 31, step d) (7.02 g, 0.0091 moles) was dissolved in DMF (21 mL) and added to the mixture. The flask was immersed in a 70° C. oil bath and stirred 24 hours. The reaction was cooled to ambient temperature and poured into a 500 mL separatory funnel containing ethyl acetate (135 mL) and 5% (w/w) $KH_2SO_4$ solution (135 mL). The top organic layer was kept and washed with 7% (w:w) $NaHCO_3$ solution (100 mL). The organic layer was dried with $MgSO_4$ and filtered. The solution was concentrated to 9.79 of oily solids. This was triturated in 50 mL of 1:1 hexanes:ethyl acetate, filtered, and concentrated to 9.10 g of yellow oil. The oil was dissolved in 20 mL of 1/1 hexanes-ethyl acetate and chromatographed on a Flash 40M silica gel cartridge (90 g of 32–63 μm, 60 Å silica, 4.0 cm×15.0 cm) eluted with 6:4 hexanes:ethyl acetate at 25 ml/min. 25 ml fractions were collected. Fractions were analyzed by TLC. Fractions 27–92 contained pure product by TLC. The pure fractions were combined and concentrated to yield the desired product as an oil (2.95 g).

g) Preparation of (R)-9-[(2-stearoyloxymethyl)-4-(L-valyloxy)butyl]guanine

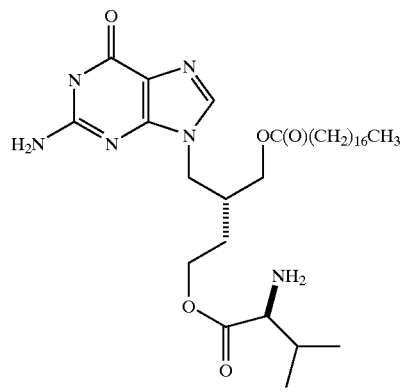

The product of Example 31, step f) (2.63 g, 0.0031 moles) was dissolved in ethanol (50 mL) and charged into a 500 mL round bottom flask. 10% Pd/C (0.5 g) was slurried in ethanol (20 mL) and added to the flask. The reaction was stirred under $H_2$ (1 atm from balloon) for 1.5 hours. The slurry was heated briefly to dissolve any solids, filtered through celite, and washed with hot ethanol (50 mL). The filtrate was concentrated to give 1.752 g of white solid. The solid was dissolved in isopropyl alcohol (10 mL) and isopropyl acetate (42 mL) at 70° C. The solution was cooled to 15° C. over 2 hours and stirred at 15° C. for 12 hours. The solution was cooled to 0° C. over 30 minutes and stirred for 1 hour. The slurry was filtered and washed with isopropyl acetate (10 mL). The solid was dried in vacuo at 50° C. to provide the desired product (0.882 g).

The mother liquors were concentrated to give 0.55 g of white solid which was dissolved in isopropyl alcohol (3 mL) and isopropyl acetate (16 mL) at 75° C. The solution was cooled to 15° C. for 2 hours, then filtered and dried as above to to provide an additional 0.181 g of the desired product.

EXAMPLE 32

Alternative Preparation of Ethyl 4,4-Diethoxy-2-ethoxycarbonyl butyrate

To a suspension of sodium ethoxide (20 g, 0.294 moles) in dimethylformamide (68 g) was added diethyl malonate (49 g, 0.306 moles) during 13 minutes. After the addition was complete, the mixture was heated to 110° C. and bromoacetaldehyde diethyl acetal (40 g, 0.203 moles) was added over 1 hour and 45 minutes. After the addition was complete, the mixture was heated at 110° C. for 7 hours. The reaction mixture was cooled to room temperature and methyl t-butyl ether (160 g) and water (100 g) were added and the mixture was stirred for 15 minutes. The organic layer was separated and treated with 7% aqueous potassium hydroxide solution (155 g). The layers were separated and the organic layer was washed with water (100 g) and then with brine (60 g). The organic layer was concentrated to give the crude desired product. The crude product was heated under house vacuum (approximately 45 mm of Hg) at 160–170° C. (bath temperature) to distill off the volatile impurities, providing 43.6 g of the desired product.

EXAMPLE 33

Alternative Preparation of (R)-9-[4,4-diethoxy-2-(hydroxymethyl)butyl]guanine

To a 100 mL one neck flask was added the product of Example 30 a) (5 g, 0.0145 moles), followed by the addition of a solution of KOH (2.05 g, 0.0445 moles) in water (20 mL). The mixture was stirred at reflux for 16–20 hours. Then the reaction mixture (at reflux) was adjusted to pH 7.0 by the addition of acetic acid. The reaction mixture was then cooled to room temperature and stirred for 30 minutes. The resulting precipitate was collected by filtration and washed with water (5 mL). The resulting solid was dried overnight at not more than 50° C. to provide 4.45 g of the desired product.

EXAMPLE 34

Alternative Purification of (R)-9-[4-hydroxy)-2-(stearoyloxymethyl)butyl]guanine as the (S)-(+)-camphorsulfonic Acid Salt In a 250 mL round bottom flask was placed the product of Example 14 i) (13.0 g) and (1S)-(+)-10-camphorsulfonic acid (5.85 g). Heptane (50 mL) was added and the mixture was stirred for 15 minutes. Then tetrahyrofuran (THF; 50 mL) was added and the mixture was stirred for 5 hours. The resulting precipitate was collected by filtration and washed with heptane (100 mL). The resulting solid was dried under vacuum at 45° C. to provide the desired product (11.3 g). HPLC analysis of the product indicated 98.76% e.e.

EXAMPLE 35

Preparation of

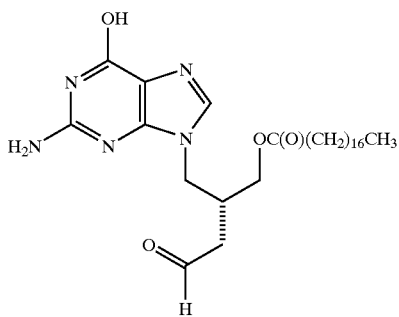

A 50 mL round bottom flask was charged with the product of Example 14 h) (1.0 g, 1.7 mmol), THF (20 mL), $H_2O$ (1 mL), and Amberlyst 15 resin (1.0 g). The solution was then heated to 65° C. for 3 hours. The solution was then filtered hot and the resin was washed with THF (2×10 mL). The solvent was then removed under vacuum to give the desired product (0.74 g, 84%).

EXAMPLE 36

Alternative Preparation of (R)-9-[4-hydroxy)-2-(stearoyloxymethyl)butyl]guanine

A 100 mL round bottom flask was charged with the product of Example 14 h) (2.45 g, 4.14 mmol), THF (25 mL), $H_2O$ (1 mL) and Amberlyst 15 resin (2.5 g). The solution was then heated to 65° C. for 3 hours. The solution was then filtered hot and the resin was washed with THF (2×15 mL). The solution of the crude aldehyde was cooled to room temperature and a solution of borane t-butylamine complex (0.3 g, 3.45 mmol), in THF/$H_2O$ (1/1 20 mL) was added dropwise to the aldehyde solution. The solution was stirred at room temperature for 1.5 hours, and the reaction was then quenched by addition of $H_2O$ (100 mL). After stirring at room temperature for an additional 30 min., the precipitate was isolated by filtration and dried to give 1.00 g (47%) of the desired product.

EXAMPLE 37

Alternative Preparation of (R)-9-[4-(N-benzyloxycarbonyl-L-valyloxy)-2-(stearoyloxymethyl)butyl]guanine a) N-Carbobenzyloxy-L-valine Anhydride A solution of dicyclohexylcarbodiimide (5 kg, 24 moles) in acetonitrile (17.5 kg) was added to a reactor containing a solution of N-carbobenzyloxy-L-valine (12.5 kg, 50 moles) in acetonitrile (200 kg). The mixture was stirred at 5+/−5° C. for 6 hours and the resulting solid was filtered off. The filtrate was concentrated under vacuum at not more then 45° C. and the residue was dissolved in toluene (50 kg) at 40° C. Heptane (50 kg) was added and the mixture was cooled to 15+/−5° C. The precipitate was filtered off and dried to give 10.2 kg of the desired product.

b) (R)-9-[4-(N-benzyloxycarbonyl-L-valyloxy)-2-(stearoyloxymethyl)butyl]-guanine A mixture of (R)-(-[4-hydroxy-2-(stearoyloxymethyl) butyl]guanine (5.2 kg, 10 moles), N-CBZ-L-valine anhydride (6.3 kg, 13 moles), 4-dimethylaminopyridine (60 g, 0.5 moles) and tetrahydrofuran (67 kg) was stirred for 2–4 hours at 25+/−5° C. Water (2 kg) was added and the mixture was concentrated under vacuum at not more then 45° C. The residue was dissolved in ethyl acetate (58 kg) and extracted with 10% aqueous sodium bicarbonate (2×50 kg) and water (1×50 kg). The ethyl acetate solution was concentrated under vacuum and the residue was dissolved in methanol (20 kg) at 50+/−5° C. The solution was cooled to 20+/−5° C. and diluted with acetonitrile (50 kg) and water (3 kg). The precipitate was filtered off and dried under vacuum to give the desired product (5.3 kg).

EXAMPLE 38

Alternative Preparation of (R)-9-[4,4-diethoxy-2-(stearoyloxymethyl)butyl]-guanine To a stirred solution of stearic acid (1.05 g) and N-mehtylmorpholine (0.62 g) in THF (13 mL) at 0–4° C. was added a solution of p-tosyl chloride (0.67 g) in THF (2 mL) at −3 to −4° C. The mixture was stirred at room temperature for 3 hours. The product of Example 14 g) (1.0 g) and 4-dimethylaminopyridine (75 mg) were added and the slurry was stirred at room temperature for 5 days and quenched with 135 mL of water. The mixture was stirred overnight and the precipitate was filtered and washed with water. The wet filter cake was dried under vacuum (40° C.) to give the desired product (1.3 g) as a light yellow powder.

EXAMPLE 39

Alternative Preparation of (R)-9-[4,4-diethoxy-2-(hydroxymethyl)butyl]guanine

The product of Example 30 a) (10.0 g, 29.1 mmoles) was added to a solution of sodium hydroxide (2.33 g, 5.82 mmoles) in water (200 mL). A solution of trimethylamine (6.61 mL of 40 wt. % solution in water, 43.6 mmoles) was charged to the suspension. The heterogeneous mixture was stirred at room temperature overnight. The reaction was diluted with water (50 mL) and then extracted with ethyl acetate (200 mL). The water layer was charged with a saturated solution of ammonium sulfate (300 mL). The mixture was stirred at room temperature for 30 hours and the resulting precipitate was filtered. The filter cake was washed with ethyl acetate (100 mL). The product was dried in a vacuum oven (high house vacuum, 45° C.) overnight to provide the desired product (7.88 g).

EXAMPLE 40

Alternative Preparation of (R)-9-[4,4-diethoxy-2-(hydroxymethyl)-butyl]guanine

A 50 gallon stainless steel reactor was purged with nitrogen and charged with the product of Example 30 a) (13.5 kg).and DMAP (0.48 kg). To the solids was added methyl t-butyl ether (108 kg), followed by triethylamine (4.0 kg). Acetic anhydride (4.64 kg) was added last. The resulting mixture was stirred at ambient temperature for 30 minutes. Distilled water (56 kg) was charged to the reactor and the contents were stirred for 30 minutes. After allowing the mixture to settle for 30 minutes, the lower layer was drained and 50 kg of saturated brine was added to the reactor. The contents of the reactor were stirred for 30 minutes and let settle for 30 minutes. The lower layer was drained and a Karl Fischer reading was done on the organic layer to assure that the water content was less than 2.5%. The organic layer was stirred at ambient temperature for 24 hours. The resulting precipitate was filtered off and the filtrate was concentrated under vacuum, followed by a methanol (22 kg) chase. To the resulting residue was added methanol (49 kg) and 10.8 kg of a 50% aqueous KOH solution. The mixture was heated to relux for one hour. The methanol was removed by distillation and the distillation residue was diluted with distilled water (112 kg) and 9.2 kg of a 50% aqueous KOH solution. The resulting mixture was heated to reflux for 16 hours. The contents of the reactor were cooled to 25° C. and were then adjusted to pH 7.0 using 37% aqueous acetic acid solution. The internal temperature of the reactor was then adjusted to 10° C. and the contents stirred for 30 minutes. The resulting slurry was centrifuged and the resulting wet cake was charged back to the reactor. To the cake was charged distilled water (70 kg). The internal temperature was adjusted to 50° C. and the contents were stirred for 30 minutes. Then the internal temperature was adjusted to 20° C. and the contents stirred for 30 minutes. The resulting slurry was centrifuged and the cake rinsed once with distilled water (15 kg). The cake was transferred to dryer trays and dried at 45° C. under vacuum for 18 hours to provide the desired product as a pale yellow powder (8.6 kg, 99% ee).

EXAMPLE 41

Alternative Preparation of (R)-9-[4-hydroxy-2-(stearoyloxymethyl)butyl]-guanine

To a 2 liter round bottom, 3-neck flask equipped with a nitrogen inlet, temperature probe, rubber septum and mechanical stirrer was charged stearic acid (25.0 g), THF (525 mL) and triethylamine (12.2 mL). The resulting solution was cooled to $^{3}$0° C. using an ice/salt bath. Pivaloyl chloride (10.3 mL) was added slowly via a syringe, maintaining the reaction temperature at less than 5° C. The resulting slurry was stirred at 0±5° C. for 2 hours. The ice bath was removed and the reaction allowed to warm to room temperature. The resulting precipitate was filtered and the filter cake was rinsed with THF (100 mL). The resulting clear filtrate was added to a 3 liter 3-neck flask (equipped with a nitrogen inlet and mechanical stirrer) charged with the product of Example 40 (22.5 g) and DMAP (1.7 g). The reaction mixture was stirred overnight at room temperature. The reaction mixture was then cooled to 18° C. and a room temperature solution of 1:1 aqueous triflic acid (27.5 g triflic acid) was added slowly, maintaining the temperature at less than 23° C. The resulting solution was stirred at approximately 22 C. for 4.5 hours. Then the reaction mixture was cooled to 18° C. and diulted with water (70 mL). Sodium bicarbonate was added to adjust the pH to 6–7 (target 6.5). The mixture was stirred at room temperature for 30 minutes.

The bath temperature was set at 35° C. and the borane-t-butylamine complex (4.52 g) was added in several portions over 50 minutes. The reaction mixture was stirred at 35° C. overnight. An additional portion of borane-t-butylamine (200 mg) was added and the mixture stirred for an additional 3 hours. The reaction mixture was quenched by pouring it into a cold solution of 5 mL of HCL in 625 mL of water. The resulting pH was 5–6 (target less than pH 6). The resulting mixture was stirred for 3 hours at room temperature and then filtered. The filter cake was dried overnight under house vacuum at 35° C. The filter cake,optionally, can be washed with acetonitrile prior to drying. The dried solid was suspended in acetone (1100 mL) and heated to reflux. The slurry was held at reflux for 30 minutes and then cooled to room temperature. After stirring at room temperature for one hour, the mixture was filtered. The filter cake was air-dried on the filter funnel for 30 minutes and then suspended in THF (350 mL). The THF mixture was heated to reflux and water (35 mL) was added. The flask containing the mixture was removed from the heating bath and allowed to cool. When the temperature reached less than 30° C., ethyl acetate (1050 ml) was added and the mixture was stirred for one hour at room temperature. The resulting slurry was filtered and the filter cake was dried overnight at 35° C. to provide the desired product as a white powder (30.4 g).

EXAMPLE 42

Alternative Preparation of (2S)-4-N-Carbonylbenzyloxy-L-valinyloxy-2-stearoyloxymethyl-butyl toluenesulfonate The product of Example 31 c) (6.00 g) was dissolved in THF (60 mL). Borane t-butylamine comlex (0.48 g) was added neat at room temperature. The reaction mixture was stirred at room temperature for 1.25 hours. The pH was adjusted to 7–8 by addition of 5% aqueous HCl. The reaction mixture was diluted with THF (60 mL) and was washed with 20% brine (40 mL) and then again with saturated brine (30 mL). The organic solution was filtered through a pad of silica gel, dried over magnesium sulfate (6.0 g) for one hour and filtered. The filtrate was added to the product of Example 37 a) (7.0 g) and DMAP (70 mg). The mixture was stirred under nitrogen at room temperature for about 3 hours. An additional amount of the product of Example 37 a) (0.5 g) was added and the mixture was stirred overnight at room temperature. An additional amount of the product of Example 37 a) (0.5 g) was added and the mixture was stirred overnight. The reaction mixture was diluted with ethyl acetate (90 mL) and washed with half-saturated sodium bicarbonate (90 mL), with brine (60 mL), with 5% $KH_2PO_4$ (60 mL) and brine (60 mL). The organic solution was dried over sodium sulfate and concentrated to provide the desired product as a yellow oil (6.88 g).

EXAMPLE 43

(R)-2-Amino-6-chloro-9-[4-(N-benzyloxycarbonyl-L-valyloxy)-2-(stearoyloxymethyl)butyl]purine A 100 ml round bottom 3-neck flask was charged with lithium hydride (58 mg, 7.3 mmol) and DMF (10 mL). 2-Amino-6-chloropurine (1.14 g, 6.72 mmol) was added al at once at room temperature. The mixture was stirred at room temperature for 40 minutes under nitrogen. The product of Example 31 d) (5.2 g, 6.72 mmol) as a solution in DMF (10 mL) was added dropwise. After complete addition, the reaction mixture was stirred at 40–50° C. under nitrogen for 27 hours. The reaction mixture was cooled to room temperature and poured into a separatory funnel containing ethyl acetate (100 mL) and 5% aqueous $KH_2PO_4$ (100 mL). The organic layer was separated and washed with saturated aqueous sodium bicarbonate (50 mL) and brine (50 mL). The organic phase was concentrated under vacuum. The crude product was dissolved in methylene chloride (5 mL) and chromatographed on flash silica gel (10 g) (eluent: 1% methanol/methylene chloride (1000 mL), 5% methanol/methylene chloride(250 mL)) to provide the desired product (3.06 g).

EXAMPLE 44

Alternative Preparation of (R)-9-[4-(N-benzyloxycarbonyl-L-valyloxy)-2-(stearoyloxymethyl)butyl]guanine A 25 mL round bottom flask was charged with the product of Example 43 (0.2 g, 0.26 mol), triethylamine (0.20 mL of 40% aq. solution), THF (4 mL) and water (1 mL). The resulting solution was stirred at room temperature for 20 hours. The solvent was removed under vacuum and the residue was dissolved in ethyl acetate (20 mL). This solution was dried over sodium sulfate and the solvent was evaporated under vacuum. The crude product was chromatographed on flash silica gel (10 g) (eluant: 1/10 methanol/methylene chloride (400 mL)) to give the desired product as a colorless oil (0.15 g).

EXAMPLE 45

Alternative Preparation of (R)-9-[4-(N-benzyloxycarbonyl-L-valyloxy)-2-(stearoyloxymethyl)butyl]guanine The product of Example 43 (145 mg, 0.188 mol) was dissolved in glacial acetic acid (1.9 mL) and the solution was heated to 110° C. for 3 hours. The solution was then cooled to room temperature and the acetic acid was removed by distillation under reduced pressure. The residue was dissolved in ethyl acetate and washed with water, aqueous sodium bicarbonate and bringe. The organic solution was evaporated under reduced pressure to give the desired product (134 mg).

EXAMPLE 46

Alternative Preparation of (R)-2-Amino-6-chloro-9-[4,4-diethoxy-2-(hydroxymethyl)butyl]purine DBU (36.8 g, 0.24 mol) was added to a suspension of 2-amino-6-chloropurine (41 g, 0.24 mol) in DMF (340 mL) at room temperature under nitrogen. After 5 minutes, the product of Example 14 d) (85 g, 0.22 mol) was added. The mixture was stirred at 40–45° C. for 15–20 hours. Then the mixture was diluted with methyl t-butyl ether (340 mL), toluene (340 mL), water (340 mL) and brine (340 mL). After mixing for 15 minutes, the organic layer was separated and the aqueous layer was extracted with toluene (2×300 mL). The combined organic layer was washed with water (500 mL) and concentrated under vacuum at 60° C. bath temperature. The resulting oil was diluted with methanol (260 mL) and cooled to 5° C. A solution of $K_2CO_3$ (16 g, 0.12 mol) in water (65 mL) was added over 15 minutes maintaining the reaction mixture temperature below 10° C. The mixture was stirred at 10° C. for 1 hour. Then the mixture was diluted with brine (500 mL) and stirred for 30 minutes. The resulting solid was filtered, washed with 5% methanol in water (50 mL) and the filter cake was dried to give the desired product as a white solid (39 g).

EXAMPLE 47

Alternative Preparation of (R)-2-Amino-6-chloro-9-[4,4-diethoxy-2-(acetoxymethyl)butyl]purine 2-Amino-6-chloropurine (0.6 g, 3.6 mmol) and tert-butylimino-tri(pyrrolidino)phosphorane (1.1 g, 3.6 mmol) were mixed in anhydrous THF (4 mL) for 10 minutes at 40° C. The product of Example 14 d) (1.16 g, 3.0 mmol) was added and the mixture was stirred at 41–43° C. overnight. The THF was removed by evaporation under vacuum and the residue was diluted with methyl t-butyl ether (10 mL), water (5 mL) and brine (5 mL). The organic layer was separated and the aqueous layer was extracted with toluene (2×10 mL). The combined organic layer was washed with-water (25 mL) and concentrated under vacuum. The residue was slurried with methyl t-butyl ether (12 mL) and water (0.1 mL) and filtered. The filtrate was concentrated under vacuum and slurried with hexane (10 mL) and methyl t-butyl ether (1 mL). The resulting solid was filtered and dried to provide the desired product (0.73 g).

EXAMPLE 48

Alternate preparation of (R)-2-Amino-6-chloro-9-[4-(N-benzyloxycarbonyl-L-valyloxy)-2-(stearoyloxymethyl)butyl]purine The title compound was prepared following the procedure of Example 47, but substituting the product of Example 31 d) for the product of Example 14 d).

EXAMPLE 49

Alternate Preparation of (R)-2-Amino-6-chloro-9-[4-(N-benzyloxycarbonyl-L-valyloxy)-2-(stearoyloxymethyl)butyl]purine The title compound can be prepared following the procedure of Example 48, but substituting DBU for tert-butylimino-tri(pyrrolidino)-phosphorane.

EXAMPLE 50

2-Amino-6-iodopurine

To a 2 liter single-neck round bottom flask with a mechanical stirrer was charged 2-amino-6-chloropurine (41.0 g, 242 mmol). The flask was cooled in an ice-water bath. The the reaction flask was charged HI (47% solution, pre-cooled in a refrigerator, 250 mL) in one portion. The resulting suspension was stirred for 16 hours at ice-water bath temperature. Water (500 mL) was charged to the reaction flask. The suspension was stirred at 0° C. for 1 hour.

The precipitate was filtered and washed with water (3×250 mL). The filter cake was transferred to a 250 mL filtration flask. 6 M NaOH solution (85 mL) was added to the solid through the filter to rinse out residual solid and wash into the filter flask. The solution obtained was added slowly to a boiling solution of acetic acid (25 mL) and water (250 mL). The resulting suspension was cooled to room temperature and stirred at room temperature for 2 hours. The solid was collected by centrifugation, washed with water (2×250 mL), followed by heptane (250 mL). The solid was first spin-dried on the centrifuge for 30 minutes and then dried in a vacuum oven overnight to provide the desired product (61.3 g).

EXAMPLE 51

Alternative Preparation of (R)-9-[4-(N-benzyloxycarbonyl-L-valyloxy)-2-(stearoyloxymethyl)butyl]guanine a) (R)-2-Amino-6-iodo-9-[4-(N-benzyloxycarbonyl-L-valyloxy)-2-(stearoyloxymethyl)butyl]purine To a 50 mL single neck round bottom flask was charged the product of Example 31 d) (2.0 g, 2.58 mmol), 2-amino-6-iodopurine (0.742 g, 2.84 mmol), DBU (o.425 mL) and DMF (10 mL). The reaction mixture was stirred for 20 hours at 40° C. Ethyl acetate (30 mL) was added to the reaction mixture and stirring continued for 30 minutes. The reaction mixture was filtered and the filtered solid was washed with ethyl acetate (2×30 mL). The filtrate and washings were combined and washed with water (3×25 mL). The organic solution was evaporated under vacuum. The residue was redissolved in ethyl acetate (50 mL) and again evaporated under vacuum to azeotropically remove any residual water, providing the desired product (2.1 g).

$^1$H NMR (300 MHz, $d_6$-DMSO): δ8.06 (s, 1H), 7.36 (br s, 5H), 6.78 (br s, 2H) 3.85–4.2 (m, 9H), 2.15 (t, 2H), 0.8–1.7 (m, 43H) Mass Spec. (ESI): 863 (M+H)$^+$ b) Alternative Preparation of (R)-2-Amino-6-iodo-9-[4-(N-benzyloxycarbonyl-L-valyloxy)-2-(stearoyloxymethyl)butyl]purine The desired product was obtained following the procedure of Example 51 a) with the replacement of DBU by $K_2CO_3$ (1.5 g).

c) (R)-9-[4-(N-benzyloxycarbonyl-L-valyloxy)-2-(stearoyloxymethyl)butyl]-guanine The product of Example 51 a) (3.4 g, 3.94 mmol), acetonitrile (45 mL), water (35 mL), acetic acid (45 mL) and sodium acetate (3.05 g) were mixed and heated to reflux (86–87° C.) for 30 hours. The volatile solvent was revoed by evaporation under reduced pressure. The aqueous layer was extracted with ethyl acetate (3×200 mL). The combined extracts were mixed with saturated sodium bicarbonate (2×100 mL) for 30 minutes. The organic layers were separated and washed with saturated sodium bicarbonate (100 mL), followed by water washes (3×100 mL). The organic solvent was evaporated under reduced pressure. To the residue was added anhydrous ethyl acetate (3×200 mL), with evaporation of the solvent each time under reduced pressure, to provide a solid. The solid was recrystallized from refluxing acetonitrile (50 mL). After cooling the acetonitrile mixture to room temperature, it was allowed to stand at room temperature overnight and then was cooled to −13° C. for 30 minutes. The resulting solid was collected by filtration, washed with acetonitrile (2×10 mL) and dired in a vacuum oven to provide the desired product (2.4 g).

EXAMPLE 52

(R)-2-Amino-6-iodo-9-[4,4-diethoxy-2-(acetoxymethyl)butyl]purine

To a 100 mL single neck round bottom flask was charged the product of Example 14 d) (9.3 g, 23.9 mmol), 2-amino-6-iodopurine (4.8 g, 18.4 mmol), DBU (3.6 mL, 24.0 mmol) and DMF (50 mL). The mixture was stirred for 16 hours at 45° C. The reaction mixture was cooled to room temperature and ethyl acetate (250 mL) was added and stirring continued for 30 minutes. The reaction mixture was filtered and the filtered solid was washed with ethyl acetate (2×125 mL). The filtrate and washings were combined and washed with water (4×50 mL). The organic solution was evaporated under reduced pressure. Ethyl acetate (50 mL) was added to the residue and evaporated under reduced pressure. Methyl t-butyl ether (300 mL) was added to the residue and stirred. The resulting solid was filtered and dried to provide the desired product (8.8 g).

($K_2CO_3$ can be used in place of DBU in the above procedure to provide the desired product).

$^1$H NMR (300 MHz, CDCl$_3$): δ7.81 (s, 1H), 5.12 (br s, 2H), 4.61 (t, 1H), 4.16 (m, 1H), 4.04 (m, 2H), 3.62 (m, 2H), 3.48 (m, 2H), 2.52 (m, 1H), 2.03 (s, 3H), 1.79 (s, 1H), 1.69 (m, 2H), 1.19 (m, 6H).

EXAMPLE 53

Alternative Preparation of (R)-9-[(2-stearoyloxymethyl)-4-(L-valyloxy)butyl]-guanine a) Preparation of (R)-9-[4-(N-benzyloxycarbonyl-L-valyloxy)-2-(stearoyloxymethyl)butyl]-guanine To a 500 mL round bottom flask was added the product of Example 30 e) (10.4 g, 20.0 mmol), the product of Example 37 a) (11.7 g, 24.2 mmol), DMAP (52 mg, 0.43 mmol) and THF (170 mL). The mixture was stirred at room temperature for 4 hours. Water (10 mL) was added and the solvent was evaporated under reduced pressure (bath temperature of approximately 45° C.). Residual THF was chased with ethyl acetate (40 mL). The residue was dissolved in ethyl acetate (200 mL) and the solution was washed with saturated sodium bicarbonate (3×100 mL) and then water (100 mL) and the organic solution was evaporated under reduced pressure (bath temperature of approximately 45° C.). Residual ethyl acetate was chased with isopropanol (25 mL) to provide the desired product in crude form as 14 g of an orange, sticky solid.

b) Preparation of (R)-9-[(2-stearoyloxymethyl)-4-(L-valyloxy)butyl]-guanine

To the flask containing the crude product of Example 53 a) was added isopropanol/THF (4/1, 100 mL) and the mixture was heated to 45–50° C. to dissolve the solids. The solution was cooled to room temperature. To a separate 500 mL round bottom flask was added 10% Pd/C (1.00 g) and the flask was evacuated and back-filled with nitrogen three times. Then isopropanol/THF (4/1, 25 mL) was added. The solution of the product of Example 53 a) was then added to the catalyst flask, along with two 35 mL isopropanol/THF (4/1) rinses. The reaction flask was then evacuated and back-filled with hydrogen three times. The solution was then heated to 40–45° C. for 16 hours. Then the hydrogen-filled balloon was replaced with a condenser and the reaction mixture was heated to 65° C. for 25 minutes. The reaction mixture was then filtered through celite (6.05 g) and the filter cake was washed with isopropanol/THF (4/1, 2×50 mL). The filtrate was concentrated under vacuum (bath temperature 45° C.) and residual THF was chased with isopropanol (50 mL).

To the flask was added isopropanol (50 mL) and the mixture was heated to about 80° C. to dissolve the solids. Isopropyl acetate (150 mL) was added and heating was continued to dissolve the solid which formed. Once all solids were dissolved, the solution was cooled to room temperature and stirred for 12 hours. The resulting solid was filtered and dried to provide a light gray solid (9.0 g). This solid was added to a 500 mL round bottom flask, along with activated carbon (2.25 g) and isopropanol (200 mL). The mixture was heated to 60–65° C. for 1 hour and then filtered through celite (6.00 g). The celite cake was washed with hot isopropanol (65° C., 2×50 mL) and the filtrate was concentrated under reduced pressure (bath temperature of 50° C.). Isopropanol (40 mL) was added to the residue and the mixture was heated to 80° C. to dissolve the solids. Isopropyl acetate (120 mL) was added and heating was continued to dissolve the precipitate which formed. The solution was cooled to room temperature and stirred for 12 hours. The resulting solid was filtered and dried to give the desired product as a white solid (7.7 g).

Alternatively, the crude product of the hydrogenation reaction was mixed with isopropanol (50 mL) and the mixture was heated to 65–70° C. to dissolve the solids. Acetonitrile (65 mL) was added dropwise via an addition funnel at a rate to maintain the temperature above 55° C. During addition of the acetonitrile, a fluffy gray precipitate formed. After addition of the acetonitrile was complete, the mixture was heated at 65° C. for 30 minutes and then filtered through a pad of celite in a steam jacketed funnel. The filtrate was concentrated and residual acetonitrile was chased with isopropanol (70 mL). The resulting solid was recrystallized from isopropanol/isopropyl acetate (30/90 mL) and after stirring at room temperature for 6 hours, the solid was filtered and dried to give the desired product as a white solid (6.72 g).

EXAMPLE 54

Alternative Preparation of (R)-9-[4,4-diethoxy-2-(hydroxymethyl)butyl]-guanine a) 2-N-Acetyl-6-O-diphenylcarbamoyl-(R)-9-[4,4-diethoxy-2-(hydroxymethyl)butyl]-guanine To a 50 mL round bottom flask was added 2-N-acetyl-6-O-diphenylcarbamoylguanine (1.10 g, 2.83 mmol) and anhydrous DMF (10 mL). DBU (423 µL, 2.83 mmol) was added and the solid dissolved after stirring for 5 minutes. A solution of the product of Example 14 d) (1.0 g, 2.6 mmol) in anhydrous DMF (5.0 mL) was added and the resulting solution was stirred at 45° C. under nitrogen for 28 hours. After cooling to room temperature, the reaction mixture was diluted with ethyl acetate (40 mL) and water (20 mL). The organic layer was separated and washed with a 5% $KHSO_4$ solution, a saturated sodium bicarbonate solution and brine and then dried over sodium sulfate. The solvent was evaporated under vacuum to provide a light yellow oil, which was chromatographed on silica gel (5% heptane in ethyl acetate) to provide the desired product as a light yellow solid (460 mg).

$^1$H NMR (300 MHz, $CDCl_3$) 1.05–1.18 (m, 6H), 1.55–1.68 (m, 2H), 1.92 (s, 3H), 2.40–2.52 (m, 1H), 2.47 (s, 3H), 3.32–3.46 (m, 2H), 3.48–3.62 (m, 2H), 3.89–4.02 (m, 2H), 4.10–4.25 (m, 2H), 4.52 (t, J=5.4 Hz, 1H), 7.05–7.42 (m, 10H), 7.91 (s, 1H), 8.11 (s, 1H) ESI (−) MS m/z 603 (M−H)$^-$.

b) (R)-9-[4,4-diethoxy-2-(hydroxymethyl)butyl]-guanine

To the product of Example 54 a) (100 mg, 0.165 mmol) in a 25 mL round bottom flask was added KOH (62 mg, 0.972 mmol) and water (10 mL). The suspension was refluxed for 20 hours. The reaction mixture was cooled to room temperature and acidified to pH 5 using acetic acid. The solvent was evaporated under reduced pressure to provide the desired product as a white solid.

EXAMPLE 55

2-N-Acetyl-(R)-9-[4,4-diethoxy-2-(hydroxymethyl)butyl]-guanine

To a 50 mL round bottom flask was added 2-N-acetylguanine (547 mg g, 2.83 mmol) and the product of Example 14 d) (1.0 g, 2.6 mmol). Anhydrous DMSO (10 mL) was added, folowed by DBU (430 µL, 2.88 mmol). The resulting solution was stirred at 40° C. under nitrogen for 24 hours. After cooling to room temperature, the reaction mixture was diluted with chloroform (50 mL) and water (20 mL). The organic layer was separated and washed with water (2×) and brine and then dried over sodium sulfate. The solvent was evaporated under vacuum to provide a light yellow oil, which was chromatographed on silica gel (10% methanol in ethyl acetate) to provide the desired product as a white foam (280 mg).

$^1$H NMR (300 MHz, $CDCl_3$) 1.10–1.31 (m, 6H), 1.62–1.85 (m, 2H), 2.06 (s, 3H), 2.44 (s, 3H), 2.50–2.68 (m, 1H), 3.40–3.56 (m, 2H), 3.57–3.73 (m, 2H), 3.96–4.20 (m, 2H), 4.32–4.55 (m, 2H), 4.62 (t, J=5.5 Hz, 1H), 7.82 (s, 1H), 11.60 (s, 1H), 12.40 (s,1H).

EXAMPLE 56

Alternative Preparation of (R)-9-[(2-stearoyloxymethyl)-4-(L-valyloxy)butyl]guanine To a 500 ml 3-neck round bottom flask equipped with a magnetic stirrer and a temperature probe was added the product of Example 30f) (5.5 g), THF (65 mL) and isopropanol (65 mL). The clear solution was purged three times with nitrogen and 5% $Pd/BaCO_3$ (0.6 g) was added. The mixture was stirred at 40° C. under a hydrogen filled balloon for 16 hours. The reaction mixture was filtered through celite and the filtrate was evaporated to dryness to provide a white solid. The solid was dissolved in isopropanol (25 mL) at 70° C. and isopropyl acetate (100 mL) was added. The resulting mixture was cooled to room temperature and stirred for 1 hour. The resulting solid was filtered and dried under vacuum to provide the desired product as a white solid (3.39 g).

EXAMPLE 57

Alternative Preparation of 2-Amino-6-benzyloxypurine

To a 500 mL 3 neck round bottom flask equipped with a magnetic stirrer, temperature probe and nitrogen inlet was added 2-amino-6-chloropurine (20 g), sodium hyroxide (28 g) and benzyl alcohol (200 mL). The mixture was stirred for 20 minutes and then heated at 100° C. for 2–3 hours. The reaction mixture was then cooled to room temperature and partitioned between methyl t-butyl ether (300 mL) and water (300 mL). The aqueous layer was separated and the pH was adjusted to 7–8 with 6 M HCl. The resulting solid was filtered, washed with water (50 mL) and dried under vacuum at 50° C. for 20 hours to provide the desired product as a pale yellow solid (24.3 g).

EXAMPLE 58

Alternative Preparation of (3S)-3-stearoyloxymethyl-4-toluenesulfonyloxy-butyraldehyde To a 1 liter 3 neck round bottom flask equipped with a magnetic stirrer, temperature probe and nitrogen inlet was added the product of Example 31 b) (40 g) and THF (320 mL). The solution was cooled to 20° C. and a solution of trifluoromethane sulfonic acid (20 g) and water (20 g) was added. After stirring for 2–3 hours, the reaction mixture was quenched with sodium bicarbonate (12.0 g), followed by addition of methyl t-butyl ether (500 mL). The organic layer was separated and washed with saturated aqueous sodium bicarbonate solution (200 mL), water (200 mL) and brine (200 mL) and then was dried over sodium sulfate. The organic solution was evaporated to dryness under vacuum to give a pale yellow oil which was dissolved in hexane (300 mL) and stirred overnight. The resulting solid was filtered and dried under vacuum to give the desired product as a white solid (25.6 g).

EXAMPLE 59

Alternative Preparation of (3S)-3-stearoyloxymethyl-4-toluenesulfonyloxy-butyraldehyde To a 100 mL 3 neck round bottom flask equipped with a magnetic stirrer, temperature probe and a nitrogen inlet was added the product of Example 31 b) (6.5 g), acetic acid (30 mL) and formic acid (20 mL). After stirring at room temperature for 20 minutes, water (20 mL) was added to the mixture and stirring was continued at room temperature for 30 minutes. The resulting precipitate was filtered and dried for 1.5 hours. The solid was added to a 100 mL flask, followed by addition of hexane (90 mL). The mixture was stirred overnight. The resulting solid was filtered and dried at 40° C. udner vacuum for 20 hours to provide the desired product as a white solid (4.6 g).

EXAMPLE 60

Alternative Preparation of N-Carbobenzyloxy-L-valine Anhydride

A solution of N-Benzyloxycarbonyl-L-valine (20.0 g) in isopropyl acetate/toluene (1:1. 80 mL) was cooled to 0° C. A solution of DCC (8.2 g) in toluene (20 mL) was added slowly, at a rate such that the internal temperature of the reaction mixture was kept below 10° C. The addition funnel was washed with toluene (20 mL). The reaction mixture was stirred for 1 hour and then allowed to warm to room temperature and stirred for another 1 hour. The reaction mixture was filtered and the filter cake was washed with toluene (20 mL). Heptane (120 mL) was added to the filtrate and the resulting solution was cooled to 0–5° C. and stirred for 1 hour. The resulting solid was filtered and washed with heptane (20 mL) and then dried under vacuum at 35° C. for 18 hours to provide the desired product as a white solid (17.0 g).

EXAMPLE 61

Alternative Preparation of (R)-9-[(2-stearoyloxymethyl)-4-(L-valyloxy)butyl]guanine a) Preparation of (2R)-4,4-Diethoxy-2-stearoyloxymethyl-butanol.

Vinyl stearate (3202 g, 9.375 moles) was charged to a 12 liter 4 neck Morton flask with nitrogen inlet and mechanical stirring. Heating was applied via a 50° C. water bath. As the vinyl stearate melted, the water bath temperature was decreased to 35° C. and stirring was started. Heating and stirring was continued until the vinyl stearate was completely melted. Then the product of Example 14 b) (1800 g, 9.375 moles) and Lipase PS30 (45 g, 2.5 wt %) were added. The suspension was stirred at 35–37° C. for 22 hours. The reaction mixture was quenched by addition of 37.5% methyl t-butyl ether in heptane (2.5 L). The mixture was then filtered through celite and the celite was washed with 37.5% methyl t-butyl ether in heptane (12 L). The organic filtrates were combined and washed with water (10 L) and 23% NaCl solution (10 L). The organic solution was evaporated and methylene chloride was added (4 L). The solution was evaporated to about half of its original volume. An additional 4 L of methylene chloride was added and the solution was allowed to stand at 5° C. overnight.

b) Preparation of (2S)-4,4-Diethoxy-2-stearoyloxymethyl-butyl toluenesulfonate.

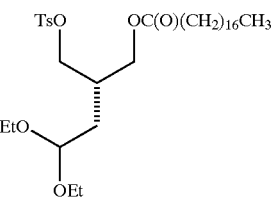

The methylene chloride product solution resulting from Example 61 a) was added to a 50 L round bottom flask equipped with mechanical stirring, water condenser, nitrogen inlet and a temperature probe. An additional 4 L of methylene chloride was added, followed by triethylamine (2349 g, 23.2 moles) and p-toluenesulfonyl chloride (2654 g, 13.92 mol). The reaction mixture was stirred for 6 hours without external heating or cooling. Water (1.8 L) was added to the reaction mixture and stirred vigorously for 17 hours. The organic layer was separated and washed with water (10 L). The aqueous layer was extracted with methylene chloride (1 L). The combined organic layers were washed with 7% sodium bicarbonate solution (10 L) and 23% NaCl solution (10 L). The solvent was evaporated to provide the desired product as a thick oil (5947 g).

c) Preparation of (3S)-3-stearoyloxymethyl-4-toluenesulfonyloxy-butyraldehyde.

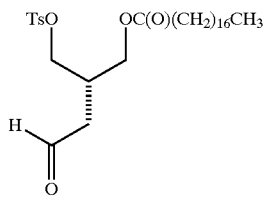

A suspension of the product of Example 61 c) (4573 g, 7.47 mol) in acetonitrile (4 L) was added to a 50 L reactor equipped with a thermocouple and nitrogen inlet. An additional 13 L of acetonitrile was added and the suspension was heated to 37° C. with steam. A solution of triflic acid (1253 mL, 14.16 mol) in water (7.6 L) was added over 20 minutes. Then the mixture was stirred at 39–42° C. for 1 hour. The reaction mixture was quenched by adding it to 20 L of 23% aqueous sodium bicarbonate solution and 35 L of methyl t-butyl ether. The reaction flask was rinsed with 5 L of methyl t-butyl ether and an additional 20 L of 23% aqueous sodium bicarbonate was added. This mixture was stirred for 10 minutes and the layers were separated. The organic layer was washed with a mixture of 25 L of 23% aqueous sodium bicarbonate solution and 15 L of 7% NaCl solution. Then the organic layer was washed with 25 L of 7% NaCl solution. The solvents were removed on a batch concentrator to provide a thick slurry. Heptane (32 L) was added to the slurry and then evaporated. Additional heptane (12 L) was added and evaporated. A further amount of heptane (40 L) was added and the suspension was heated to 44° C. in 60 minutes, causing complete dissolution. The reaction flask was cooled to 40° C. in 10 minutes by running cold water over the surface of the flask. The solution was then allowed to slowly cool to 35° C., where cyrstallization occurs. The resulting thick mixture was stirred for 14 hours. The precipitate was filtered and rinsed twice with 4 L of heptane and then dried on the filter funnel for 2 hours and then in a vacuum oven with nitrogen purge for 60 hours at room temperature. The resulting solid (3200 g), heptane (30 L) and methyl t-butyl ether (1.6 L) were combined and heated with stirring to dissolution. The resulting solution was cooled over 1 hour to 42° C. and the resulting suspension was stirred for 20 hours while cooling to room temperature. The precipitate was filtered and dried in a vacuum oven with nitrogen purge for 20 hours at room temperature to give the desired product (2860 g).

d) Preparation of (2S)-4-N-Carbonylbenzyloxy-L-valinyloxy-2-stearoyloxymethyl-butyl toluenesulfonate.

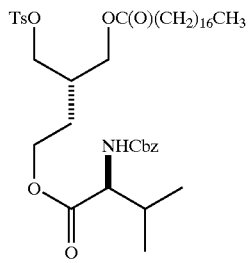

A solution of the product of Example 61 c) (511 g, 950 mmol) in THF (2.55 L) was stirred at ambient temperature in a high-pressure reactor with Raney Ni (383 g wet weight) under a 40 psi atmosphere of hydrogen for 2 hours. The suspension was filtered and the filtrate was swirled with magnesium sulfate (250 g) for 1 hour. The organic solution was filtered and added to N-Cbz-L-valine anhydride (598 g, 1.23 mol) and DMAP (5.8 g, 47.5 mmol) and stirred at ambient temperature for 20 hours. The reaction mixture was poured into 5% KH$_2$PO$_4$ (2.5 L) and extracted with methyl t-butyl ether (2.5 L). The organic layer was washed with 10% potassium carbonate (2×2.5 L) and then 23% NaCl solution (2.5 L). The volatiles were evaporated and methyl t-butyl ether (1 L) was added. The volatiles were again evaporated and this procedure repeated (usually about three times) until the Karl-Fischer test indicated less than 1 mole % water. The organic solution was then concentrated and stored as an approximately 65% w/w solution of the desired product.

e) Preparation of 2-Amino-6-iodo-(R)-9-[(2-stearoyloxymethyl)-4-(N-benzyloxycarbonyl-L-valyloxy)butyl]purine.

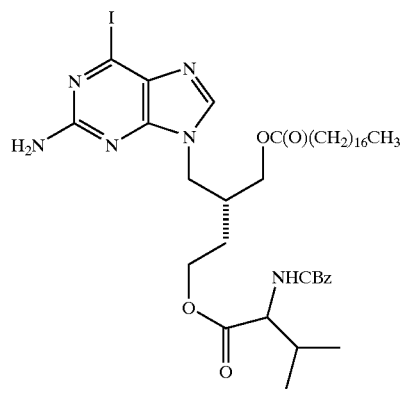

To a 500 mL flask equipped with a stir bar and a nitrogen inlet was added (2S)-4-N-Carbonylbenzyloxy-L-valinyloxy-2-stearoyloxymethyl-butyl toluenesulfonate (21.8 g, 28.2 mmol), 2-amino-6-iodopurine (9.73 g, 37.3 mmol) and potassium carbonate (11.88 g, 86.1 mmol) slurried in DMF (155 mL). The resulting mixture was stirred for 16 hours at 50° C. The mixture was then cooled to room temperature and poured into 400 mL of ethyl acetate and washed with water (3×400 mL). The aqueous washes were combined and extracted with isopropyl acetate (50 mL). The organic extracts were combined, washed with brine (200 mL), dried over magnesium sulfate and concentrated under vacuum. The residue was dissolved in acetonitrile (150 mL) and washed with heptane. The bottom layer was separated and concentrated. The residue was dissolved in methylene chloride (200 mL). Silica gel (60 g) was added and stirred for 10 minutes. This mixture was poured into a funnel containing 40 g of silica gel. The product was eluted off of the silica gel by washing with 4/1 methyl t-butyl ether/heptane. The filtrate was concentrated to provide the desired product (19.6 g).

f) Preparation of (R)-9-[(2-stearoyloxymethyl )-4-(N-benzyloxycarbonyl-L-valyloxy)butyl]guanine.

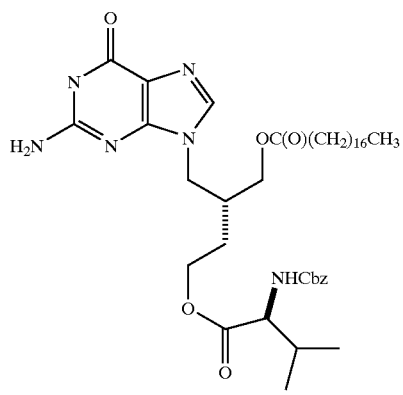

Into a 300 mL Fisher-Porter bottle (stirbar/nitrogen) was placed the product of Example 61 e) (12.36 g, 14.34 mmol) dissolved in acetonitrile (98 mL) and glacial acetic acid (98 mL), followed by addition of sodium acetate trihydrate (11.70 g, 86 mmol). The resulting mixture was stirred at 120° C. for 4 hours. The mixture was cooled to room temperature and poured into 400 mL of methyl t-butyl ether. The mixture was washed with 5% aq. NaCl (2×300 mL), 2 M potassium carbonate (150 mL), 1% NaHSO$_3$ (100 mL) and brine (100 mL). The organic layer was concentrated under vacuum. The residue was dissolved in heptane (150 mL) and extracted with acetonitrile (2×100 mL). The top layer (heptane) was concentrated to give the desired product as a thick syrup (8.98 g).

g) Preparation of (R)-9-[(2-stearoyloxymethyl)-4-(valyloxy) butyl]-guanine.

Into a 100 mL shaker was placed (R)-9-[(2-stearoyloxymethyl)-4-(N-benzyloxycarbonyl-L-valyloxy) butyl]guanine (4.53 g, 6.03 mmols) dissolved in isopropanol (45 mL), followed by addition of 4% Pd/C (450 mg). The resulting mixture was shaken under a 5 psi hydrogen for 3 days. The mixture was filtered and concentrated under vacuum to provide a waxy solid. This material was dissolved in hot isopropanol (12 mL) and isopropyl acetate was added (24 mL). The mixture was slowly cooled to 40° C. and then stirred at 0° C. for 1 hour. The precipitate was filtered and washed with isopropyl acetate (5 mL) and then dried to provide the desired product (1.53 g).

EXAMPLE 62

Alternative Preparation of (R)-9-[(2-stearoyloxymethyl)-4-(L-valyloxy)butyl]guanine a) Preparation of (2S)-4-N-t-butyloxycarbonyl-L-valinyloxy-2-stearoyloxymethyl-butyl toluenesulfonate.

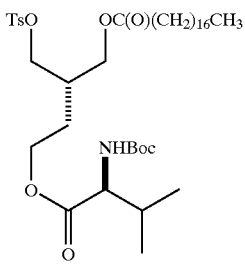

A solution of the product of Example 61 c) (3.10 g, 5.75 mmol) in THF (50 mL) was stirred at ambient temperature in a high-pressure reactor with Raney Ni (5 g wet weight) under a 5 psi atmosphere of hydrogen for 3 hours. The suspension was filtered and the filtrate was swirled with magnesium sulfate (8 g). The organic solution was filtered and N-Boc-L-valine anhydride (3.11 g, 7.47 mmol) was added, followed by DMAP (0.105 g). The resulting mixture was stirred at ambient temperature for 30 minutes. The mixture was cooled to 0° C. and treated with N,N-dimthylethylenediamine (125 mg). The resulting solution was stirred for 20 minutes and poured into methyl t-butyl ether (100 mL) and was washed with 5% $KH_2PO_4$ (100 mL), 1 M potassium carbonate (100 mL) and then 27% NaCl solution (20 mL). The organic solution was then concentrated under vacuum to provide the desired product (3.67 g).

$^1$H NMR (300 MHz, $CDCl_3$): δ 0.88 (m, 6H), 0.95 (d, 3H), 1.25 (m, 30 H), 1.45 (s, 9H), 1.55 (m, 2H), 1.70 (m, 2H), 2.1 (m, 1H), 2.21 (t, 2H), 2.46 (s, 3H), 3.94–4.2 (m, 6H), 5.0 (m, 1H), 7.37 (m, 2H), 7.78 (m, 2H). Mass Spec.=740 $(M+H)^+$ b) Preparation of 2-Amino-6-iodo-(R)-9-[(2-stearoyloxymethyl)-4-(N-t-butyloxycarbonyl-L-valyloxy) butyl]purine.

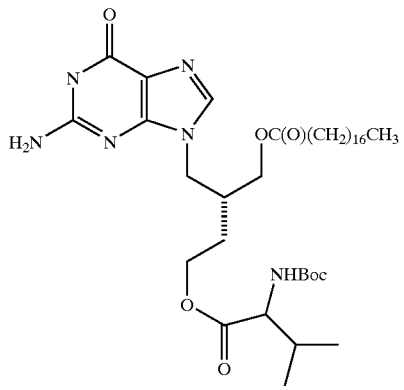

To a 100 mL flask equipped with a stir bar and a nitrogen inlet was added the product of Example 62 a) (3.67 g, 4.97 mmol), 2-amino-6-iodopurine (1.68 g, 6.46 mmol) and potassium carbonate (2.05 g, 14.9 mmol) slurried in DMF (27 mL). The resulting mixture was stirred for 16 hours at 50° C. The mixture was then cooled to room temperature and poured into 100 mL of ethyl acetate and washed with $KH_2PO_4$ (100 mL containing 20 mL of brine). The organic phase was washed with brine (2×75 mL), dried over magnesium sulfate, filtered and concentrated under vacuum. The residue was dissolved in acetonitrile (20 mL) at 50° C. The mixture was cooled to room temperature and stirred for 2 hours. The precipitate was filtered, washed with acetonitrile (2×5 mL) and dried to provide the desired product (2.79 g).

$^1$H NMR (300 MHz, $CDCl_3$): δ 0.87 (m, 6H), 0.95 (d, 3H), 1.25 (m, 30 H), 1.43 (s, 9H), 1.6 (m, 2H), 1.74 (m, 2H), 2.1 (m, 1H), 2.28 (t, 2H), 2.52 (m, 1H), 4.1–4.4 (m, 6H), 5.03 (m, 1H), 5.22 (s, 1H), 7.73 (s,1H). Mass Spec.=829 $(M+H)^+$ c) Preparation of (R)-9-[(2-stearoyloxymethyl)-4-(N-t-butyloxycarbonyl-L-valyloxy)butyl]-guanine.

Into a 4 mL vial (stir bar/nitrogen) was placed the product of Example 62 b) (0.076 g, 0.092 mmol) dissolved in acetonitrile (0.444 mL) and glacial acetic acid (0.444 mL), followed by addition of sodium acetate trihydrate (0.031 g). The resulting mixture was stirred at 100° C. for 16 hours. HPLC analysis of the mixture indicated that the desired product had been obtained, by comparison with authentic product obtained as described in Example 17 b).

d) Preparation of (R)-9-[(2-stearoyloxymethyl)-4-(valyloxy) butyl]-guanine.

Into a 20 mL vial (stirbar/nitrogen) was added (R)-9-[(2-stearoyloxymethyl)-4-(N-t-butyloxycarbonyl-L-valyloxy) butyl]-guanine (0.218 g, 0.29 mmol) dissolved in methylene chloride (3.1 mL) and trifluoroacetic acid (0.33 mL). The resulting mixture was stirred at 25° C. for 14 hours. The mixture was diluted with methylene chloride (10 mL), washed with 7% sodium bicarbonate, dried over magnesium sulfate and concentrated under vacuum to provide the desired product (161 mg).

EXAMPLE 63

Alternative Preparation of (R)-9-[(2-stearoyloxymethyl)-4-(L-valyloxy)butyl]-guanine a) Preparation of (2S)-4-N-allyloxycarbonyl-L-valinyloxy-2-stearoyloxymethyl-butyl toluenesulfonate.

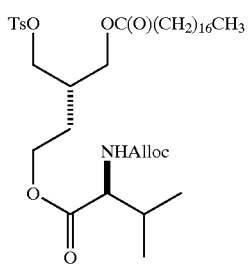

A solution of the product of Example 61 c) (15.0 g, 27.7 mmol) in THF (100 mL) was stirred at ambient temperature in a high-pressure reactor with Raney Ni (16 g wet weight) under a 5 psi atmosphere of hydrogen for 3 hours. The suspension was filtered and the filtrate was swirled with magnesium sulfate (8 g). The organic solution was filtered and N-Alloc-L-valine anhydride (13.82 g, 43.3 mmol) was added, followed by DMAP (0.203 g). The resulting mixture was stirred at ambient temperature overnight. The mixture was diluted with methyl t-butyl ether (120 mL) and was washed with 5% $KH_2PO_4$ (25 mL), 1 M potassium carbonate (100 mL) and then 27% NaCl solution (20 mL). The organic solution was then concentrated under vacuum to provide the desired product (20.6 g).

$^1$H NMR (300 MHz, $CDCl_3$): δ 0.88 (m, 6H), 0.95 (d, 3H), 1.25 (m, 30 H), 1.55 (m, 2H), 1.70 (m, 2H), 2.12 (m, 1H), 2.20 (t, 2H), 2.46 (s, 3H), 3.94–4.25 (m, 6H), 4.57 (m, 2H), 5.20–5.35 (m, 3H), 5.90 (m,1H), 7.45 (m, 2H), 7.79 (m, 2H).

b) Preparation of 2-Amino-6-iodo-(R)-9-[(2-stearoyloxymethyl)-4-(N-allyloxycarbonyl-L-valyloxy)butyl]purine.

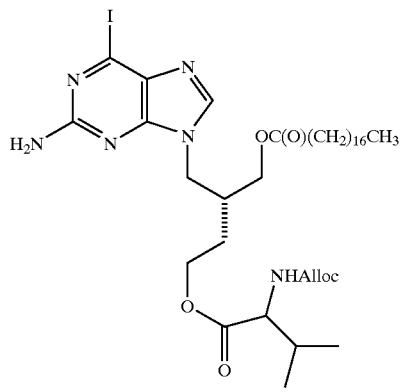

To a 500 mL flask equipped with a stir bar and a nitrogen inlet was added the product of Example 63 a) (18.43 g, 25.4 mmol), 2-amino-6-iodopurine (8.61 g, 33.0 mmol) and potassium carbonate (10.51 g, 76.2 mmol) slurried in DMF (137 mL). The resulting mixture was stirred for 16 hours at 50° C. The mixture was then cooled to room temperature and poured into 394 mL of isopropyl acetate and washed with water (3×400 mL). The organic phase was washed with brine (200 mL), dried over magnesium sulfate, filtered and concentrated under vacuum. The residue was dissolved in acetonitrile (200 mL). The mixture was stirred for 3 hours at room temperature. The precipitate was filtered, washed with acetonitrile (2×25 mL) and dried to provide the desired product (12.28 g). $^1$H NMR (300 MHz, $CDCl_3$): δ 0.89 (m, 6H), 0.98 (d, 3H), 1.29 (m, 30 H), 1.6 (m, 2H), 1.74 (m, 2H), 2.13 (m,1H), 2.28 (t, 2H), 2.52 (m, 1H), 3.9–4.4 (m, 6H) 4.58 (d, 2H), 5.20–5.35 (m, 3H), 5.90 (m, 1H), 7.76 (s, 1H). Ic Mass Spec.=813 (M+H)$^+$ c) Preparation of (R)-9-[(2-stearoyloxymethyl)-4-(N-allyloxycarbonyl-L-valyloxy)butyl]-guanine.

Into a 60 mL sealed tube (stir bar) was placed the product of Example 63 b) (1.00 g, 1.23 mmol) dissolved in acetonitrile (6.0 mL) and glacial acetic acid (6.0 mL), followed by addition of sodium acetate trihydrate (1.00 g). The resulting mixture was stirred at 120° C. for 4 hours. The mixture was cooled to room temperature and poured into 15 mL of methyl t-butyl ether, washed with 5% NaCl (2×15 mL), 2 M potassium carbonate (2×20 mL), 1% $NaHSO_3$ (2×15 mL) and brine (15 mL). The organic phase was concentrated under vacuum. The residue was chromatographed on silica gel (9/1 methylene chloride/methanol) to provide the desired product as a wax (0.67 g).

$^1$H NMR (300 MHz, $d_6$-DMSO): δ 0.85 (m, 9H), 1.21 (m, 30 H), 1.45 (m, 2H), 1.62 (m, 2H), 1.99 (m, 1H), 2.22 (t, 2H), 2.35 (m, 1H), 3.8–4.0 (m, 4H), 4.12 (t, 2H), 4.46 (m, 2H), 5.15–5.3 (m, 2H), 5.88 (m, 1H), 6.38 (b s, 2H), 7.63 (s, 1H), 10.52 (b s, 1H). Ic Mass Spec.=703 (M+H)$^+$ d) Preparation of (R)-9-[(2-stearoyloxymethyl)-4-(valyloxy)butyl]-guanine.

Into a 4 mL vial (stirbar/nitrogen) was added the product of Example 63 c) (0.07 g, 0.10 mmol) dissolved in THF (1.0 mL) and triphenylphosphine (1.6 mg) and $Pd_2(dba)_3$ (1.4 mg) and pyrrolidine (0.071 g). The resulting mixture was stirred at 25° C. for 14 hours. The mixture was concentrated under vacuum, diluted with isopropanol and stirred at 4° C. The resulting precipitate was filtered to provide the desired product (33 mg).

FORMULATION EXAMPLE A

Tablet Formulation

The following ingredients are screened through a 0.15 mm sieve and dry-mixed

| | |
|---|---|
| 10 g | (R)-9-[2-(stearoyloxymethyl)-4-(L-valyloxy)butyl]guanine |
| 40 g | lactose |
| 49 g | crystalline cellulose |
| 1 g | magnesium stearate |

A tabletting machine is used to compress the mixture to tablets containing 250 mg of active ingredient.

FORMULATION EXAMPLE B

Enteric Coated Tablet

The tablets of Formulation Example A are spray coated in a tablet coater with a solution comprising

| | |
|---|---|
| 120 g | ethyl cellulose |
| 30 g | propylene glycol |
| 10 g | sorbitan monooleate |
| add 1 000 ml | distilled water |

FORMULATION EXAMPLE C
Controlled Release Formulation

| | |
|---|---|
| 50 g | (R)-9-[2-(stearoyloxymethyl)-4-(L-valyloxy)butyl]guanine |
| 12 g | hydroxypropylmethylcellulose (Methocell K15) |
| 4.5 g | lactose | are dry-mixed and granulated with an aqueous paste of povidone. Magnesium stearate (0.5 g) is added and the mixture compressed in a tabletting machine to 13 mm diameter tablets containing 500 mg active agent.

FORMULATION EXAMPLE D
Soft Capsules

| | |
|---|---|
| 250 g | (R)-9-[2-(stearoyloxymethyl)-4-(L-valyloxy)butyl]guanine |
| 100 g | lecithin |
| 100 g | arachis oil |

The compound of the invention is dispersed in the lecithin and arachis oil and filled into soft gelatin capsules.

BIOLOGY EXAMPLE 1
Bioavailability Testing in Rats

The bioavailability of compounds of the invention were compared to the parent compound H2G and other H2G derivatives in a rat model. Compounds of the invention and comparative compounds were administered, per oral (by catheter into the stomach), to multiples of three individually weighed animals to give 0.1 mmol/kg of the dissolved prodrug in an aqueous (Example 4, 5, Comparative example 1–3, 5, 8), peanut oil (Comparative examples 4, 9, 10) or propylene glycol (Example 1–3, 6–12, 17, Comparative example 6, 7) vehicle dependent on the solubility of the test compound ingredient. The animals were fasted from 5 hours before to approximately 17 hours after administration and were maintained in metabolic cages. Urine was collected for the 24 hours following administration and frozen until analysis. H2G was analysed in the urine using the HPLC/UV assay of Stahle & Oberg, Antimicrob Agents Chemother. 36 No 2, 339–342 (1992), modified as follows: samples upon thawing are diluted 1:100 in aq dist $H_2O$ and filtered through an amicon filter with centrifugation at 3000 rpm for 10 minutes. Duplicate 30 µl samples are chromatographed on an HPLC column; Zorbax SB-C18; 75×4.6 mm; 3.5 micron; Mobile phase 0.05M $NH_4PO_4$, 3–4% methanol, pH 3.3–3.5; 0.5 ml/min; 254 nm, retention time for H2G at MeOH 4% and pH 3.33, ~12.5 min. Bioavailability is calculated as the measured H2G recovery from each animal averaged over at least three animals and expressed as a percentage of the averaged 24 hour urinary H2G recovery from a group of 4 individually weighed rats respectively injected i.v. jugularis with 0.1 mmol/kg H2G in a Ringer's buffer vehicle and analysed as above.

Comparative example 1 (H2G) was from the same batch as used for preparation of Examples 1 to 12. The preparation of Comparative example 2 (monoVal-H2G) and 3 (diVal-H2G) are shown in Examples 20 and 23. Comparative example 4 (distearoyl H2G) was prepared by di-esterification of unprotected H2G in comparable esterification conditions to step 2 of Example 1. Comparative examples 5 & 8 (Val/Ac H2G) were prepared analogously to Example 4 using acetic anhydride with relevant monovaline H2G. Comparative example 6 (Ala/stearoyl H2G) was prepared analogously to Example 6 using N-t-Boc-L-alanine in step 4. Comparative example 7 (Gly/decanoyl) was prepared analogously to Example 5 but using the step a) intermediate made with N-t-Boc-L-glycine. The preparation of Comparative examples 9 and 10 is shown in Examples 24 and 25 respectively. The results appear on Table 2 below:

TABLE 2

| Compound | $R_1$ | $R_2$ | Bioavailability |
|---|---|---|---|
| Comparative example 1 | hydrogen | hydrogen | 8% |
| Comparative example 2 | valyl | hydrogen | 29% |
| Comparative example 3 | valyl | valyl | 36% |
| Example 1 | valyl | stearoyl | 56% |
| Comparative example 4 | stearoyl | stearoyl | 1% |
| Example 2 | valyl | myristoyl | 57% |
| Example 3 | valyl | oleoyl | 51% |
| Example 4 | valyl | butyryl | 45% |
| Comparative example 5 | valyl | acetyl | 11% |
| Example 5 | valyl | decanoyl | 48% |
| Example 6 | valyl | docosanoyl | 48% |
| Example 7 | isoleucyl | stearoyl | 53% |
| Example 8 | isoleucyl | decanoyl | 57% |
| Example 9 | isoleucyl | myristoyl | 49% |
| Example 10 | valyl | 4-acetylbutyryl | 52% |
| Example 11 | valyl | dodecanoyl | 46% |
| Example 12 | valyl | palmitoyl | 58% |
| Example 17 | stearoyl | valyl | 52% |
| Comparative example 6 | alanyl | stearoyl | 23% |
| Comparative example 7 | glycyl | decanoyl | 25% |
| Comparative Example 8 | acetyl | valyl | 7% |
| Comparative Example 9 | hydrogen | stearoyl | 12% |
| Comparative Example 10 | stearoyl | hydrogen | 7% |

Comparison of the bioavailabilities of the compounds of the invention with the comparative examples indicates that the particular combination of the fatty acids at $R_1/R_2$ with the amino acids at $R_1/R_2$ produces bioavailabilities significantly greater than the corresponding diamino acid ester or difatty acid ester. For example, in this model, the compound of Example 1 displays 55% better bioavailability than the corresponding divaline ester of Comparative example 3. The compound of Example 4 displays 25% better availability than the corresponding divaline ester.

It is also apparent, for instance from Comparative examples 5, 6 and 7 that only the specified fatty acids of this invention in combination with the specified amino acids produce these dramatic and unexpected increases in pharmacokinetic parameters.

BIOLOGY EXAMPLE 2
Plasma Concentrations in Rats

A plasma concentration assay was done in male Sprague Dawley derived rats. The animals were fasted overnight prior to dosing but were permitted free access to water. Each of the compounds evaluated was prepared as a solution/suspension in propylene glycol at a concentration corresponding to 10 mg H2G /ml and shaken at room temperature for eight hours. Groups of rats (at least 4 rats in each group) received a 10 mg/kg (1 ml/kg) oral dose of each of the compounds; the dose was administered by gavage. At selected time points after dosing (0.25, 0.5, 1, 1.5, 2, 4, 6, 9, 12, 15, and 24 hours after dosing), heparinized blood samples (0.4 ml/sample) were obtained from a tail vein of each animal. The blood samples were immediately chilled in an ice bath. Within two hours of collection, the plasma was separated from the red cells by centrifugation and frozen till analysis. The components of interest were separated from the plasma proteins using acetonitrile precipitation. Following lyophilisation, and reconstitution, the plasma concentrations were determined by reverse phase HPLC with fluorescence detection. The oral uptake of H2G and other test compounds was determined by comparison of the H2G area under the curve derived from the oral dose compared to that obtained from a 10 mg/kg intravenous dose of H2G, administered to a separate group of rats. The results are depicted in Table 1B above.

BIOLOGY EXAMPLE 3

Bioavailability in Monkeys.

The compounds of Example 1 and Comparative example 3 (see Biology Example 1 above) were administered p.o. by gavage to cynomolgus monkeys.

The solutions comprised:

| | |
|---|---|
| Example 1 | 150 mg dissolved in 6.0 ml propylene glycol, corresponding to 25 mg/kg or 0.0295 mmol/kg. |
| Comparative Example 3 | 164 mg dissolved in 7.0 ml water, corresponding to 23.4 mg/kg or 0.0295 mmol/kg. |

Blood samples were taken at 30 min, 1, 2, 3, 4, 6, 10 and 24 hours. Plasma was separated by centrifugation at 2500 rpm and the samples were inactivated at 54° C. for 20 minutes before being frozen pending analysis. Plasma H2G levels were monitored by the HPLC/UV assay of Example 30 above.

FIG. 1 depicts the plasma H2G recovery as a function of time. Although it is not possible to draw statistically significant conclusions from single animal trials, it appears that the animal receiving the compound of the invention experienced a somewhat more rapid and somewhat greater exposure to H2G than the animal which received an alternative prodrug of H2G.

BIOLOGY EXAMPLE 4

Antiviral Activity

Herpes simplex virus-1 (HSV-1)-infected mouse serves as an animal model to determine the efficacy of antiviral agents in vivo. Mice inoculated intraperitoneally with HSV-1 at 1000 times the $LD_{50}$ were administered either with a formulation comprising the currently marketed anti-herpes agent acyclovir (21 and 83 mg/kg in a 2% propylene glycol in sterile water vehicle, three times daily, p.o.) or the compound of Example 29 (21 and 83 mg/kg in a 2% propylene glycol in sterile water vehicle, three times daily, p.o.) for 5 consecutive days beginning 5 hours after inoculation. The animals were assessed daily for deaths. The results are displayed in FIG. 2 which charts the survival rate against time. In the legend, the compound of the invention is denoted Ex.29 and acyclovir is denoted ACV. The percentage of mice surviving the HSV-1 infection was significantly greater following a given dose of the compound of the invention relative to an equivalent dose of acyclovir.

The foregoing is merely illustrative of the invention and is not intended to limit the invention to the disclosures made herein. Variations and changes which are obvious to one skilled in the art are intended to be within the scope and nature of the invention as defined in the appended claims.

What is claimed is:

1. A compound of the formula:

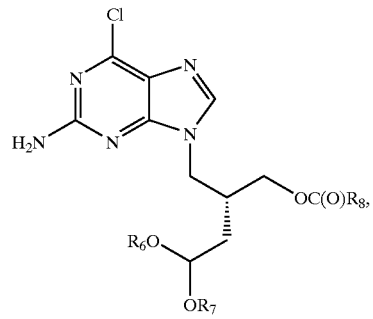

wherein $R_6$ and $R_7$ are lower alkyl or $R_6$ and $R_7$ taken together are —$CH_2CH_2$—, —$CH_2CH_2CH_2$— or —$CH_2CH_2CH_2CH_2$—, $R_8$ is $C_1$–$C_{21}$ saturated or monounsaturated, optionally substituted alkyl.

2. The compound of claim 1 wherein $R_6$ and $R_7$ are —$CH_3$ or —$CH_2CH_3$ or $R_6$ and $R_7$ taken together are —$CH_2CH_2$—, —$CH_2CH_2CH_2$— or —$CH_2CH_2CH_2CH_2$— and $R_8$ is $CH_3$.

3. The compound of claim 1 wherein $R_6$ and $R_7$ are —$CH_2CH_3$ and $R_8$ is $CH_3$.

4. The compound of claim 1 wherein $R_6$ and $R_7$ are —$CH_3$ or —$CH_2CH_3$ or $R_6$ and $R_7$ taken together are —$CH_2CH_2$—, —$CH_2CH_2CH_2$— or —$CH_2CH_2CH_2CH_2$— and $R_8$ is —$(CH_2)_{16}CH_3$.

5. The compound of claim 1 wherein $R_6$ and $R_7$ are —$CH_2CH_3$ and $R_8$ is —$(CH_2)_{16}CH_3$.

6. A compound of the formula:

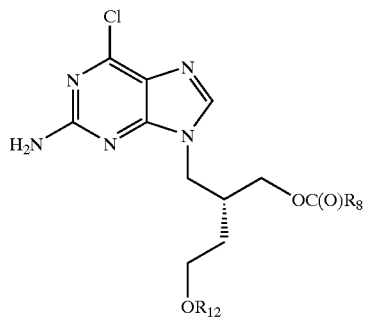

wherein $R_8$ is $C_1$–$C_{21}$ saturated or monounsaturated, optionally substituted alkyl and $R_{12}$ is —$CH(Ph)_2$, —$C(Ph)_3$ or —$Si(t-Bu)(CH_3)_2$ wherein Ph is phenyl.

7. The compound of claim 6 wherein $R_8$ is $CH_3$ and $R_{12}$ is as defined therein.

8. The compound of claim 6 wherein $R_8$ is $-(CH_2)_{16}CH_3$ and $R_{12}$ is as defined therein.

9. A compound of the formula:

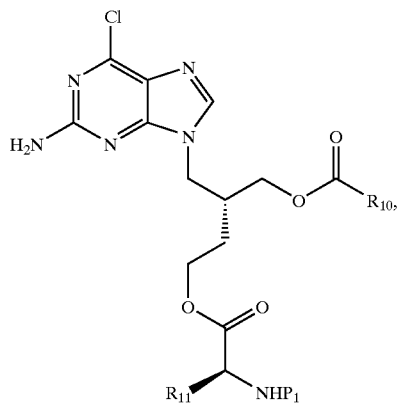

wherein $R_{10}$ is $C_3$–$C_{21}$ saturated or monounsaturated, optionally substituted alkyl, $R_{11}$ is isopropyl or isobutyl and $P_1$ is an N-protecting group.

10. The compound of claim 9 wherein $R_{10}$ is $CH_3(CH_2)_{16}-$, $R_{11}$ is isopropyl and $P_1$ is benzyloxycarbonyl, t-butyloxycarbonyl or allyloxycarbonyl.

11. The compound of claim 9 wherein $R_{10}$ is $CH_3(CH_2)_{16}-$, $R_{11}$ is isopropyl and $P_1$ is benzyloxycarbonyl.

* * * * *